United States Patent
Singidi et al.

(10) Patent No.: US 9,567,288 B2
(45) Date of Patent: Feb. 14, 2017

(54) CRYSTALLINE SALTS OF (Z)-O-OCTADEC-9-EN-1-YL O,O-DIHYDROGEN PHOSPHOROTHIOATE

(71) Applicant: RxBio Inc., Johnson City, TN (US)

(72) Inventors: Rama Krishna Reddy Singidi, Germantown, TN (US); Veeresh Gududuru, Memphis, TN (US); Mahmoud Mirmehrabi, Halifax (CA); Karin Emmons Thompson, Marion, AR (US); Gabor Jozsef Tigyi, Memphis, TN (US); Charles Ryan Yates, Collierville, TN (US); Jurriaan Strobos, Silver Spring, MD (US)

(73) Assignee: RxBio, Inc., Johnson City, TN (US)

( * ) Notice: Subject to any disclaimer, the term of this patent is extended or adjusted under 35 U.S.C. 154(b) by 0 days.

(21) Appl. No.: 14/569,383

(22) Filed: Dec. 12, 2014

(65) Prior Publication Data

US 2015/0183726 A1    Jul. 2, 2015

Related U.S. Application Data

(60) Provisional application No. 61/921,938, filed on Dec. 30, 2013.

(51) Int. Cl.
| | |
|---|---|
| C07C 229/26 | (2006.01) |
| C07F 9/203 | (2006.01) |
| C07F 9/206 | (2006.01) |
| C07F 9/205 | (2006.01) |
| C07F 9/201 | (2006.01) |
| C07F 9/24 | (2006.01) |

(52) U.S. Cl.
CPC .............. *C07C 229/26* (2013.01); *C07F 9/203* (2013.01); *C07F 9/205* (2013.01); *C07F 9/206* (2013.01); *C07F 9/2408* (2013.01); *C07B 2200/13* (2013.01)

(58) Field of Classification Search
CPC ........ C07C 229/26; C07F 9/203; C07F 9/206; C07F 9/205; C07F 9/201
See application file for complete search history.

(56) References Cited

U.S. PATENT DOCUMENTS

| | | |
|---|---|---|
| 7,217,704 B2 * | 5/2007 | Miller .................. A61K 31/661 514/119 |
| 7,947,665 B2 | 5/2011 | Miller |
| 2003/0130237 A1 | 7/2003 | Miller et al. |
| 2007/0078111 A1 | 4/2007 | Tigyi et al. |
| 2011/0301142 A1 | 12/2011 | Hutchinson et al. |
| 2012/0010424 A1 | 1/2012 | Dududuru et al. |
| 2012/0088782 A1 | 4/2012 | Terakado et al. |
| 2012/0135967 A1 | 5/2012 | Miller et al. |
| 2012/0270780 A1 * | 10/2012 | Lee ...................... C07D 261/02 514/7.7 |
| 2013/0165478 A1 | 6/2013 | Schiemann et al. |

FOREIGN PATENT DOCUMENTS

| | | |
|---|---|---|
| WO | 2005032494 | 4/2005 |
| WO | 2008140574 | 11/2008 |

OTHER PUBLICATIONS

Kendall, 1951, http://kb.osu.edu/dspace/handle/1811/14255?show=full.*

Durgam GG et al., "Synthesis, Structure-Activity Relationships, and Biological Evaluation of Fatty Alcohol Phosphates as Lysophosphatic Acid Receptor Ligands, Activators of PPPAR-gamma, and inhibitors of Autotaxin", J. Med. Chem., vol. 48, 2005.

* cited by examiner

*Primary Examiner* — Sun Jae Yoo
(74) *Attorney, Agent, or Firm* — Lihua Zheng

(57) ABSTRACT

Here provided are a salt of Z)—O-octadec-9-en-1-yl O,O-dihydrogen phosphorothioate with an L-lysine addition in crystalline form and methods of making and using the same.

2 Claims, 43 Drawing Sheets

(a) (1) bis(cyanoethyl)-N,N-diisopropylphosphoramidite, tetrazole, CH2Cl2
(2) sulfur, reflux, (b) (1) KOH, MeOH (2) HCl Scheme I 1: (Z)-Oleyl alcohol 2: O-(Z)-oleyl dichloridothiophosphate 3: O-(Z)-oleyl thiophosphate 4: O-(Z)-oleyl thiophosphate lysine salt Scheme II Scheme III Scheme IV ical compound in a desirable form.
CRYSTALLINE SALTS OF (Z)-O-OCTADEC-9-EN-1-YL O,O-DIHYDROGEN PHOSPHOROTHIOATE

GOVERNMENTAL SUPPORT

The research is partly supported by a government grant from the Biomedical Advanced Research and Development Authority (BARDA), within the Office of the Assistant Secretary for Preparedness and Response in the U.S. Department of Health and Human Services (grant# HHSO100201100036C).

FIELD OF INVENTION

The present invention relates to crystalline and/or semi-crystalline salts of (Z)—O-octadec-9-en-1-yl O,O-dihydrogen phosphorothioate, and methods of making and using the crystalline and/or semi-crystalline salts.

BACKGROUND

The compound (Z)—O-octadec-9-en-1-yl O,O-dihydrogen phosphorothioate (hereafter designated "Rx100" for the interest of simplicity), a lysophosphatidic acid ("LPA") receptor agonist and/or antagonist, may enhance cell proliferation, treat wound healing, or protect tissues such as those of the gastrointestinal and hematopoietic systems against chemotherapeutic- or radiation-induced apoptosis. See, for example, U.S. Pat. Nos. 7,217,704 and 7,947,665. The Formula I below represents the structure of the Rx100 free acid ("Rx100.FA"):

Formula I

Chemical Formula: $C_{18}H_{37}O_3PS$

Pharmaceutical compound may exist in many different forms, for example, free base, free acid, various salts, liquid, crystalline solid, hydrate, solvate, amorphous or polymorphous forms. Variations of physical forms may often cause variations of stability, solubility, bioavailability, filterability, scalability, pharmacokinetics and/or bioequivalency of a pharmaceutical compound. It is therefore desirable to make a pharmaceutical compound in a desirable form.

Rx100.FA is a pale yellow oily substance. In addition to being in a less desirable oil form it has a thiol type odor, needs storage at less than −20° C. to preserve short-term stability, has poor solubility in water, and is difficult to handle for practical purposes. Attempts to form more desirable salt forms such as the sodium or potassium salts failed to yield filterable solids.

Treatment of Rx100.FA solution in methanol with 3 equivalents of ammonia forms a precipitate which upon freeze-drying provides an Rx100.Ammonia salt powder. However, Rx100.Ammonia salt also has many undesirable features. For example, (i) ammonia may be lost during storage; ii) the salt may absorb moisture during routine handling procedures by the formation of a stick mass; iii) formation of the salt does not exclude impurities (as opposed to crystallization); and iv) additives, stabilizers found in solvents, synthesis impurities and by products may get incorporated in the drug solid during salt formation. Therefore, there is an urgent need to obtain a new Rx100 salt in an improved form with more desirable features.

water (v/v) [1:1] at 25° C. and (c) lot number 1980-20-8 Evap, isolated from evaporative crystallization from methanol:water (v/v) [1:1] at 50° C.

Figure 14:
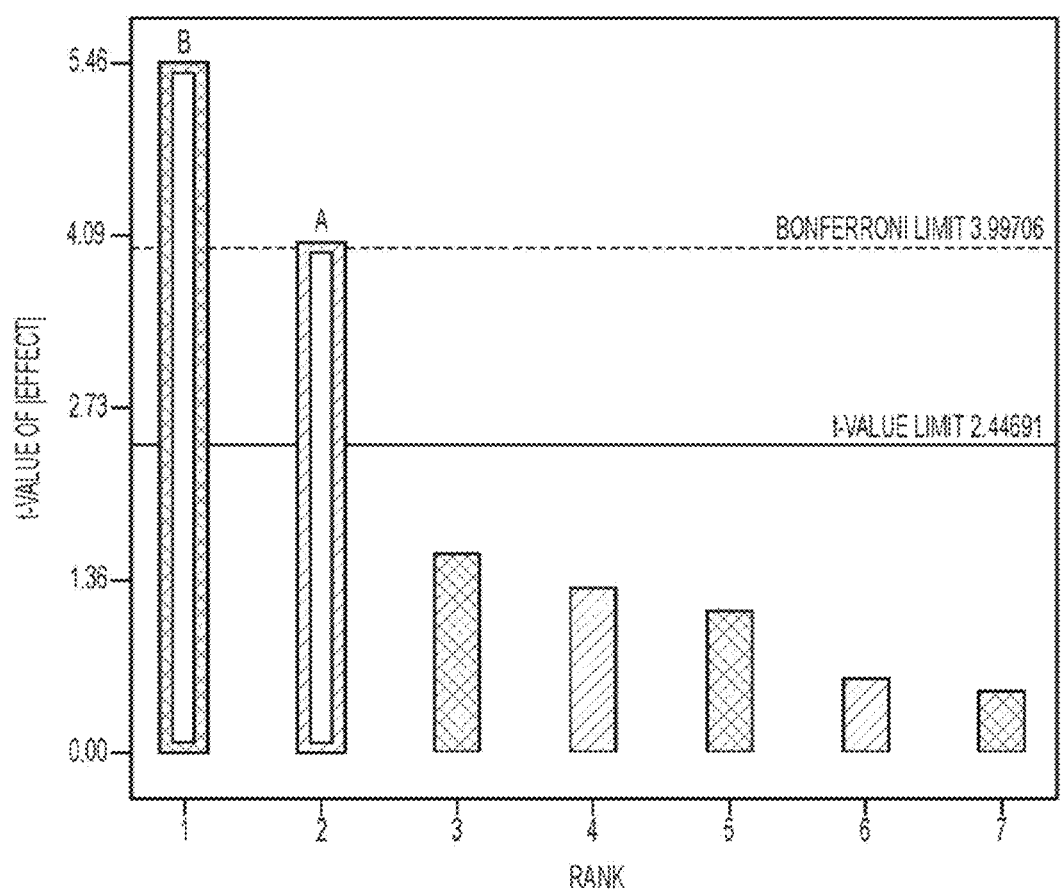

FIG. 14 shows a Pareto chart showing the effects on the quantity of impurities is captured in the alkaline extraction.

Figure 15:
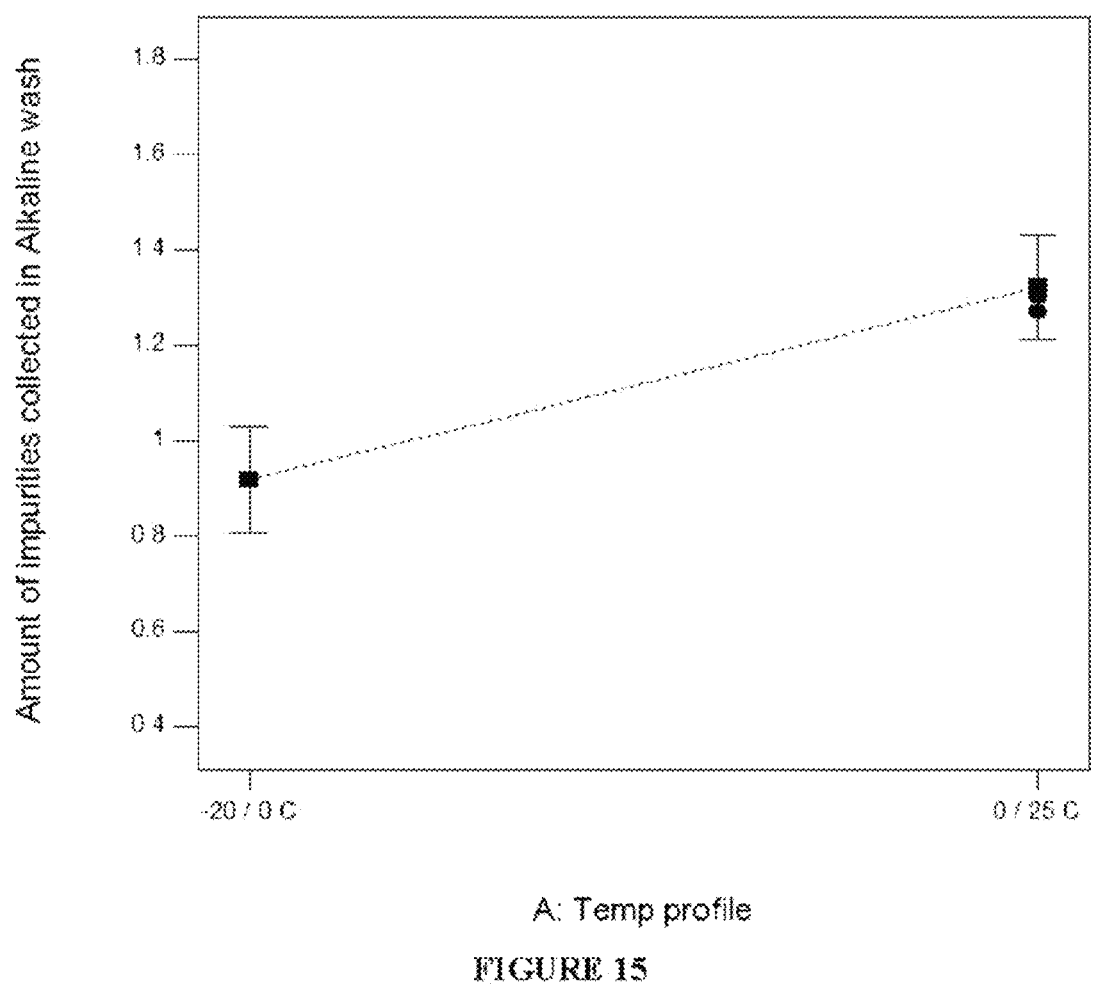

FIG. 15 shows a graph depicting the positive effect of factor A (temperature) on the quantity of impurities is captured in the alkaline extraction.

Figure 16:
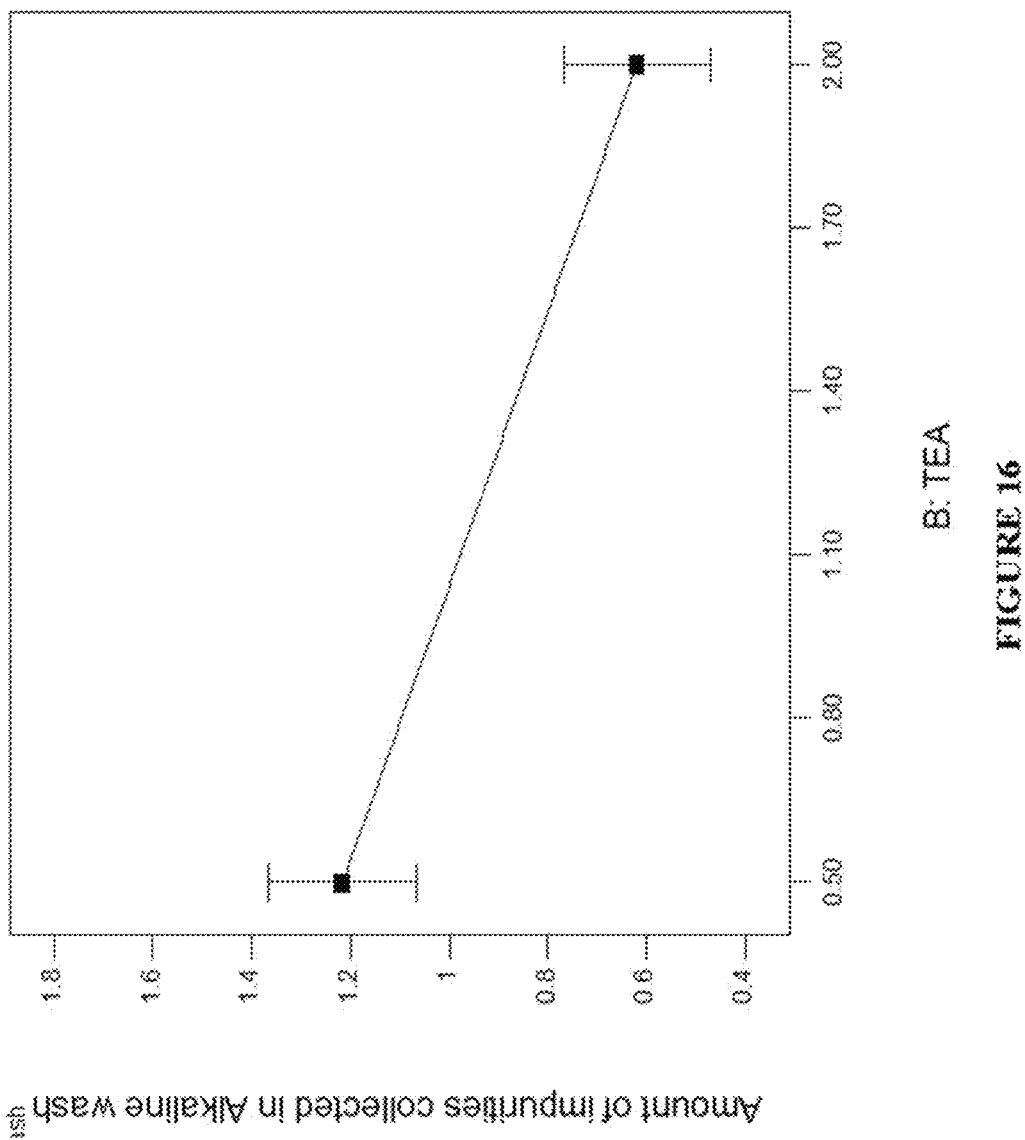

FIG. 16 shows a graph depicting the negative effect of TEA on the quantity of impurities is captured in the alkaline extraction.

Figure 17:
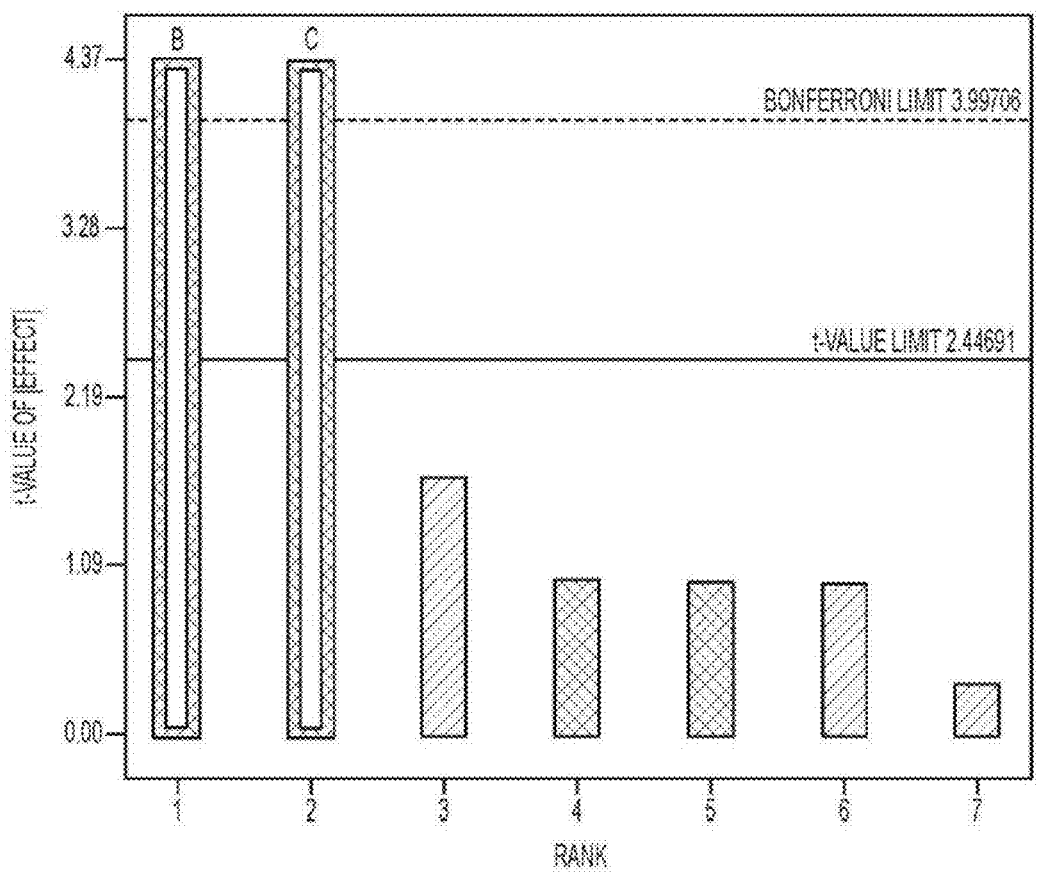

FIG. 17 shows a Pareto chart showing the effects on the level of impurities in the reaction product as measured by Proton NMR.

Figure 18:
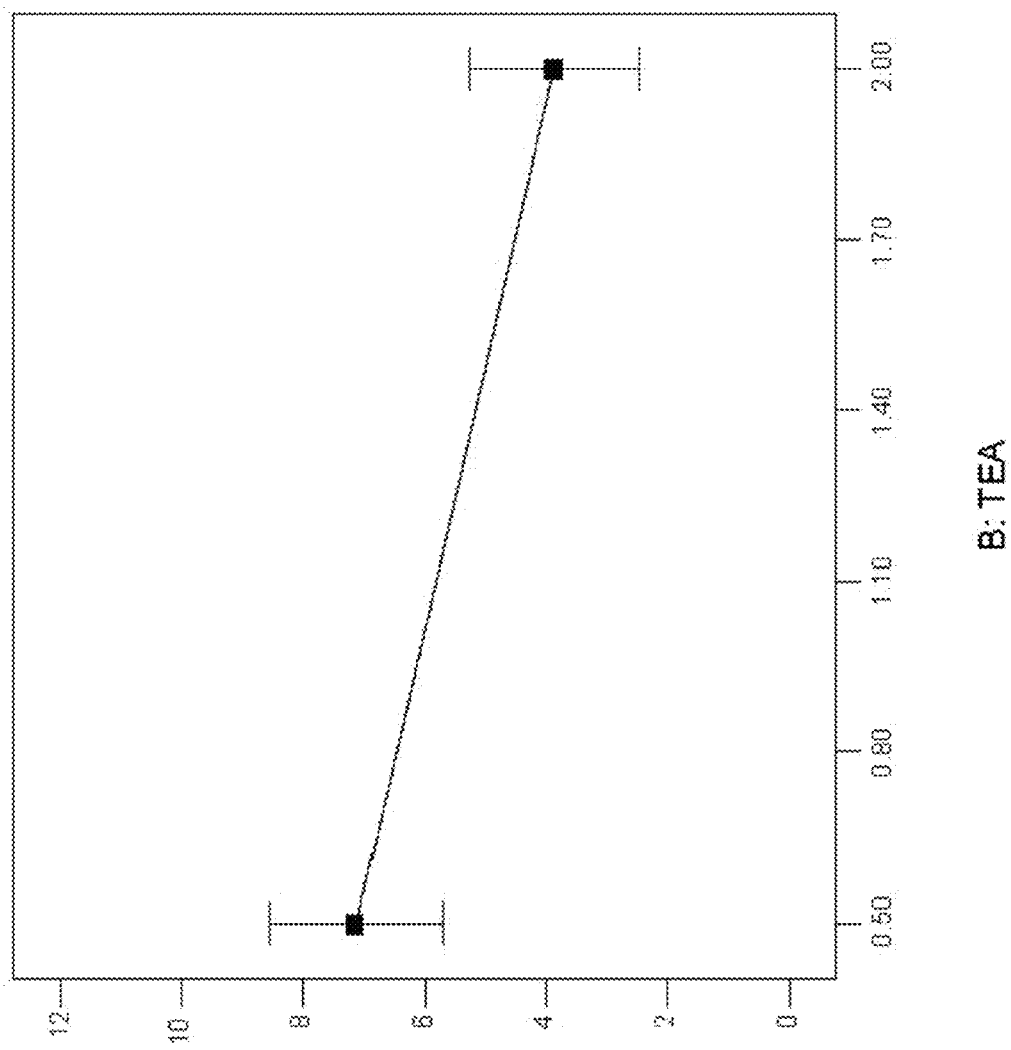

FIG. 18 shows a graph depicting the negative effect of TEA on the level of impurities in the reaction product as measured by Proton NMR.

Figure 19:
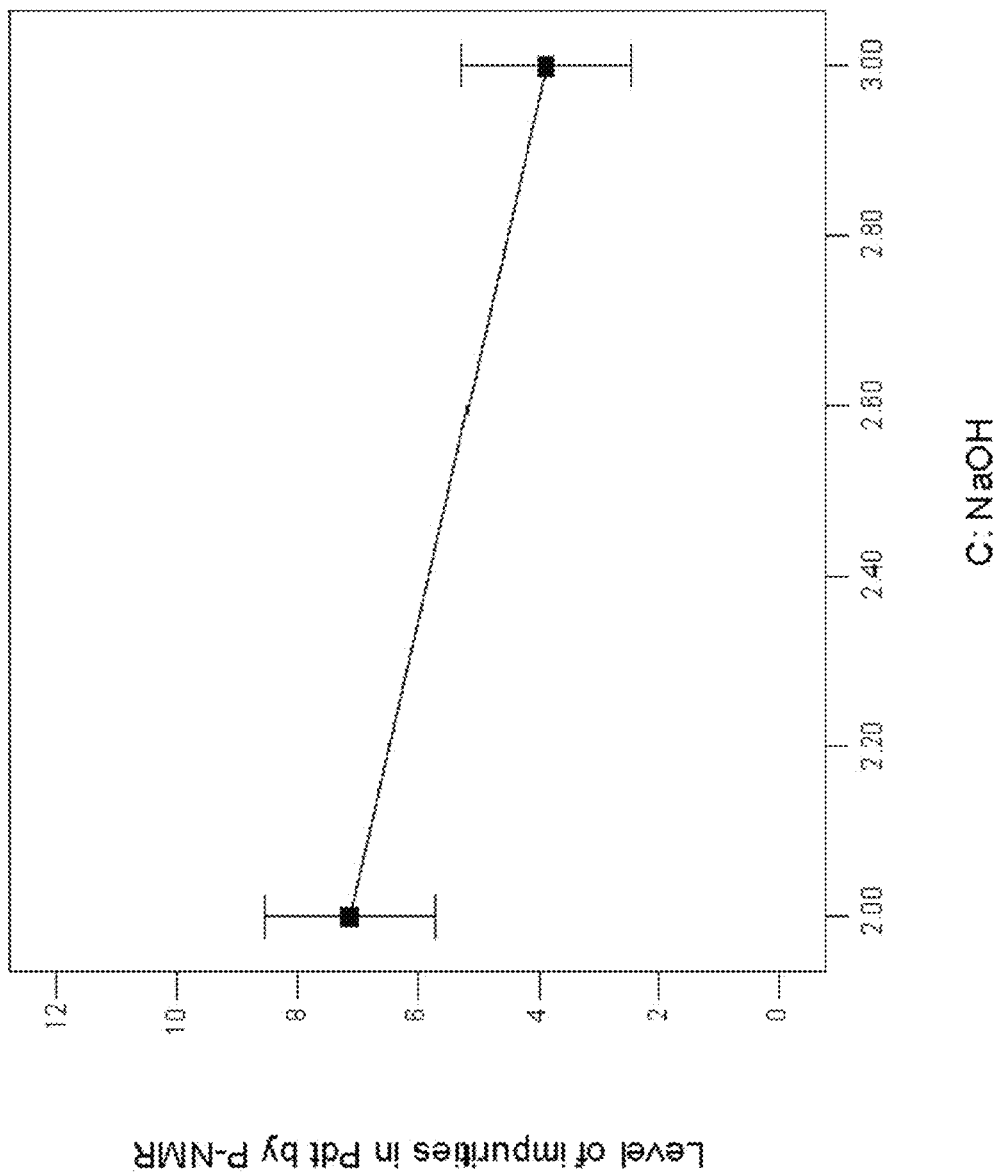

FIG. 19 shows a graph depicting the negative effect of NaOH on the level of impurities in the reaction product as measured by Proton NMR.

Figure 20:
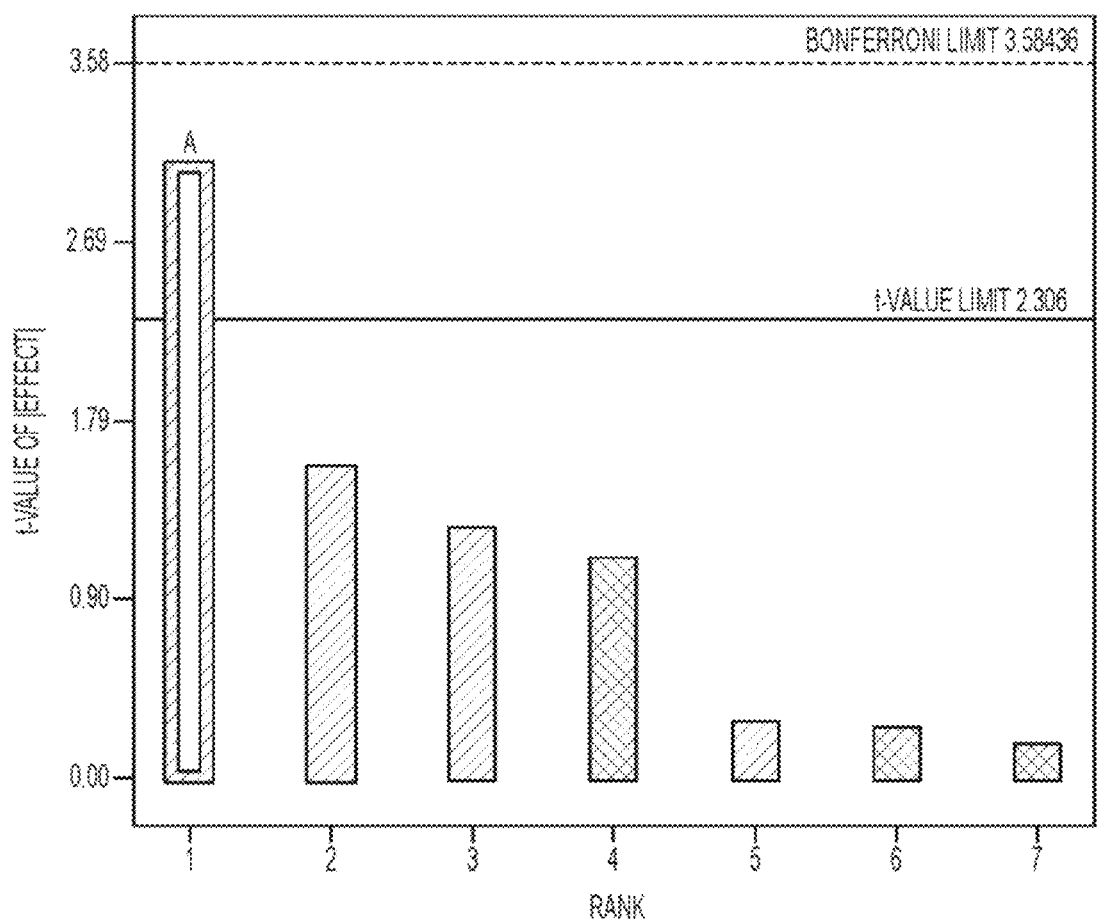

FIG. 20 shows a Pareto chart showing the effects on percentage of impurity Rx103 in the reaction product as measured by HPLC.

Figure 21:
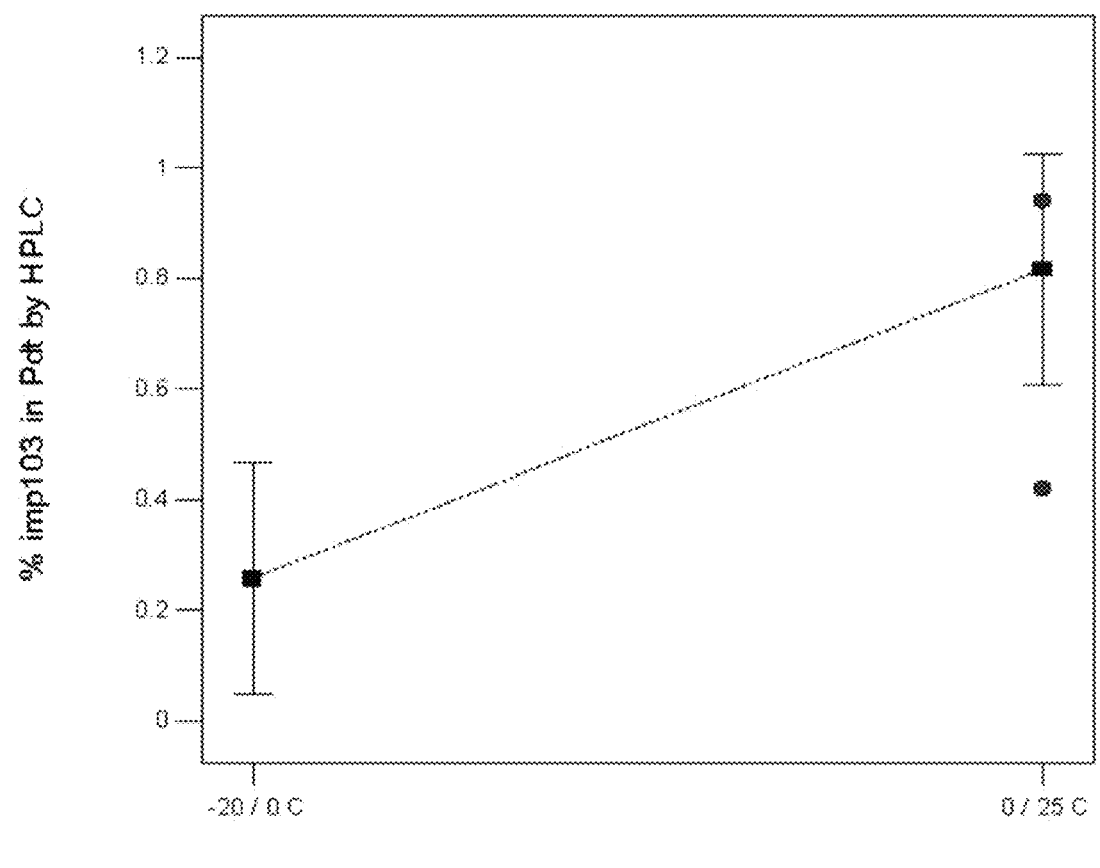

FIG. 21 shows a graph depicting the negative effect of temperature on percentage of impurity Rx103 (trans isomer of Rx100) in the reaction product as measured by HPLC.

Figure 22:
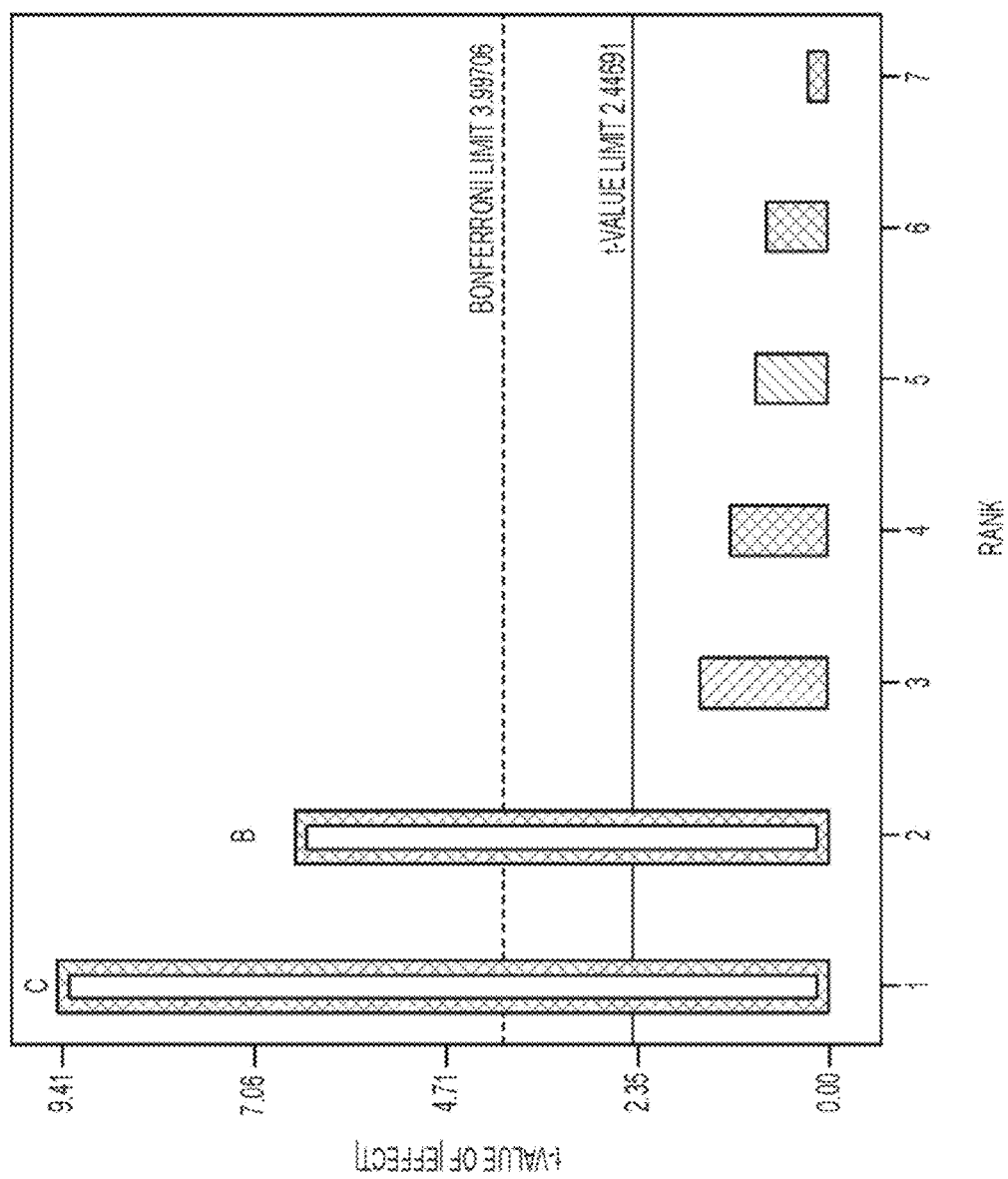

FIG. 22 shows a Pareto chart showing the effects on the percentage of impurity 50 in the reaction product as measured by HPLC.

Figure 23:
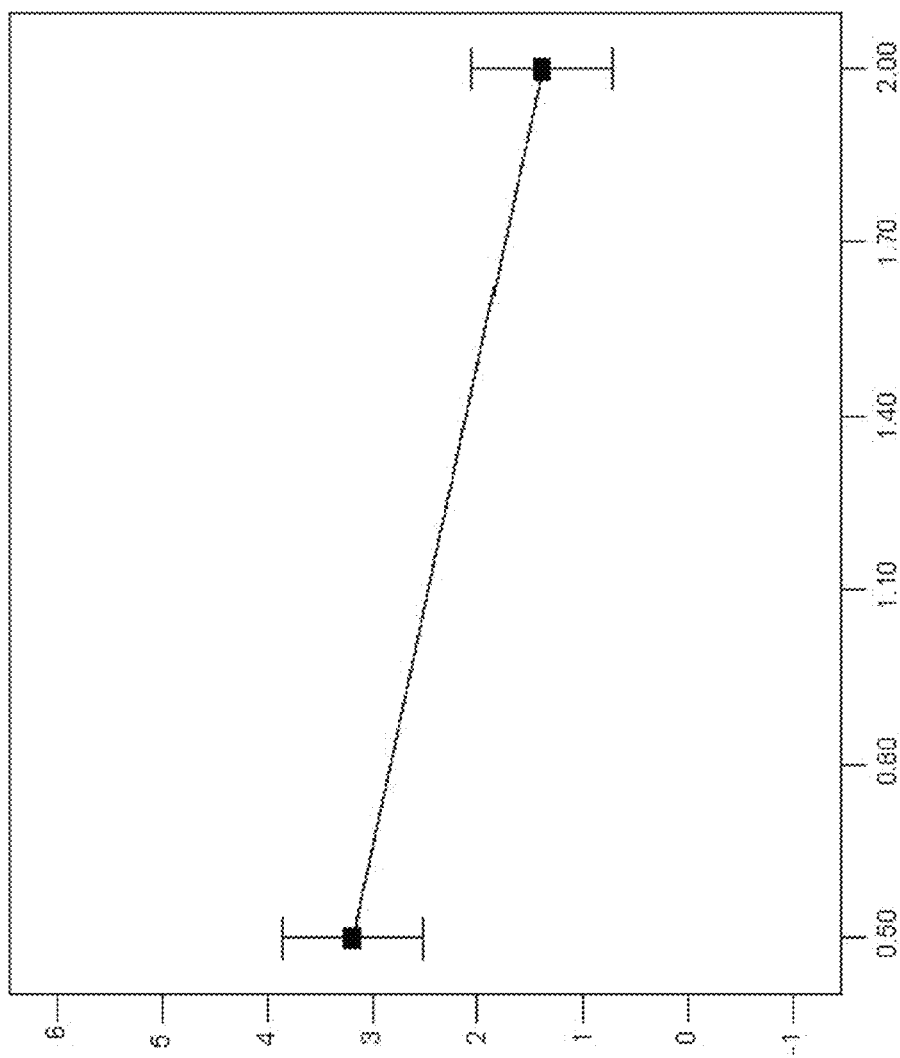

FIG. 23 shows a graph depicting the negative effect of TEA on the percentage of impurity 50 in the reaction product as measured by HPLC.

Figure 24:
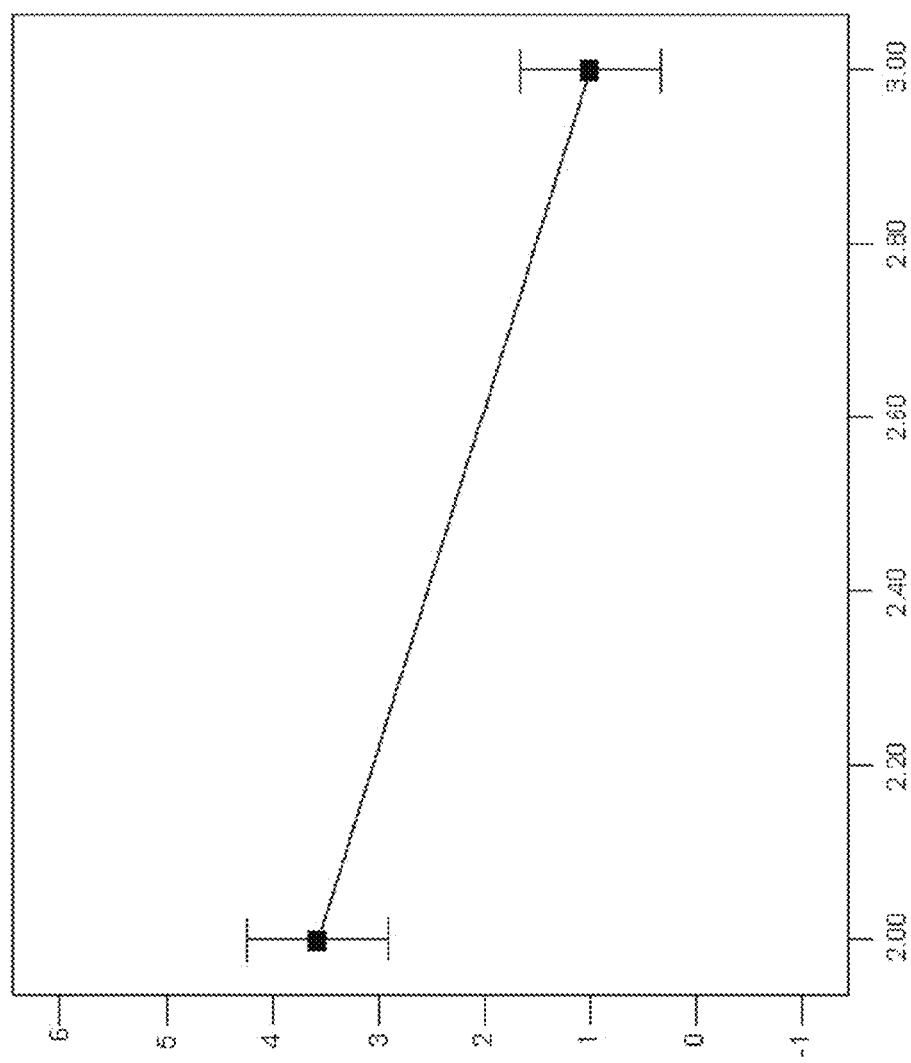

FIG. 24 shows a graph depicting the negative effect of NaOH on the percentage of impurity 50 in the reaction product as measured by HPLC.

Figure 25:
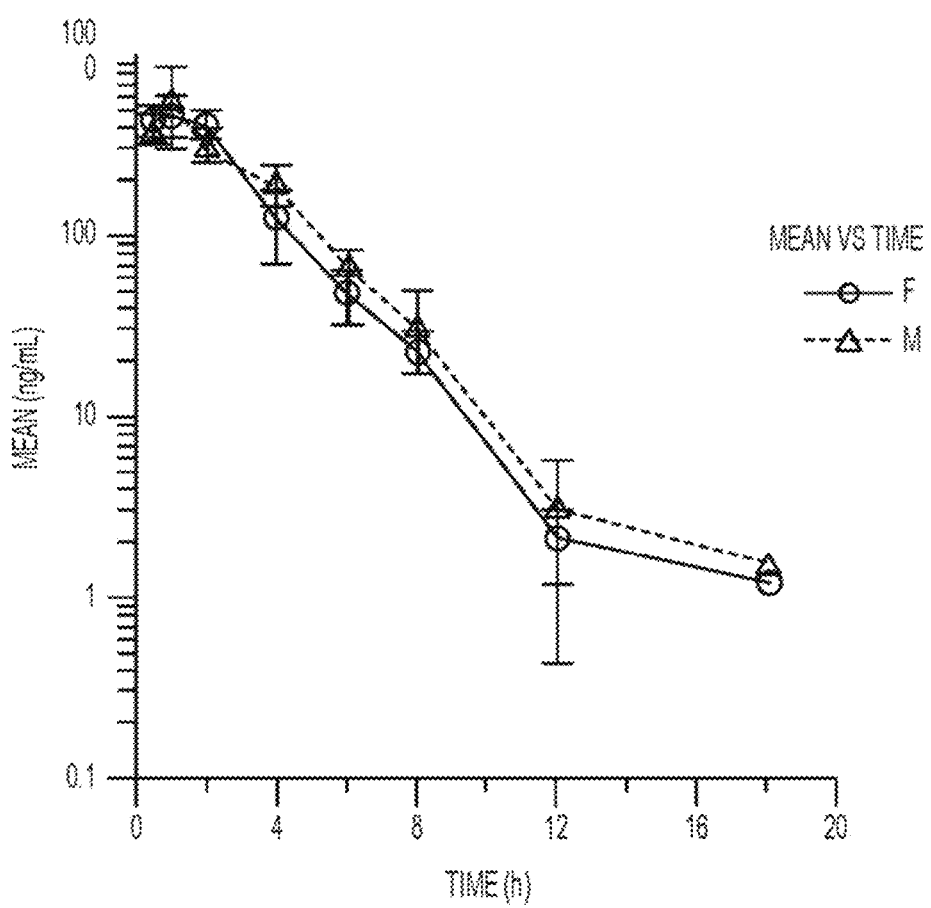

FIG. 25 shows a graph depicting the concentration vs. time profile following a single subcutaneous dose (1 mg/kg) of Rx100.Lysine in healthy mice.

Figure 26:
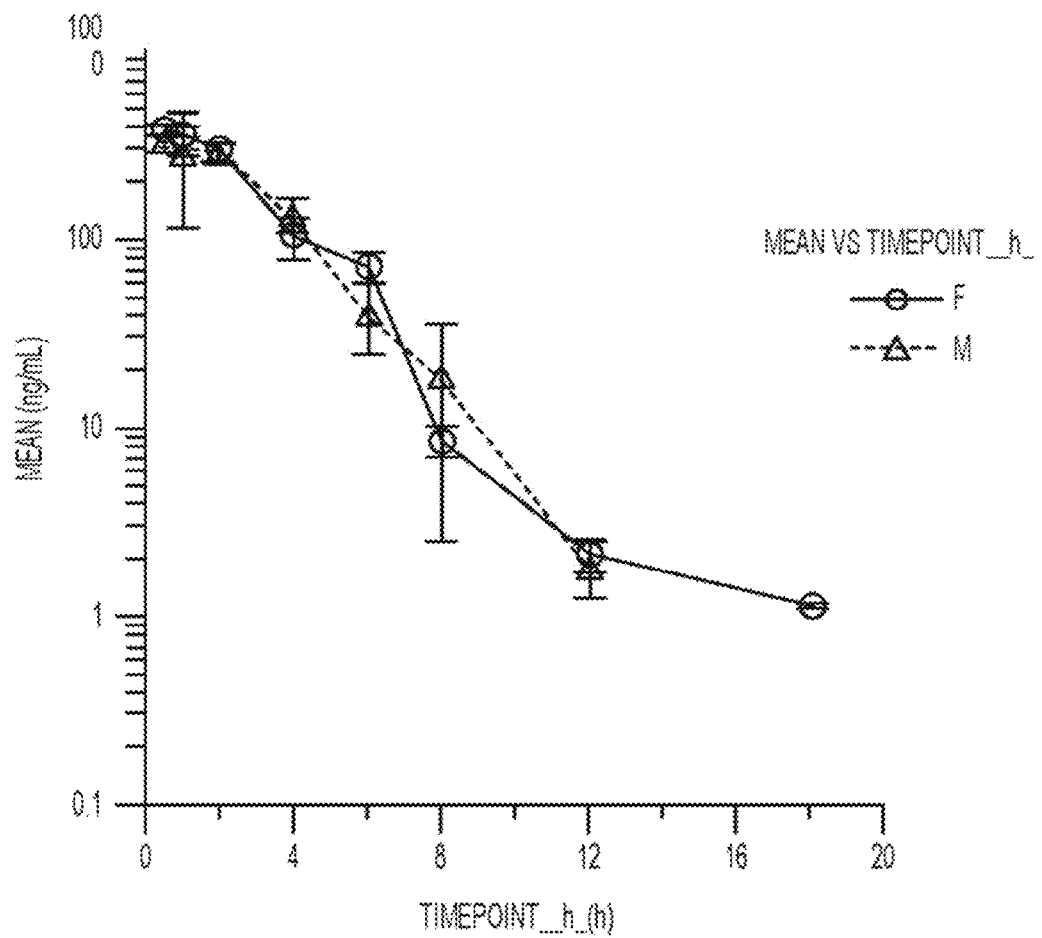

FIG. 26 shows a graph depicting the concentration vs. time profile following a single subcutaneous dose (1 mg/kg) of Rx100.Lysine in irradiated mice.

Figure 27:
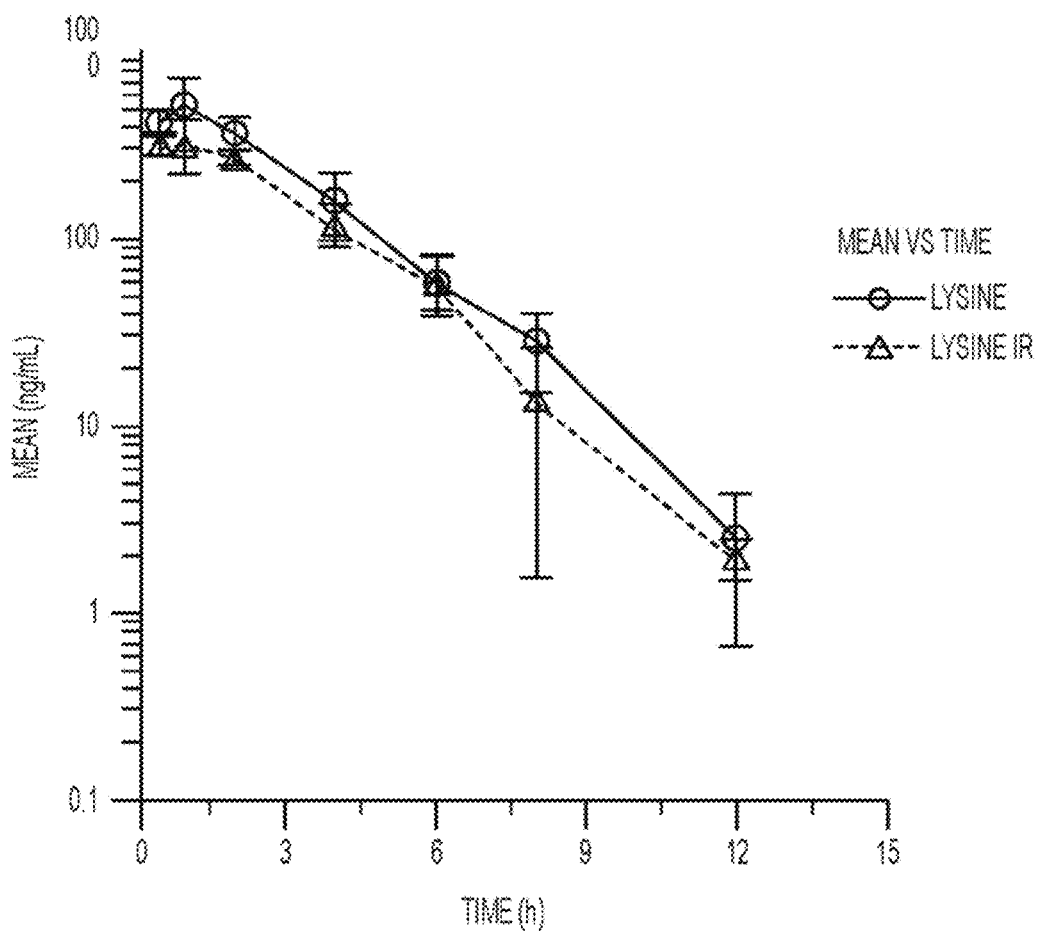

FIG. 27 shows a graph depicting the concentration vs. time profile following a single subcutaneous dose (1 mg/kg) of Rx100.Lysine in mice with or without irradiation.

Figure 28:
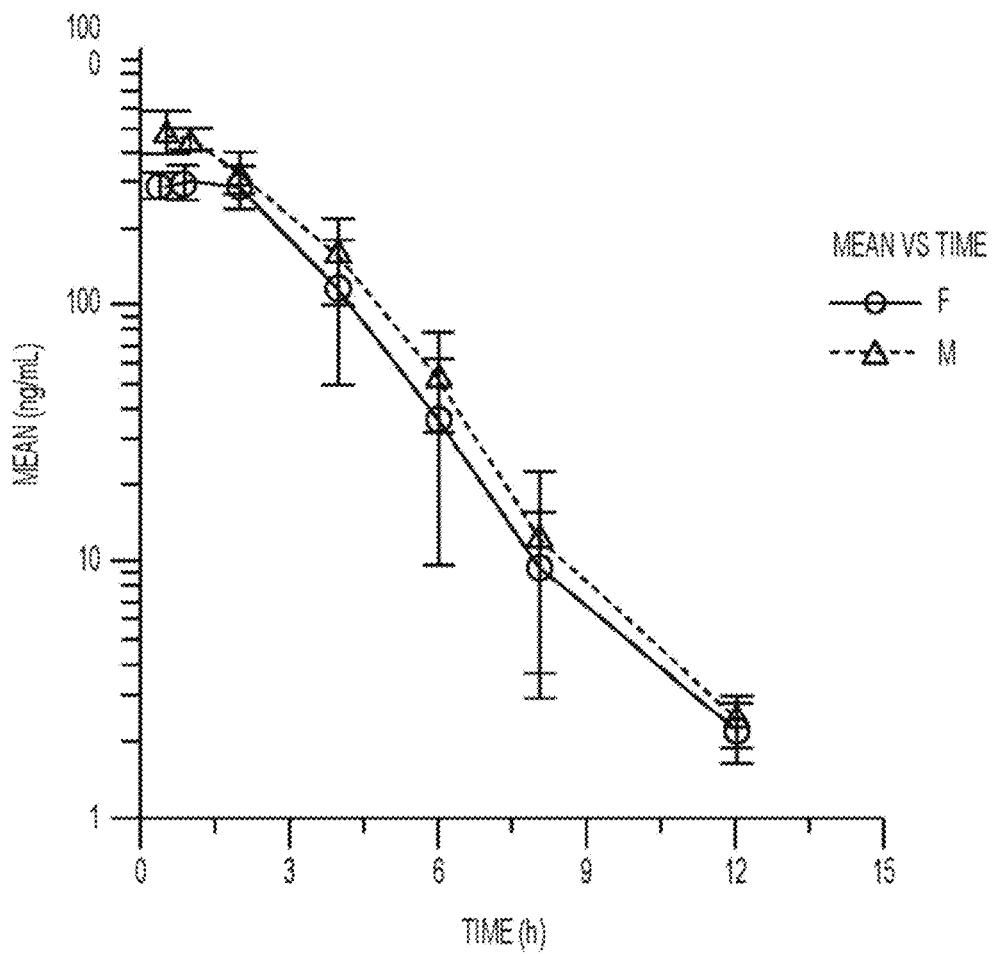

FIG. 28 shows a graph depicting the concentration vs. time profile following a single subcutaneous dose (1 mg/kg) of Rx100.Ammonia in healthy mice.

Figure 29:
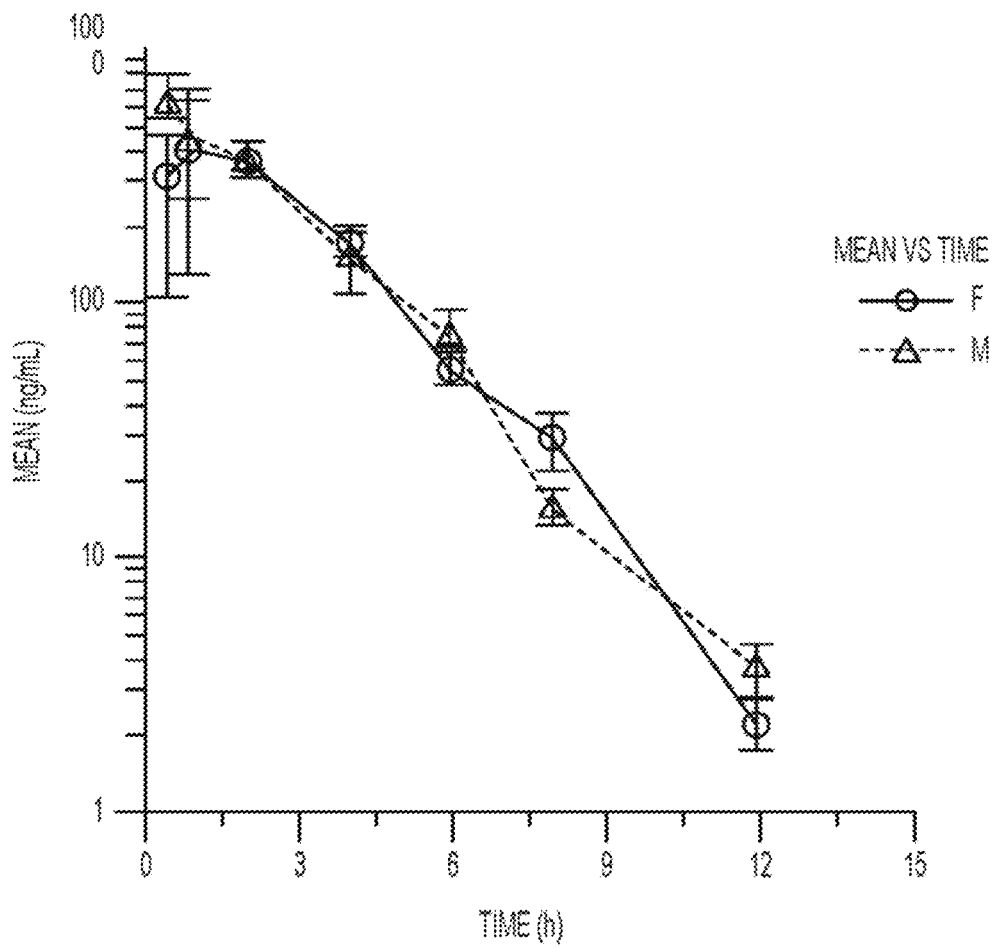

FIG. 29 shows a graph depicting the concentration vs. time profile following a single subcutaneous dose (1 mg/kg) of Rx100.Ammonia in irradiated mice.

Figure 30:
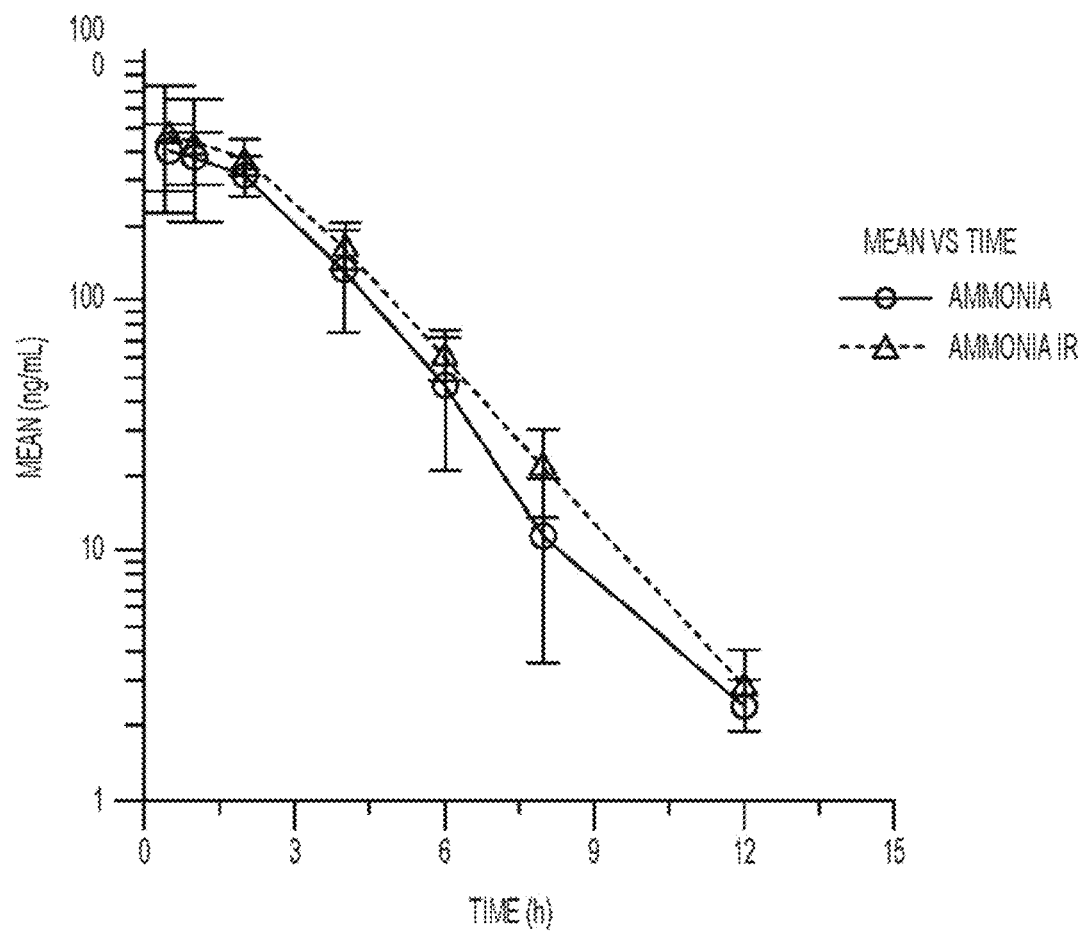

FIG. 30 shows a graph depicting the concentration vs. time profile following a single subcutaneous dose (1 mg/kg) of Rx100.Ammonia in mice with or without irradiation.

Figure 31:
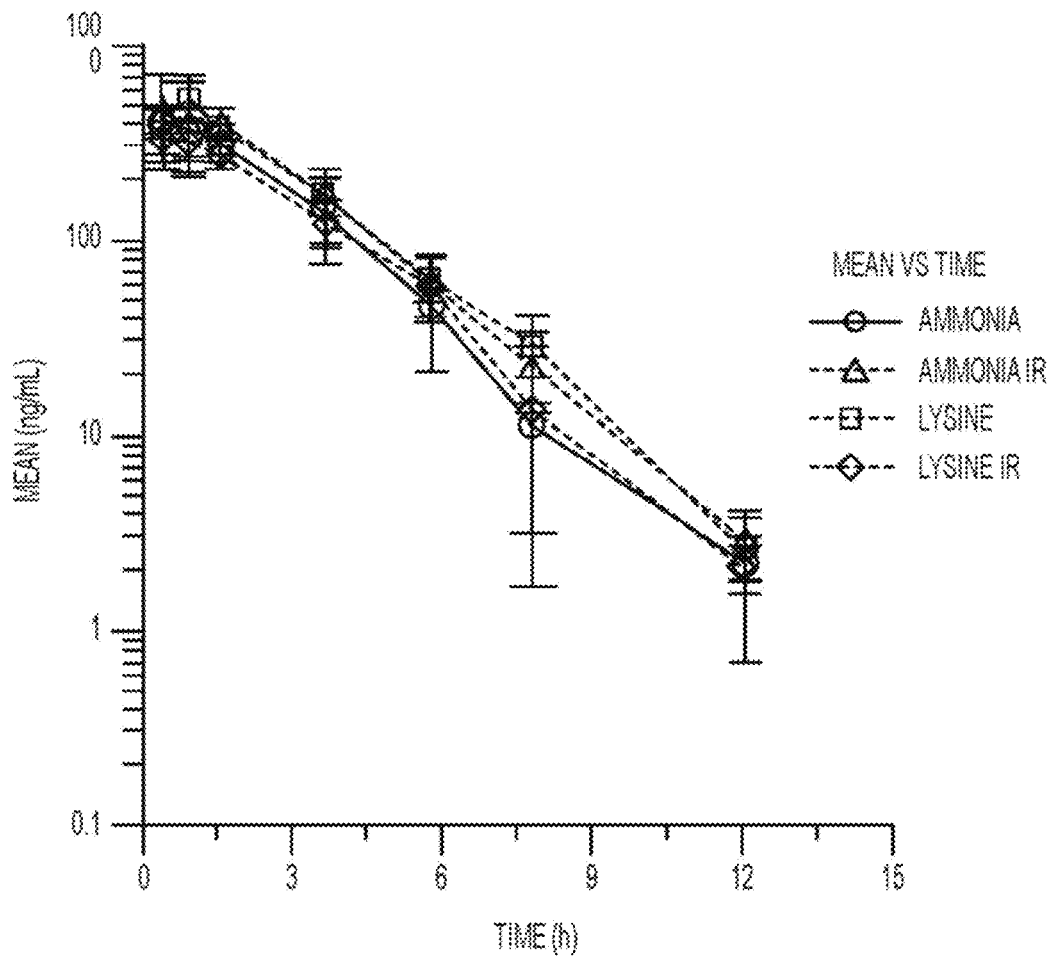

FIG. 31 shows a graph depicting concentration vs. time profiles of Rx100.Ammonia and Rx100.Lysine in healthy and irradiated mice.

Figure 32:
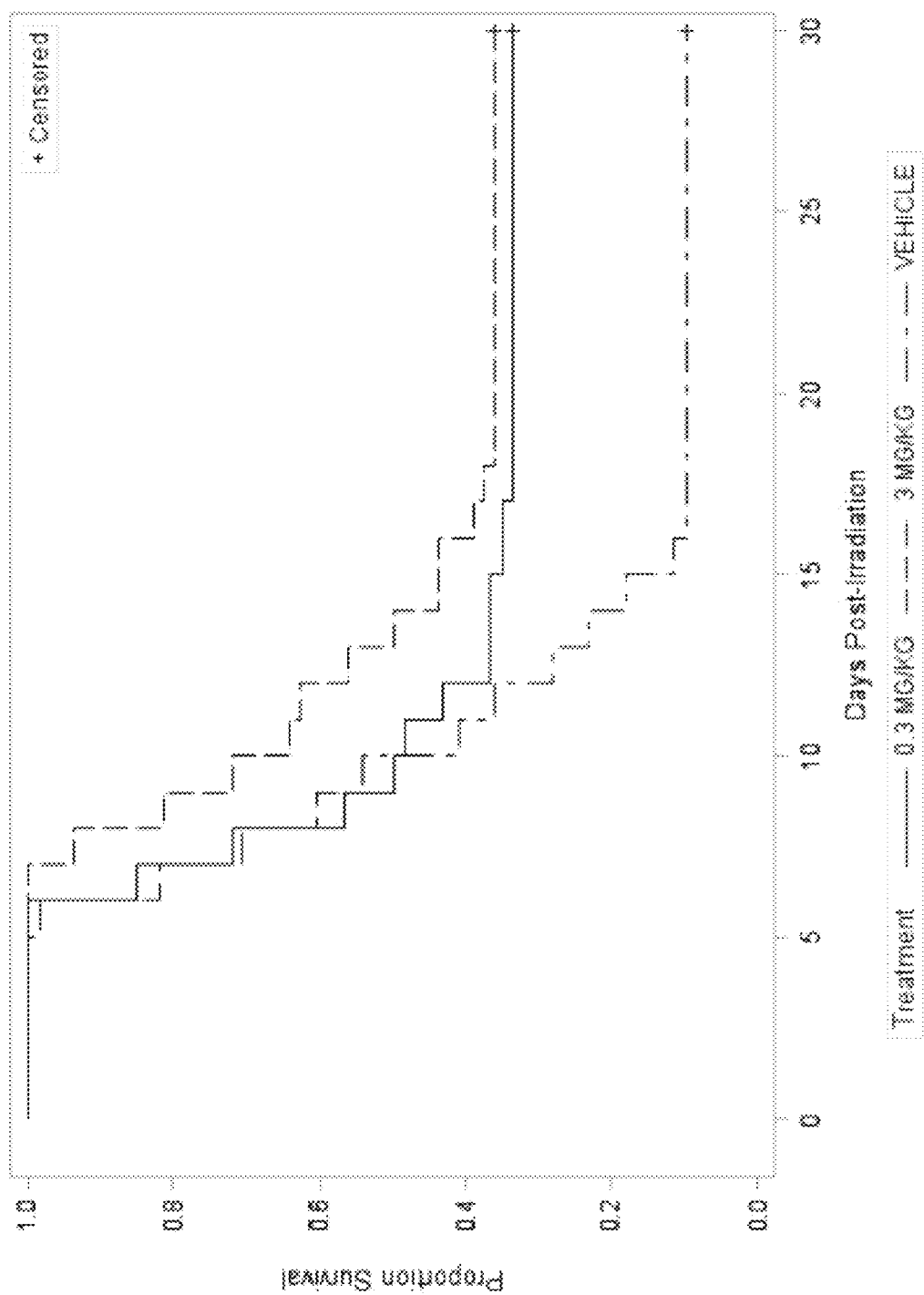

FIG. 32 shows a graph depicting Kaplan-Meier survival curves for females with treatment administered starting at 24 hours after radiation, which shows statistically significant effect of Rx100 on survival (p<0.0001 by log rank). Day 10 survival for Rx100 treated females was 56.3% as compared to 6.3% for vehicle (p<0.00001 by Chi Square). In the comparable group, both Rx100-treated and vehicle-treated male mice had 72% survival (data not shown) making assessment of drug effect in this more radio-resistant gender more difficult.

Figure 33:
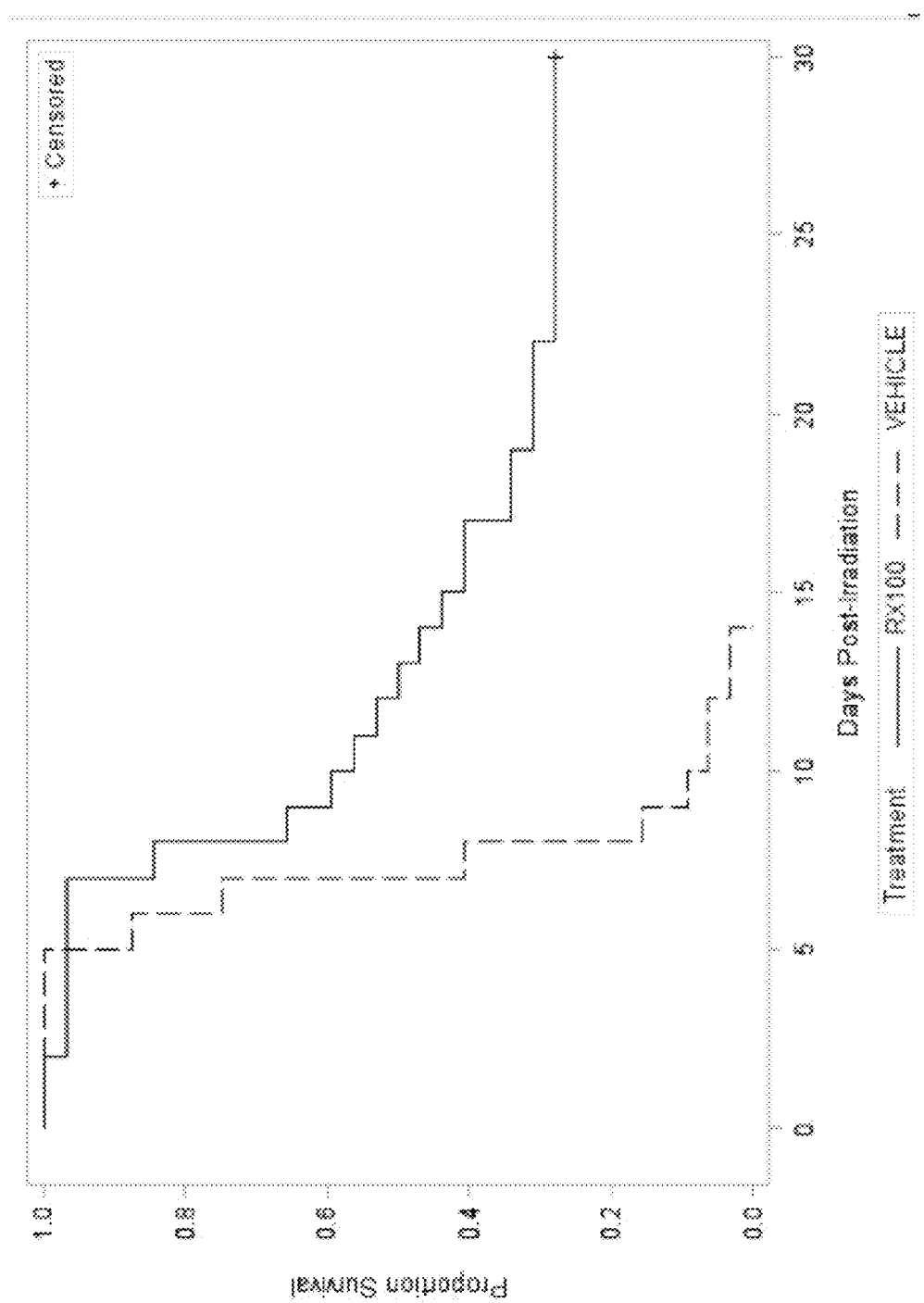

FIG. 33 shows a graph depicting Kaplan-Meier survival curves for females with treatment administered starting at 24 hours after radiation, which shows statistically significant effect of Rx100 on survival (p<0.0001 by log rank). Day 10 survival for Rx100 treated females was 56.3% as compared to 6.3% for vehicle (p<0.00001 by Chi Square). In the comparable group, both Rx100-treated and vehicle-treated male mice had 72% survival (data not shown) making assessment of drug effect in this more radio-resistant gender more difficult.

Figure 34A:
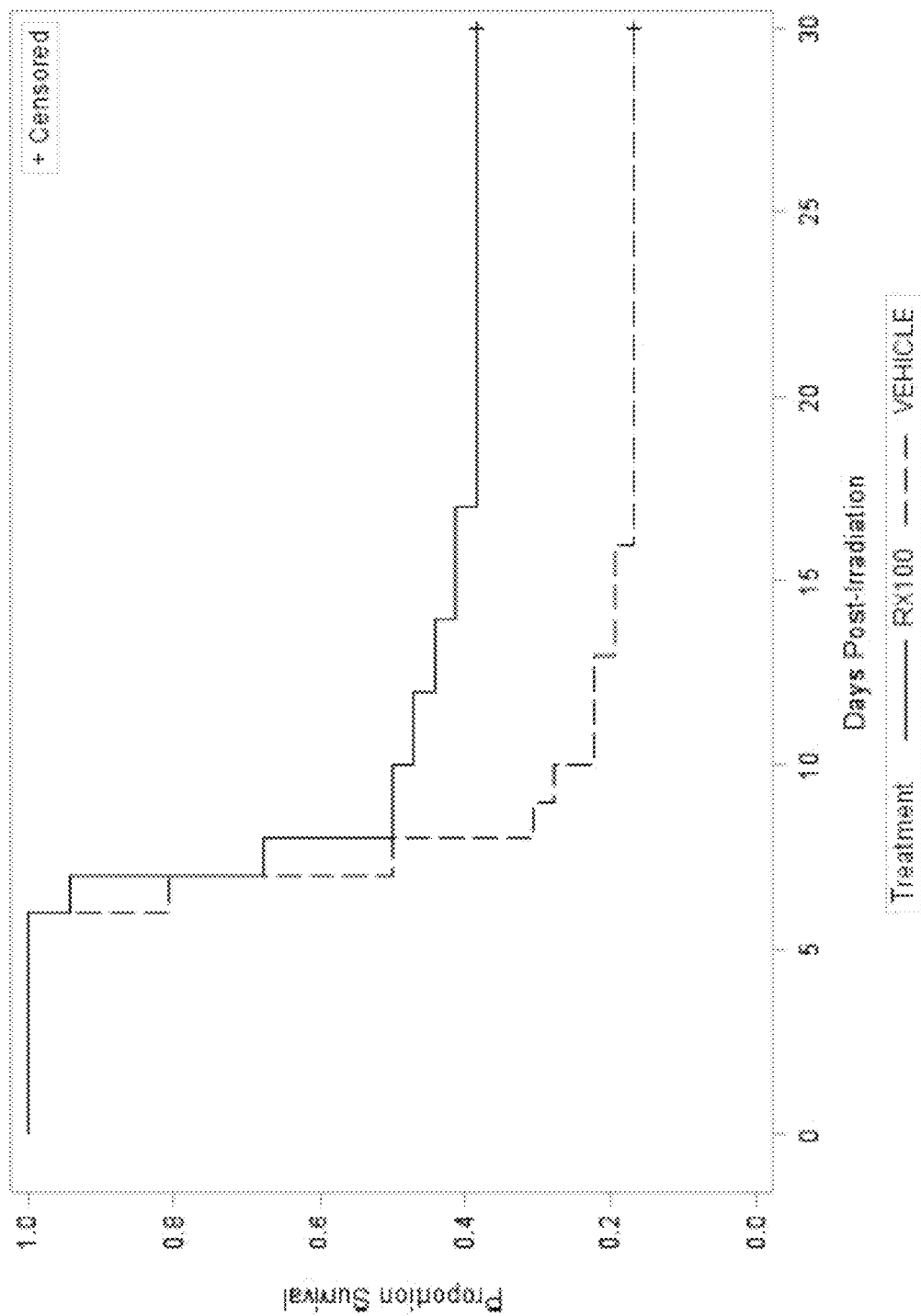
Figure 34B:
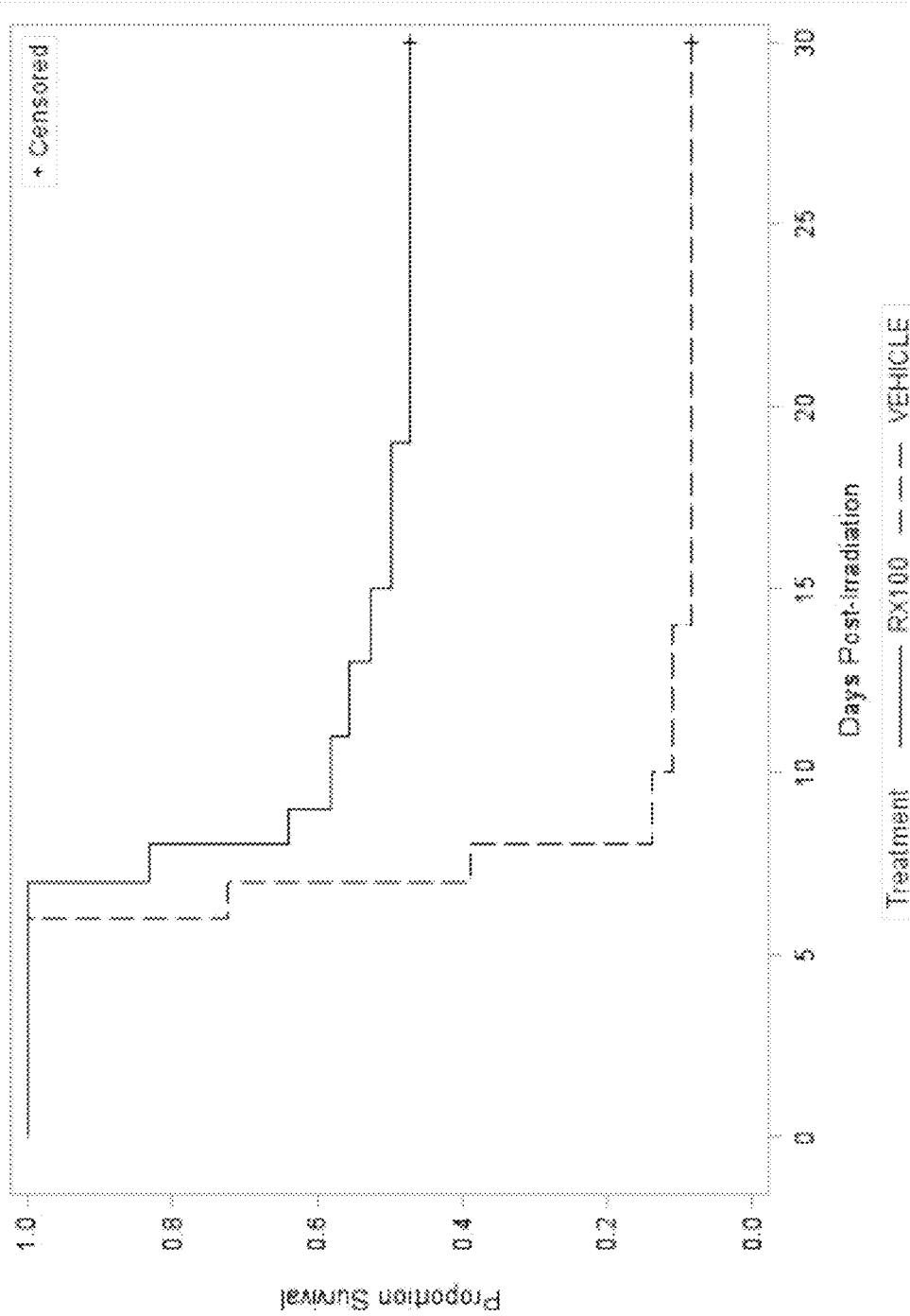
Figure 34C:
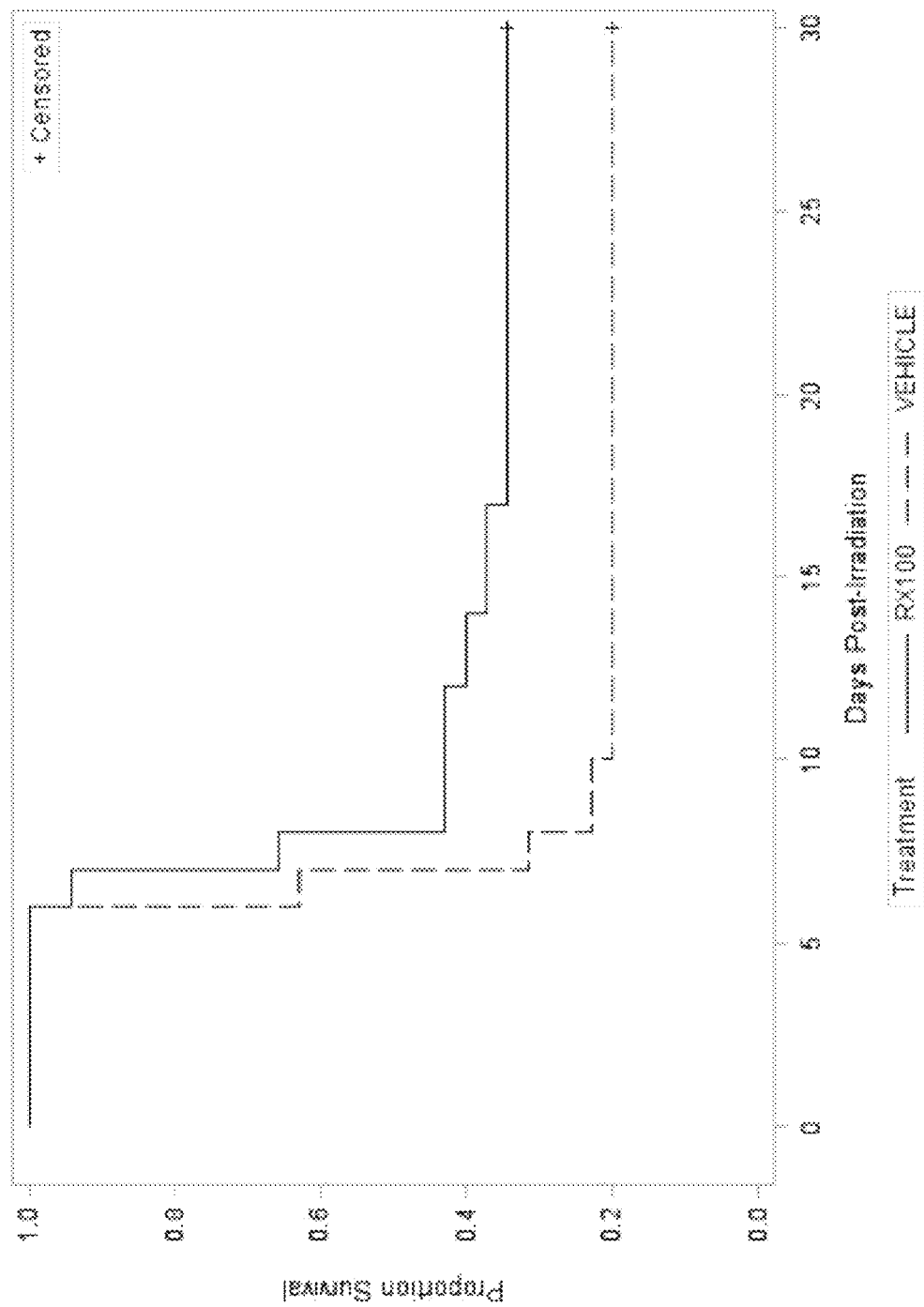

FIGS. 34A, 34B and 34C show graphs depicting Kaplan Meier Survival Curves for Study 4.1.8, which show a statistically increased mean survival time for all test agent as compared to vehicle arms by the log rank test at 15.55 Gy p=0.0236, 15.62 Gy p<0.0001, and 15.67 Gy p=0.0150, respectively.

Figure 35:
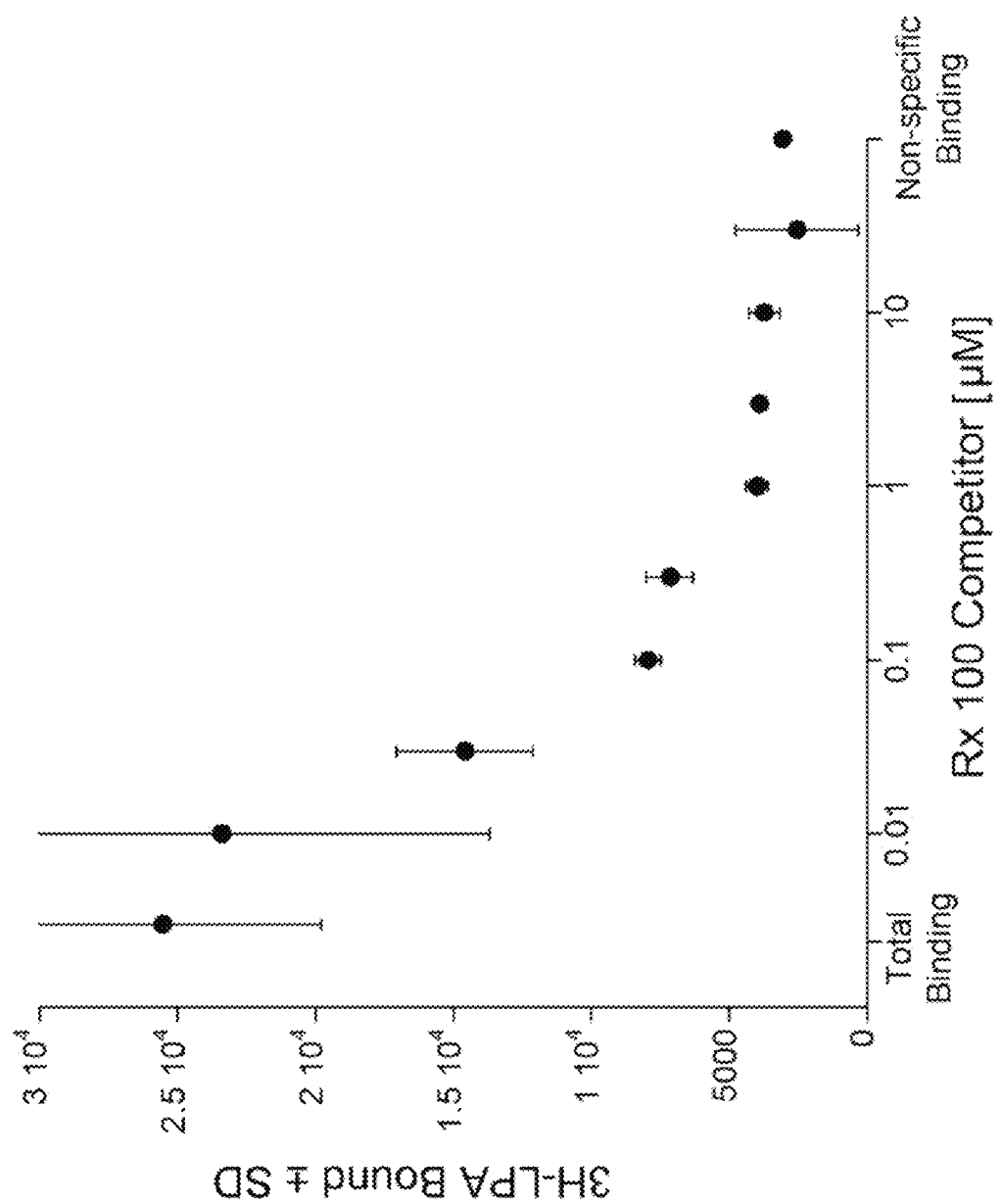

FIG. 35 shows a graph depicting the competitive binding of Rx100 to LPAR2.

Figure 36:
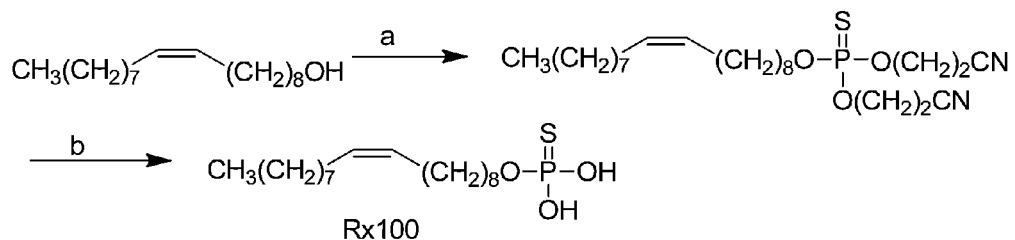

FIG. 36 shows a diagram designated as Scheme I.

Figure 37:
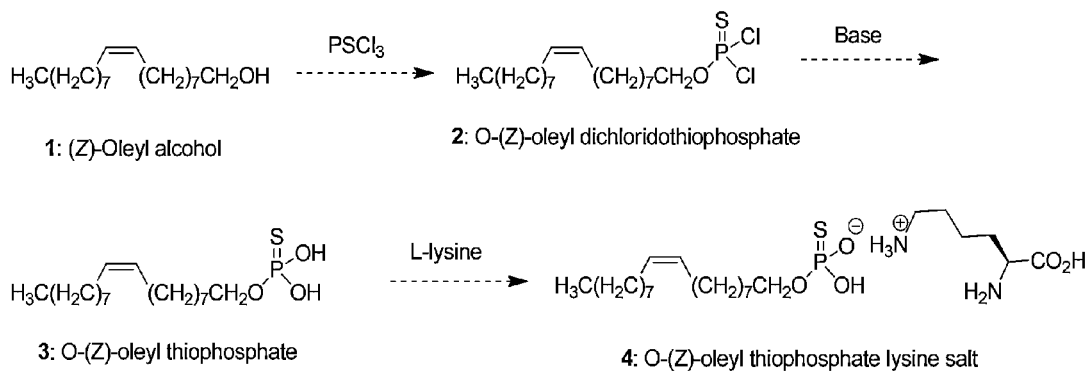

FIG. 37 shows a diagram designated as Scheme II.

Figure 38:
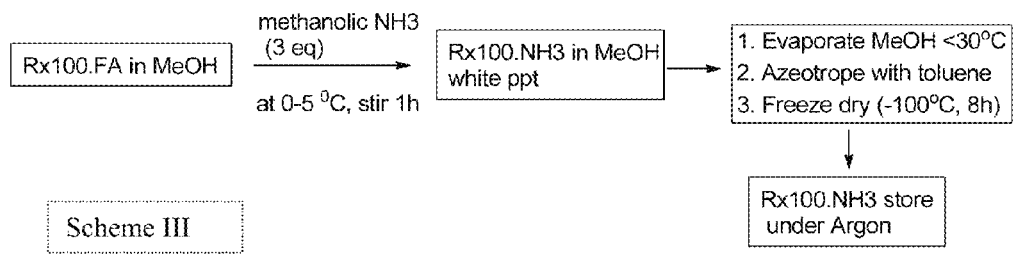

FIG. 38 shows a diagram designated as Scheme III.

Figure 39:
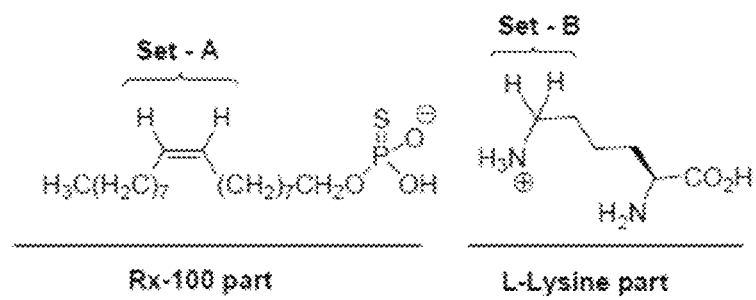

FIG. 39 shows a molecular scheme of RX100 L-lysine salt.

Figure 40:
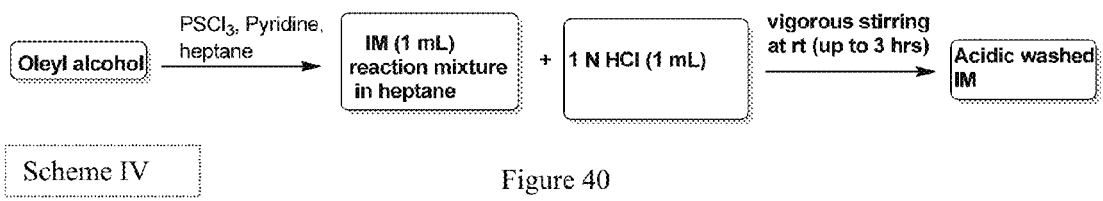

FIG. 40 shows a diagram designated as Scheme IV.

Figure 41:
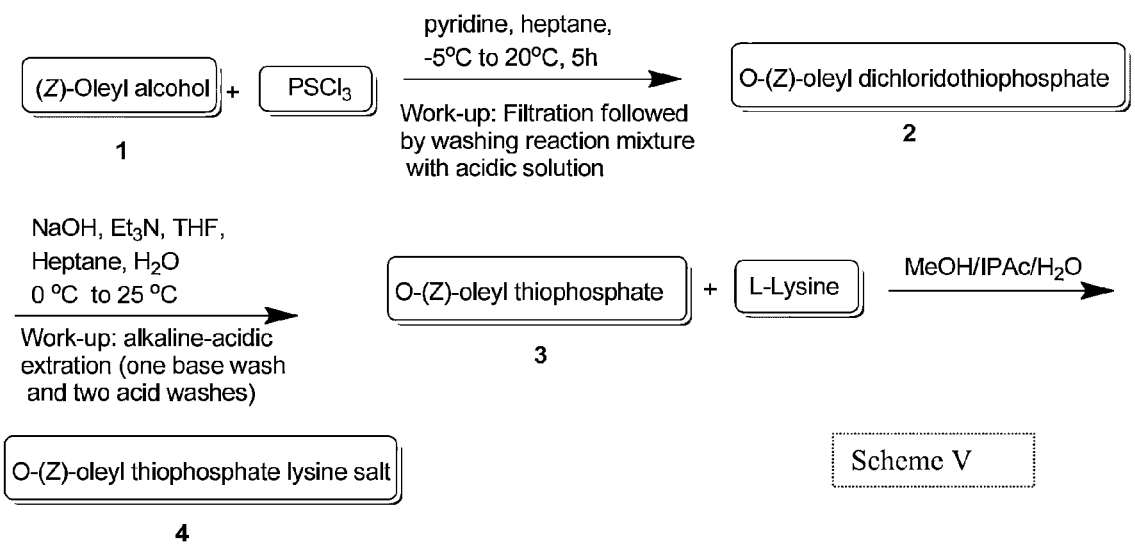

FIG. 41 shows a diagram designated as Scheme V.

DETAILED DESCRIPTION OF THE INVENTION

The present invention is partly based on the surprising discovery that Rx100.FA is able to form filterable crystalline or semi-crystalline salts with L-lysine base and that the Rx100.L-Lysine salt displays desirable features including, but not limited to, solubility, stability, scalability, absorbability, and functionality. Rx100.L-Lysine is used herein interchangeably with Rx100.Lysine, both of which refer to Rx100.L-Lysine crystalline or semi-crystalline salt disclosed in the present application.

Rx100 Crystalline Salts

In one aspect, the invention is directed to a crystalline or semi-crystalline salt form of Rx100 with a base addition. In some embodiments, the base addition is a L-lysine addition and the crystalline salt may be a mono-L-lysine salt, i.e., 1.0 molar equivalent of L-lysine is used in the reaction with Rx100.FA to make the salt. In other embodiments, the crystalline salt may be a sesqui-L-lysine salt, i.e., 1.5 molar equivalent of L-lysine is used in the reaction with Rx100.FA to make the salt. In further embodiments, the crystalline salt may be a di-L-lysine salt, i.e., 2.0 or more than 2.0 molar equivalent of L-lysine is used in the reaction with Rx100.FA to make the salt. As used herein, the term crystalline refers to any solid that has a short or long range order of the molecules, atoms or ions in a fixed lattice arrangement.

In some embodiments, Rx100 crystalline salts herein disclosed may be in different crystal forms, for example, in a triclinic, monoclinic, orthorhombic, tetragonal, rhombohedral, hexagonal or cubic crystal form, or a combination thereof. In other embodiments, crystalline salts herein disclosed may be in needle form, in thin flake or flake fragment form, or a combination thereof. In still other embodiments, the crystalline salts herein disclosed may be a semi-crystalline salt.

In some embodiments, Rx100 crystalline salts herein disclosed may be in a single form and substantially free of other forms, e.g., free of amorphous or other crystal forms. The term "substantially free" of other crystal forms refer to less than about 10 wt. % (weight percentage), preferably less than about 5 wt. %, more preferably less than about 3 wt. %, still preferably less than about 2 wt. %, still preferably less than about 1 wt. %, still preferably less than about 0.1 wt. %, most preferably less than about 0.01 wt. % of other crystal forms, e.g., amorphous or other crystal forms.

In other embodiments, Rx100 salts herein disclosed is a semi-crystalline salt, which may contain salt forms other than the crystal form. In these semi-crystalline salt forms, the salt may constitute more than 40 wt. %, preferably more than 50%, more preferably more than 60%, still more preferably more than 70%, still more preferably more than 80%, still more preferably more than 90%, and further more preferably more than 95% of crystal form.

In some embodiments, Rx100 crystalline salts herein disclosed are in dry form and substantially free from water, e.g., less than about 10 wt. %, preferably less than about 5 wt. %, more preferably less than about 3 wt. %, still preferably less than about 2 wt. %, still preferably less than about 1 wt. %, still preferably less than about 0.1 wt. %, most preferably less than about 0.01 wt. % of water. In some instance, the content of water is about 1.2 wt. %.

The crystallinity, the morphology, and/or purity of Rx100 crystalline salts herein disclosed may be determined by a number of methods, including, but not limited to, X-ray powder diffraction (XRPD), optical microscopy, Karl Fischer, differential scanning calorimetry (DSC), thermogravimetric analysis (TGA), dynamic vapor sorption (DVS), infrared adsorption spectroscopy (IR), proton ($^1$H) NMR spectroscopy, $^{31}$P NMR spectroscopy, $^{13}$C NMR spectroscopy, electrospray ionization, and HPLC-CAD. Characterization of solvates or hydrates or lack thereof may also be determined by DSC and/or TGA.

In some embodiments of Rx100 sesqui-L-lysine salt, for example, XRPD analysis may reveal that the sesqui-salt to be crystalline or be partially crystalline. This crystallinity may be confirmed with exhibition of birefringence under optical microscopy. In addition, moisture sorption analysis may show that Rx100 crystalline sesqui-L-lysine salt is hygroscopic, reversibly adsorbing 20.6% water at 95% RH and that hysteresis may be observed upon desorption as the solid salt is able to lose the gained moisture, with <3% residual water content. Further, thermal analysis of Rx100 crystalline sesqui-L-lysine salt by DSC may show multiple endothermic transitions, and TGA analysis of Rx100 crystalline sesqui-L-lysine salt may show a small weight loss likely attributed to the loss of water or solvent from 45-155° C. Moisture content may be confirmed by Karl Fischer analysis which may show the material to contain approximately 1.8 wt % water. Still further analysis by $^1$H NMR of Rx100 sesqui-L-lysine salt may show the starting material to be consistent with the structure of Rx100 with 1.5 eq. L-Lysine.

In some embodiments, Rx100.L-Lysine salt as disclosed herein may exhibit: (i) a $^1$H NMR (D$_2$O, 400 MHz) pattern as follows: 5.26 (m, 2H), 3.66-3.74 (m, 4H), 2.93 (t, J=8 Hz, 3H), 1.94 (m, 4H), 1.81 (m, 4H), 1.62 (m, 4H), 1.3-1.6 (m, 4H), 1.19-1.3 (m, 22H), and 0.77 (t, J=8 Hz, 3H); (ii) a product peak at δ46.60 in $^{31}$P NMR (D$_2$O, 400 MHz) analysis; (iii) a $^{13}$C NMR (D$_2$O, 125 MHz) pattern as follows: 174.85, 129.78, 129.50, 54.28, 38.86, 31.93, 29.89, 29.77, 29.63, 29.54, 29.39, 27.29, 27.17, 26.38, 25.94, 22.62, 21.41, and 13.88; (iv) an electrospray ionization (m/z) pattern as follows: 657.3 (for di salt, M+H$^+$) and 511.2 (for mono salt M+H$^+$); (v) an IR (cm$^{-1}$) pattern as follows: 2900, 2800, 1580, 1500, 1400, 1080, 1000, 800, 700, and 600; and/or (vi) an X-ray powder diffraction pattern substantially as herein set forth in Table 14 below.

In some embodiments, Rx100.L-Lysine salt is substantially pure as measured by HPLC-CAD analysis with a purity of, e.g., more than about 80%, preferably more than about 85%, more preferably more than about 90%, still preferably more than about 95%, and still preferably more than 98%.

In other embodiments, the purity of Rx100.L-Lysine salt is measured in terms of weight to weight percentage. As such, the Rx100.L-Lysine salt is pure with a weight to weight purity of, e.g., more than about 80%, preferably more than about 85%, more preferably more than about 90%, and still preferably more than about 95%.

In still other embodiments, the purity of Rx100.L-Lysine salt is measured by proton NMR analysis. As such, in some embodiments, no impurity may be detected in Rx100.L-Lysine salt.

In further embodiments, the impurity of Rx100.L-Lysine salt is measured by $^{31}$P NMR analysis. As such, the impurity of Rx100.L-Lysine salt shows less than about 1%, preferably less than about 0.5%, more preferably less than about 0.1%, still preferably less than about 0.05%, and still preferably less than about 0.02%.

In some further embodiments, as may be revealed by an abbreviated polymorph screening, e.g., with short term slurry, gravimetric solubility and evaporative crystallization experiments, Rx100 crystalline sesqui-L-lysine salt may show moderate to high solubility in most aqueous solvent systems but limited solubility in organic systems. Analysis by short term slurry and evaporative crystallization experiments may show that Rx100 crystalline sesqui-L-lysine salts do not change in form whether it is dissolved at 25° C. or 50° C.

Pharmaceutical Composition Comprising Rx100.L-Lysine Salts

In another aspect, the present invention is directed to a pharmaceutical composition that contains the Rx100.L-lysine salt. As used herein a "pharmaceutical composition" refers to a preparation of one or more of the active ingredients described herein, e.g., Rx100.L-lysine salt, with other chemical components such as physiologically suitable carriers and excipients. The purpose of a pharmaceutical composition may be to facilitate administration of a compound to an organism.

A pharmaceutically acceptable carrier may be a carrier, an adjuvant or a diluent that does not cause significant irritation to an organism and does not abrogate the biological activity and properties of the administered compound. An excipient may be an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Suitable routes of systemic administration of a pharmaceutical composition may, for example, include oral, rectal, transmucosal, transnasal, intestinal, or parenteral delivery such as intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections. Alternately, the pharmaceutical composition may be administered in a local rather than systemic manner, for example, via injection of the pharmaceutical composition directly into a tissue region of a patient.

Pharmaceutical compositions for use in accordance with the present invention may be formulated in conventional manners using one or more physiologically acceptable carriers comprising excipients and auxiliaries, which may facilitate processing of the active ingredients into preparations. Proper formulation is dependent upon the route of administration chosen.

For one example, when the route of administration is by injection, the active ingredients of the pharmaceutical composition may be formulated in aqueous solutions, preferably in physiologically compatible buffers such as L-histidine, Hank's solution, Ringer's solution, or physiological salt buffer, or any other comparable solutions, and may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing, emulsifying and/or dispersing agents.

For another example, when the administration is by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

In some embodiments, Rx100.L-Lysine is prepared in degassed aqueous (SWFI) 10 mM L-histidine for subcutaneous delivery as a parenteral drug product. USP grade L-histidine may be used in 10 mM concentration to serve as a buffer for the dissolved drug substance. The amount of active ingredients in solution (dosage strength) may vary from 0.075 mg/mL up to 20 mg/mL depending on intended uses. The solutions may be filled in pre-sterilized Nalgene bottles which were equipped with a pre-sterilized Nalgene screw cap. Polyethylene terephthalate copolyester, glycol modified (PETG) Nalgene bottles (30 mL) is available from Fisher Scientific (Catalog #03-311-1V). These bottles are sterile with low permeability for $O_2/CO_2$.

In other embodiments, the pharmaceutical composition Rx100.L-Lysine may be prepared as a lyophilized drug product whose composition is active ingredient Rx100.FA (10 mg/mL) in 5% Sucrose in 50 mM L-histidine Buffer adjusted to pH 6.5. As such, in some instances, the preparation may be adapted to a dual chamber lyophilized cartridge for insertion into a pen injector.

Pharmaceutical compositions suitable for use in the context of the present invention include compositions wherein the active ingredients are contained in an amount effective to achieve the intended purpose. More specifically, a therapeutically effective amount means an amount of active ingredients (Rx100.L-Lysine) effective to prevent, alleviate or ameliorate a medical condition, e.g., damage caused by radiation exposure.

In some embodiments, the pharmaceutical composition is intended for use in mitigation (post-exposure prophylaxis) of gastrointestinal acute radiation syndrome (GI-ARS) following exposure to potentially lethal ionizing radiation. GI-ARS results from radiation injury to the radiosensitive GI crypt stem cell (position 4-5). Stem cell division and then differentiation of half of the daughter cells results in growth of an intestinal villus. The intestinal villus contains absorptive cells and also provides a barrier to incorporation of toxins and loss of water. Within hours after irradiation, partially damaged stem cells (and stem cells subject to soluble factors from neighboring dying cells) enter mitotic arrest for the ensuing 6 to 24 hours. During arrest, a "decision" is made to enter an apoptotic pathway or proceed to repair and regeneration. Small intestinal stem cells are radiosensitive which may be an expression of a preference to enter an apoptotic pathway. Thus, the small gut loses its capacity for regeneration of the villous. The villous undergoes collapse at approximately 3 days post irradiation with resultant diarrhea, dehydration, inability to absorb nutrients, bacterial translocation and death from dehydration. If there is concomitant loss of bone marrow and leukocyte function, with immunosuppression, sepsis from bacterial translocation may ensue. Death generally occurs within 10 days. Based on several nuclear detonation and radiation exposure events (e.g., Chernobyl, Goiania, Bikini Atoll), radiation doses necessary to produce GI-ARS have been substantially higher (>8 Gray, hereinafter, Gy) than those that produce immediate loss of lymphocytes (also to apoptosis) and loss of three lineage precursors in the bone marrow, i.e., platelets and red and white cells (<9 Gy). As disclosed herein, Rx100 protects from and mitigates? GI-ARS by activating the transmembrane G protein-coupled lysophosphatidic acid receptors (LPAR) and, more specifically, the LPAR2 subtype. LPAR2 activation leads to a cascade of intracellular events that switch cells from an apoptotic to a repair/regenerative pathway.

Determination of a therapeutically effective amount is well within the capability of those skilled in the art in light of the detailed disclosure provided herein. For example, the therapeutically effective amount or dose can be estimated initially from in vitro and cell culture assays. For another example, an effective dose may be formulated in animal models to achieve a desired concentration or titer. Such information can be used to more accurately determine useful doses in humans.

Toxicity of the active ingredients described herein may be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Dosage amount and interval may be adjusted individually to blood levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations. Depending on the severity and responsiveness of the condition to be treated, dosing can be of a single or a plurality of administrations, with course of treatment lasting from several days to several weeks or until cure is effected or diminution of the disease state is achieved. The amount of a composition to be administered will, of course, be dependent on, for example, the subject being treated, the severity of the affliction, the manner of administration, and the judgment of the prescribing physician.

For example, in some embodiments, the pharmaceutically effective amount of Rx100. L-lysine salt may be as low as about 0.02 mg/kg/day to about 0.03 mg/kg/day in human, and as high as about 2 mg/kg/day to about 3 mg/kg/day. In still some embodiments, the effective amount may be higher than 3 mg/kg/day as the radiation damage becomes more severe.

In some embodiments, the dosage and administration schedule also depend on the gender of the human subject to be treated. In some instances, some female patients may be more prone to radiation damage and therefore, dosage may be smaller and administration schedule may be less frequent than male patients. In other instances, some female patients may be more prone to radiation damage and therefore, dosage may be smaller and administration schedule may be less frequent than female patients.

In some embodiments, the administration may preferably start within 24 hours after radiation exposure, within 48 hours after radiation exposure, or within 72 hours after radiation exposure. The administration may be for a single dose in some instances. The administration may be for multiple doses, e.g., 2, 3, 4, 5, or 6 doses in other instances. The administration may continue as many times as a medical doctor considers necessary.

In other embodiments, the administration schedule and the dosage may be related. For one example, when the period between the first administration and the radiation event is short, e.g., within 1 hour, the dosage for each administration may be smaller than that where the first dose is administered 24 hours after the radiation event. For another example, when the administration is frequent, e.g., once every 12 hours, the dosage for each administration may be smaller than that where the administration is less frequent, e.g., once every 24 hours.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Methods of Making Rx100. L-Lysine Salt Form

In a further aspect, the present invention is directed to a method for producing Rx100. L-lysine crystalline salts. In some embodiments, the method comprises the steps of (i) mixing Rx100.FA with L-lysine, and (ii) allowing the Rx100.L-Lysine salt to form in the presence of a suitable solvent.

In the mixture, L-lysine base may be used at molar equivalents of 1.0, 1.5, 2.0 or 3.0 of the free acid, forming Rx100 crystalline salts as a sesqui-L-lysine salt, or di-L-lysine salt, respectively. In other embodiments, one and a half molar equivalent of L-lysine base is used to mix with Rx100.FA to allow Rx100 sesqui-L-lysine crystalline salt formation in the presence of a suitable solvent. In still other embodiments, two or three molar equivalent of L-lysine base is used to mix with Rx100.FA to allow Rx100 di-L-lysine crystalline salt formation in the presence of a suitable solvent.

The step of mixing Rx100.FA with L-lysine base may be carried out over a sufficient period of time. In some embodiments, the period of time can be about five minutes. The time that the mixing step takes may affect the reaction between the acid and the base and hence how crystalline salt forms. In other embodiments, the period of time may be further extended to allow the proper formation of crystalline salts as the scale of the production increases.

The mixing of Rx100.FA with L-lysine base may be carried out in either direction. In some embodiments, L-lysine is added to the Rx100.FA solution while being stirred at room temperature. In other embodiments, Rx100.FA is added to L-lysine solution while being stirred at room temperature.

In some embodiments, the starting material L-Lysine may be prepared in methanol and optionally filtered through a 0.2 μm filter. In addition, Rx100 may be prepared in methanol-IPAc mixture solution and optionally filtered through a 0.2 μm filter. Further, prepared L-Lysine solution is added to the prepared Rx100 solution in a drop-wise manner.

The solvent in which the Rx100.L-Lysine crystalline salts form may be methanol, Isopropyl alcohol (IPA), IPA:water (95:5 vol), tert-Butyl methyl ether (tBME), Ethyl acetate, IPA:water (1:1 vol), Diethyl ether, tetrahydrofuran, or a combination thereof. The amount of solvent for the reaction may vary from 3-20 volumes of the Rx100.FA, preferably between 5-8 volumes.

In some embodiments, the solvent is a mixture of methanol and water, or methanol, water, and IPAc. In some instances, the mixture of methanol, water, and IPAc is at a weight ratio of 10:2:1.5. In other embodiments, the solvent is a mixture of methanol and 10-50% IPAc, preferably 20-50% IPAc.

In still other embodiments, the solvent is methanol alone. The methanol may be about 5-20 molar equivalent, preferably about 12 molar equivalent of (Z)—O-octadec-9-en-1-yl O,O-dihydrogen phosphorothioate free acid.

In some embodiments, the crystalline salts form in the solvent in which the Rx100. free acid and L-lysine base are mixed. In these embodiments, the step of allowing the crystalline salt to form in the presence of a solvent may be carried out while the Rx100.FA and the L-lysine base are being mixed.

In contrast, in other embodiments, the solvent in which the Rx100.FA and L-lysine base are mixed is first depleted by, e.g., vacuum after the mixing step is carried out, and then a fresh solvent is added in the dried material so that crystalline salts form in the fresh solvent. In some instances, the fresh solvent may be the same solvent as the depleted solvent and the step of allowing the crystalline salt to form in the presence of a solvent may be carried out at the same time and after the Rx100.FA and the L-lysine base are mixed. In other instances, the fresh solvent may be a different solvent than the depleted solvent and the step of allowing the crystalline salt to form in the presence of a solvent may be carried out after the Rx100.FA and the L-lysine base are mixed.

In other embodiments, the method for producing Rx100.L-Lysine crystalline salts comprises the steps of (1) mixing Rx100.FA with L-lysine, (2) allowing the Rx100.L-Lysine crystalline salt to form in the presence of a solvent, and (3) filtering, washing and drying the Rx100.L-Lysine crystalline salt.

The action of filtering may be carried out by many filtering methods known in the art, for example, by using a filtering membrane. Here the filtering step would separate solids from those that can pass through a filtering membrane, thereby obtaining the crystalline salt formed in the solvent free of the solvent, extra starting materials (e.g., Rx100. FA and L-lysine base) and other contaminants.

The action of washing may be carried out by contacting a solvent with the filtered salt solid. The washing step would further get rid of any contaminants on the surface of the crystalline salt. The solvent used for washing may be methanol or other solvent of similar properties as a washing buffer.

The action of drying the washed crystalline salt may be carried out by many methods known in the art. For example, in some instances, the drying may be achieved at 35° C. under vacuum for about 1 hour. In other instance, the drying may be achieved at room temperature for about 12 hours or longer. A person skilled in the art would be able to find the right condition so that the washed crystalline salts may be dried properly by varying the temperature, the strength of the vacuum and the time period for the vacuum.

In some embodiments, the crystalline salts thus produced herein, e.g., Rx100.L-Lysine, are soluble in water. In other embodiments, the crystalline salts thus produced herein, e.g., Rx100.Ethylenediamine, are not as soluble in water but are more soluble in organic solvent.

In some embodiments, the Rx100.L-Lysine crystalline salts thus produced herein exhibits: (i) a $^1$H NMR ($D_2O$, 400 MHz) pattern as follows: 5.26 (m, 2H), 3.66-3.74 (m, 4H), 2.93 (t, J=8 Hz, 3H), 1.94 (m, 4H), 1.81 (m, 4H), 1.62 (m, 4H), 1.3-1.6 (m, 4H), 1.19-1.3 (m, 22H), and 0.77 (t, J=8 Hz, 3H); (ii) a product peak at δ46.60 in $^{31}$P NMR ($D_2O$, 400 MHz) analysis; (iii) a $^{13}$C NMR ($D_2O$, 125 MHz) pattern as follows: 174.85, 129.78, 129.50, 54.28, 38.86, 31.93, 29.89, 29.77, 29.63, 29.54, 29.39, 27.29, 27.17, 26.38, 25.94, 22.62, 21.41, and 13.88; (iv) an electrospray ionization (m/z) pattern as follows: 657.3 (for di salt, M+H$^+$) and 511.2 (for mono salt M+H$^+$); and/or an IR (cm$^{-1}$) pattern as follows: 2900, 2800, 1580, 1500, 1400, 1080, 1000, 800, 700, and 600.

In some embodiments, the Rx100.L-Lysine crystalline salts thus produced herein is substantially pure by HPLC-CAD analysis, e.g., more than about 80%, preferably more than about 85%, more preferably more than about 90%, still preferably more than about 95%, and still preferably more than 98%.

In other embodiments, the purity of the Rx100.L-Lysine crystalline salts thus produced herein is measured in terms of weight to weight percentage. As such, the Rx100.L.Lysine salt is pure e.g., more than about 80%, preferably more than about 85%, more preferably more than about 90%, and still preferably more than about 95%.

In still other embodiments, the purity of the Rx100.L-Lysine crystalline salts thus produced herein is measured by proton NMR analysis. As such, no impurity may be detected in Rx100.L-Lysine salt.

In further embodiments, the impurity of the Rx100.L-Lysine crystalline salts thus produced herein is measured by $^{31}$P NMR analysis. As such, the impurity of Rx100.L-Lysine crystalline salt shows less than about 1%, preferably less than about 0.5%, more preferably less than about 0.1%, still preferably less than about 0.05%, and still preferably less than about 0.02% of contaminant.

In yet another aspect, the present invention is directed to a method for producing a (Z)—O-octadec-9-en-1-yl O,O-dihydrogen phosphorothioate free acid. The method comprises the steps of: (i) mixing a thiophosphoryl chloride ($PSCl_3$) with oleyl alcohol in a reaction that also include a base and a solvent to obtain an intermediate O—(Z)-oleyl dichloridothiophosphate; and (ii) allowing a hydrolysis reaction of the intermediate O—(Z)-oleyl dichloridothiophosphate to form (Z)—O-octadec-9-en-1-yl O,O-dihydrogen phosphorothioate free acid.

In some embodiments, the solvent used in making the intermediate is a tetrahydrofuran, hexane, toluene, n-heptane, or a combination thereof, preferably n-heptane alone. In some embodiments, the base used in making the intermediate is a lutidine, pyridine, or a combination thereof, preferably pyridine alone.

In some embodiments, the amount of the base may be 1.5, 2.0, 2.5 or 3 equivalents of oleyl alcohol in the reaction. Further, the amount of the $PSCl_3$ may be 1.5, 2.0, 2.5 or 3 equivalents of oleyl alcohol in the reaction. In some instance, 1.5 equivalents of $PSCl_3$ and 1.5 equivalents of pyridine are preferably used in the reaction.

The addition sequence of $PSCl_3$, base, and oleyl alcohol may vary. In some embodiments, the mixture is preferably carried out by first forming a $PSCl_3$ and pyridine complex in heptane to the extent that the solution becomes a clear and then adding oleyl alcohol into the $PSCl_3$ and pyridine solution in a slow fashion, for example, in a drop-wise fashion.

The step of forming a $PSCl_3$ and pyridine complex in heptane may be performed at a temperature between about −20° C. and about 0° C. The step of adding oleyl alcohol may be performed at a temperature between about 0° C. and about 25° C. In some preferable embodiments, the former step is performed at about 0° C. and the latter step is performed at about 25° C.

In some embodiments, the method further comprises the steps of filtering and washing with an acidic solution the resultant intermediate O—(Z)-oleyl dichloridothiophosphate. The acidic solution may be a hydrochloride acid solution, the concentration of which may be about 0.5-2N, preferably 1N.

In some embodiments, the hydrolysis reaction may be carried out in the presence of sodium hydroxide or sodium bicarbonate, preferably sodium hydroxide. In some embodiments, the hydrolysis reaction further includes triethylamine in the hydrolysis reaction.

In some embodiments, the amount of sodium hydroxide may be about 1-5 equivalents and the amount of triethylamine may be about 1-5 equivalents of the amount of the intermediate O—(Z)-oleyl dichloridothiophosphate. In other embodiments, the amount of sodium hydroxide is about 3 equivalents and the amount of triethylamine is about 2 equivalents of the amount of the intermediate O—(Z)-oleyl dichloridothiophosphate. The hydrolysis reaction may be carried out under various conditions. Preferably, the hydrolysis reaction is carried out at 0-5° C.

In some embodiments, the methods further comprise the steps of acidifying the resultant hydrolysis reaction to pH 10-12 and washing the resultant (Z)—O-octadec-9-en-1-yl O,O-dihydrogen phosphorothioate free acid with IPAc. In some embodiments, the yield of the intermediate O—(Z)-oleyl dichloridothiophosphate is greater than 80%, preferably greater than 85%, more preferably greater than 90%, and still more preferably greater than 95%. Meanwhile, the yield of the (Z)—O-octadec-9-en-1-yl O,O-dihydrogen phosphorothioate free acid is similarly greater than 80%, preferably greater than 85%, more preferably greater than 90%, and still more preferably greater than 95%.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It should be understood that this invention is not limited to the particular methodologies, protocols and reagents, described herein, which may vary. The terminology used herein is for the purpose of describing particular embodiments only, and is not intended to limit the scope of the present invention.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

EXAMPLE 1

Improved Medicinal Chemistry Route of Synthesis for Rx100.FA

The prior procedure for making Rx100.FA involved phosphorylation of oleyl alcohol with bis(cyanoethyl)-N,N-diisopropylphosphoramidite in the presence of tetrazole followed by sulfurization with elemental sulfur. Protecting groups were then removed by β-elimination upon treatment with methanolic potassium hydroxide. After acidic work-up, Rx100.FA was isolated as a pale yellow oil. See the scheme I in FIG. 36.

1.1 Synthetic Approaches with Protective Groups and Activators

The prior medicinal chemistry approach (Scheme I—in FIG. 36) for the synthesis of Rx100.FA utilized $^1$H-tetrazole which is explosive and is not easily amenable to scale-up. We evaluated other activators to replace problematic $^1$H-tetrazole. We considered four alternatives for this purpose. They were 4,5-Dicyanoimidazole (DCI) with N-methyl imidazole (NMI); 5-Benzylthio-$^1$H-tetrazole; Pyridinium trifluoroacetate with NMI and 5-Ethyl thio-$^1$H-tetrazole.

As noted in Table 1, all four activators produced the bis-cyano intermediate (IM) in good yield. These new activators could replace tetrazole in Scheme I FIG. 36. The structure of the resultant intermediate was characterized by $^1$H NMR (nuclear magnetic resonance), $^{31}$P NMR (nuclear magnetic resonance) and Mass Spectrometry (MS) analysis. The highest yield was achieved using 3 equivalents (eq) of 4, 5-DCI with NMI. In contrast, reducing the excess reagents to 1.5 eq of 4, 5-DCI/NMI at 1 g scale batches resulted in no impurities detected by TLC or $^1$H-NMR in the intermediate (IM), Rx100 or Rx100.ammonia salt. Similarly, no impurities were observed with 1.5 eq of 5-ETT, 5-BTT or Pyr.TFA.

TABLE 1

Summary of activator screening.

| | Activator | Structure | Equivalents | Isolated Yield of Intermediate (IM) 2 |
|---|---|---|---|---|
| 1 | 4,5-Dicyanoimidazole | 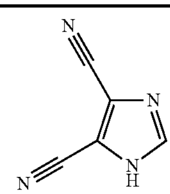 | 1.25 | 76% |
| | | | 1.5 | 80% |
| | | | 3 | 86% |
| 2 | 5-Ethylthio-1H-tetrazole | 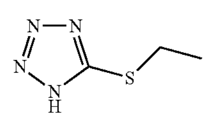 | 1.5 | 78% |
| 3 | Pyridinium trifluoroacetate | 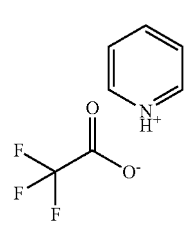 [SMILES: O=C([O-])C(F)(F)F ; c1cc[nH+]cc1] | 1.25 | 80% |
| 4 | 5-Benzylthio-1H-tetrazole | 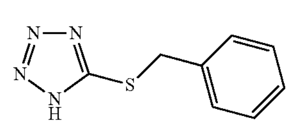 [SMILES: c1ccc(CSc2nnn[nH]2)cc1] | 1.25 | 74% |

In addition, the medicinal chemistry in Scheme I FIG. 36 utilized a P-linker (bis(cyanoethyl)-N,N-diisopropylphosphoramidite) that was considered impractical for scale-up. Deprotection of this P-linker has been associated with potential by-products that have suspected toxicity (acrylonitriles). Therefore, a safer and more practical scale-up option was sought. We considered five P-linkers. These were evaluated for conversion of oleyl alcohol to the intermediate (IM).

As shown in Table 2, the combination of either 5-BTT/NMI or di-tert-butyl N, N-diisopropylphosphoramidite provided the desired IM in 63% yield. However, the t-butyl groups under aqueous 1N and 4N HCl conditions could not be removed. In addition, phosphorylation of oleyl alcohol with O,O-Dimethyl phosphorochloridothioate was successful in 70% yield. However, the deprotection of the methoxy groups from the IM using TMSBr was unsuccessful. Further, phosphorylation of oleyl alcohol with O,O-Diethyl phosphorochloridothioate was successful in 60% yield. Phosphorylation with 1,8-Diazabicyclo [5.4.0]undec-7-ene (DBU), while successful, occurred more slowly than with sodium hydride. Still further, the P-linker O,O,O-tris(4-nitrophenyl) phosphorothioate was prepared from p-nitrophenol and thiophosphoryl chloride in 70% yield.

The use of protected P-linkers as a scale-up approach, although theoretically feasible, did have a less favorable features. For example, the nitro compounds were considered to have toxicity potential and it was difficult to hydrolyze the alkyl protected groups.

TABLE 2

Summary of protected P-linker screening

| | P-linker | Structure | Equivalents | Isolated Yield of IM |
|---|---|---|---|---|
| 1 | Di-tert-butyl N,N-diisopropylphosphoramidite | 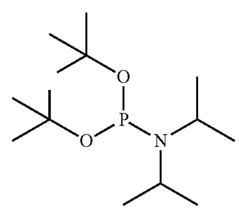 [SMILES: CC(C)N(C(C)C)P(OC(C)(C)C)OC(C)(C)C] | 1.5 | 63% |
| 2 | O,O-Diethyl phosphorochloridothioate | 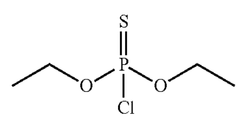 | 1.5 | 60% |
| 3 | O,O-Dimethyl phosphorochloridothioate | 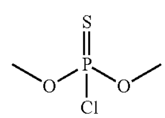 | 1.5 | 70% |
| 4 | O,O,O-tris(4-nitrophenyl) phosphorothioate | 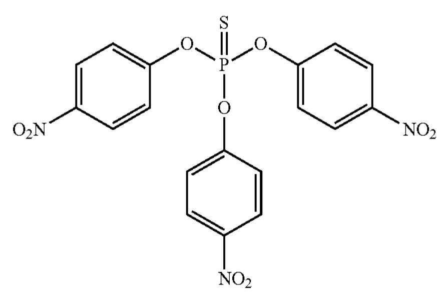 [SMILES: O=[N+]([O-])c1ccc(OP(=S)(Oc2ccc([N+](=O)[O-])cc2)Oc2ccc([N+](=O)[O-])cc2)cc1] | N/A | Use of this P-linker to form the IM was not performed. This compound may be toxic due to nitro groups. |
| 5 | Bis (4-methoxybenzyl) chlorothiophosphate | 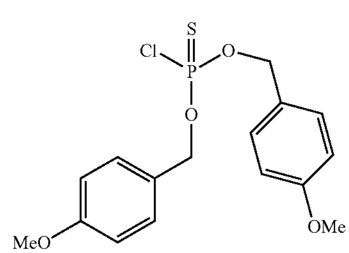 [SMILES: COc1ccc(COP(=S)(Cl)OCc2ccc(OC)cc2)cc1] | N/A | P-linker synthesis was not successful. This compound may be toxic. |

1.2 Synthetic Approaches without Use of Protective Groups and Activators

Synthesis of O—(Z)-oleyl dichloridothiophosphate (IM) 2 from (Z)-oleyl alcohol 1 (see Scheme II in FIG. 37) was performed by utilizing a published procedure for other alkyl alcohols; described in Angewandte Chemie International Edition, 2008, 47 (7), pp 1323-1325, 2008; and Langmuir., 1989, 5(5), pp 1200-5. In preliminary experiments, we found that O—(Z)-oleyl dichloridothiophosphate (IM) 2 can be prepared from oleyl alcohol and thiophosphoryl chloride using Et3N as base in 60% yield.

Synthesis of IM 2 and hydrolysis to Rx100 3 in Scheme II FIG. 37 utilized a simple and direct approach and was thought to be more economical than utilizing protected phosphate compounds at production scale.

We evaluated numerous synthesis variables at gram scale in the synthesis of O—(Z)-oleyl dichloridothiophosphate (IM) 2 to better understand the reaction, product yield and quantity of by-products. The variables studied were stoichiometry, Lewis base strength, absence of organic base, reaction solvent (varied by dielectric constant), temperature, duration of reaction and order of addition. Table 3 summarizes results of the process chemistry variables evaluated in the first synthetic step.

Further, we found that synthesis of O—(Z)-oleyl dichloridothiophosphate in the presence of activators (DMAP and imidazole), and mixed solvent systems were evaluated and no benefit of their presence was noted.

1.3 Hydrolysis of IM to Obtain Rx100.FA

There are a few reactions published on the hydrolysis of dichlorothiophosphates. In the Journal of the American Chemical Society, 110(23), 7900-1; 1988, sodium hydroxide was used in the hydrolysis of O-aryl dichlorothiophosphate to obtain O-aryl thiophosphate. In Angewandte Chemie, International Edition, 47(7), 1323-1325, 2008, the two chloride groups in 2,4-nitrophenyl dichlorothiophosphate were replaced with acetate groups using sodium acetate and triethylamine followed by in situ hydrolysis under basic conditions to produce the thiophosphate.

We investigated hydrolysis of O—(Z)-oleyl dichloridothiophosphate (IM) 2 to form Rx100 (free acid) 3 (Scheme III, FIG. 38) in sodium hydroxide or sodium bicarbonate in the presence or absence of triethylamine in a water and organic solvent mixtures. Using milder reaction conditions namely, 0.5 N sodium bicarbonate in the presence of triethylamine, provided a slower reaction rate (complete in 3 h) than with sodium hydroxide/triethylamine, while the impurity level

TABLE 3

Summary of Variables Evaluated in the Formation of O-(Z)-oleyl dichloridothiophosphate.

| Variable | Process chemistry | Result |
|---|---|---|
| Absence of base | Reaction was performed using 1.5-3 eq of PSCl$_3$ at room temperature and at 70° C. for 16 h to 48 h. Product was isolated after silica gel purification. | Low yields (30-50%) even after prolonged reaction time and elevated reaction temperature. |
| Base screening | Several bases (triethylamine, lutidine, DBU, pyridine, N-methyl morpholine, imidazole, N-methyl imidazole, N,N-diisopropylamine) were investigated at 2.5 eq. Except lutidine and pyridine, all other bases gave poor yields and unknown impurities as indicated by $^1$HNMR. | Pyridine emerged as a good choice with better yield and product purity. |
| Solvent | Reaction was performed using 1.5 eq of PSCl$_3$ and 1.5 eq of triethylamine or pyridine as base in many solvents with varying dielectric constant (1.9-21). Mixture of solvents was also evaluated. Reaction rate was slow in THF, hexanes and toluene (~18 h). Methyl tert-butyl ether gave poor yields. | n-Heptane was a good solvent. |
| Influence of activator | Dimethylamino pyridine and imidazole were added to the reaction mixture. Reaction was completed in 5 h. Product was isolated after silica gel column. $^1$H and $^{31}$P NMR analysis showed unknown impurities and no advantage with activators was observed. | Addition of catalytic amounts of activator did not improve the yields or purity profile of the product. |
| Reactant stoichiometry | Base and PSCl$_3$ stoichiometry was varied (1.5, 2, 2.5 and 3 eq) and reaction performed in heptane. Product yield decreased with an increase in stoichiometry. Base to PSCl3 in a ratio of 1:1 (at 1.5 eq) is optimum for step-1. | 1.5 eq of PSCl$_3$ and 1.5 eq of Pyridine worked good. |
| Reaction temperature | Reaction was studied at various temperatures (−40° C. to 0° C.; −10° C. to 0° C.; 0° C. to 20° C. and 20° C.) using 1.5 eq of pyridine and 1.5 eq of PSCl$_3$ in heptane. | 0° C. to 20° C. was sufficient for reaction completion with good yields and purity. |
| Reaction duration | Reaction progress was monitored by thin layer chromatography (TLC) for disappearance of oleyl alcohol. Reaction rate depends on solvent, base and temperature. | Reaction in heptanes goes to completion when stirred for 4-5 hours using pyridine as base. |
| Addition sequence | Three addition sequences were investigated. TLC analysis was used for reaction progress and impurity formation. Poor yields observed when a pre-mixed solution of oleyl alcohol and pyridine were added to PSCl$_3$. | Formation of a PSCl$_3$ - pyridine complex in heptane at 0° C. (observed as becoming a clear solution with fine ppt.) followed by slow addition of oleyl alcohol worked good. | was greater, the desired yield remained the same. In the absence of triethylamine, the reaction took significantly longer time to complete; about 18 hours in the case of sodium hydroxide and 20 hours in the case of sodium bicarbonate reaction. Yields were around 95% regardless of reaction conditions, at gram scale.

EXAMPLE 2

Identification and Crystallization of the Rx100.L-Lysine Salt

We previously isolated an Rx100.Ammonia salt via freeze-drying of a suspension of Rx100-free acid in methanolic ammonia. See the Scheme III in FIG. 38. As explained in the Background section, the ammonia salt is less desirable and a new salt form is sought after as described in this Example 2.

2.1 Screening for Rx100 Crystalline Salts.

We designed a complex and unconventional screening regime to screen for Rx100 crystalline salts. The most viable Rx100 salts were chosen for further characterization based on crystallinity, filterability, stability at high humidity and polymorphic behavior. The screening regime is described as follows.

(THF), were used. Thus in this first round of screening, 44 individual base-acid reactions were conducted in 44 vials.

First, Rx100.FA and each of the bases were mixed in a vial. Briefly, 1.651 g Rx100.FA liquid was dissolved in 8.255 mL (×5 volumes) of ethanol (designated as 1980-1-1). In each of the 44 vials, 211.1 µL of the prepared liquid, which was equivalent to about 35 mg of Rx100.FA, was first dispensed. Then, one equivalent (molar) of each of the 11 bases was dispensed in its corresponding vial. For example, the base sodium hydroxide was added to vials 1, 12, 23 and 34. Similarly, L-histidine was added to vials 11, 22, 33 and 44. Observations were recorded upon addition of the bases in to Rx100.FA.

Second, the solvent in each mixture was depleted. All vials containing the mixtures of Rx100.FA and each of the bases were left under moderate vacuum and nitrogen bleed at room temperature overnight to evaporate the solvent. The vials were then kept under full vacuum for about an hour to make sure the solvents (ethanol and water) are evaporated. Observations on formation of solid upon evaporation were recorded.

Third, solvents were added in each vial to induce solid formation. In each vial, a stir bar and one of the four selected solvents (each 5 volumes with respect to the Rx100.FA)

TABLE 4

List of bases and their corresponding number.

| Base number | Experiment Stage | Base name | Base was prepared in | Solution concentration, wt % |
|---|---|---|---|---|
| 1 | Stage 1 | Sodium hydroxide | Water | 9.7 |
| 2 | | Ammonium hydroxide | Water | 10.2 |
| 3 | | Ethylenediamine | N/A | 99.0 |
| 4 | | Diethylamine | N/A | 99.0 |
| 5 | | Tromethamine (Tris) | Water | 10.0 |
| 6 | | Hydroxyethyl morpholine | N/A | 99.0 |
| 7 | | Benzathine | N/A | 97.0 |
| 8 | | Dimethylamino ethanol (DEE) | N/A | 99.0 |
| 9 | | L-Arginine | Water | 5.0 |
| 10 | | L-Lysine | Water | 10.0 |
| 11 | | L-Histidine | Water | 4.0 |
| 12 | Stage 2 | KOH | Water | 8.2 |
| 13 | | Ca(OH)$_2$ | Solid was used | 95 (solid) |
| 14 | | Diethanolamine | N/A | 99.0 |
| 15 | | Meglumine | Water | 21.4 |
| 16 | Stage 3 | D-Lysine | Water | 43.9 |
| 17 | | Glycine | Water | 34.7 |
| 18 | | Piperazine | Water | 43.1 |

Rx100.FA in the form of a viscous liquid and eighteen counter ions were used as starting materials. These counter ions are listed and numbered in Table 4. The numbers will be used for grouping the resulting solids. The screening was performed in three stages.

Stage one (1) included screening 11 counter ions: sodium hydroxide, ammonium hydroxide, ethylenediamine, diethylamine, tromethamine (Tris), hydroxyethyl morpholine, benzathine, dimethylamino ethanol, L-Arginine, L-Lysine, L-Histidine. A hundred and sixteen (116) different conditions were studied in eight (8) solvents and two (2) quantities of 1.1 and 2.1 equivalences of bases. In stage 1, we performed three rounds of experiment.

In the first round of experiment, four (4) solvent systems, i.e., isopropyl alcohol (IPA), diethyl ether (DEE), IPA:water (a mixture at a volume ratio of 95:5) and tetrahydrofuran were added. The vials were then capped. IPA was added to the first set of 11 vials (1-11), DEE added to the second set of 11 vials (12-22), IPA:water added to the third set of 11 vials (23-33), and THF added to the fourth set of 11 vials (34-44). The vials were left at room temperature while stirring for at least 5 hours. Observations were recorded.

Fourth, samples were taken from the vials that showed precipitation for XRPD analysis. See Table 5. The first set of XRPD analyses were recorded as "wet" samples. The solids were dried under vacuum for 1 hour and at room temperature followed by XRPD as "dry" sample. The dry solid was then exposed to relative humidity of more than 90% overnight followed by XRPD analysis. For XRPD naming, a number and a letter were used. The number refers to the counter ion and the letter refers to the chronological discovered XRPD pattern of that particular salt. For example, 1-A is pattern A of sodium salt and 2-A is the pattern A of ammonium salt.

TABLE 5

Rx100 salt screening results in the first round of experiment in stage 1. "NE" refers to "not enough".

| 1980- | FA, mg | Base | Base, uL | Solid upon reaction | Solid upon evaporation | Solvent | Slurry (crystal/oil) | XRPD, Wet | XRPD, Dry | RH > 90% overnight | On XRPD plate |
|---|---|---|---|---|---|---|---|---|---|---|---|
| 2-1 | 35 | sodium hydroxide | 39.53 | Y | Y | IPA | Y | 1-A | 1-A | 1-A | oily |
| 2-2 | 35 | Ammonium hydroxide | 17.63 | Y | Y | IPA | Y | 2-A | 2-B | 2-B | oily |
| 2-3 | 35 | Ethylenediamine | 7.00 | Y | Y | IPA | Y | 3-A | 3-A | — | Creamy/oily |
| 2-4 | 35 | Diethylamine | 10.78 | N | N | IPA | — | — | — | — | — |
| 2-5 | 35 | tromethamine (Tris) | 124.60 | N | N | IPA | — | — | — | — | — |
| 2-6 | 35 | hydroxyethyl morpholine | 12.71 | N | N | IPA | — | — | — | — | — |
| 2-7 | 35 | benzathine | 24.08 | N | N | IPA | — | — | — | — | — |
| 2-8 | 35 | dimethylamino ethanol | 10.48 | N | N | IPA | — | — | — | — | — |
| 2-9 | 35 | L-Arginine | 358.62 | N | N | IPA | Y | Gel | — | — | — |
| 2-10 | 35 | L-Lysine | 148.56 | Y | Y | IPA | Y | NE* | — | — | — |
| 2-11 | 35 | L-Histidine | 399.12 | N | N | IPA | Y | Gel | — | — | — |
| 2-12 | 35 | sodium hydroxide | 39.53 | Y | Y | DEE | Y | 1-B | 1-C | 1-C | oily |
| 2-13 | 35 | Ammonium hydroxide | 17.63 | Y | Y | DEE | — | — | — | — | — |
| 2-14 | 35 | ethylenediamine | 7.00 | Y | Y | DEE | Y | 3-A | 3-A | 3-A | Creamy/oily |
| 2-15 | 35 | diethylamine | 10.78 | N | N | DEE | — | — | — | — | — |
| 2-16 | 35 | tromethamine (Tris) | 124.60 | N | N | DEE | Y | 5-A | 5-A | 5-A | oily |
| 2-17 | 35 | hydroxyethyl morpholine | 12.71 | N | N | DEE | — | — | — | — | — |
| 2-18 | 35 | benzathine | 24.08 | N | N | DEE | — | — | — | — | — |
| 2-19 | 35 | dimethylamino ethanol | 10.48 | N | N | DEE | — | — | — | — | — |
| 2-20 | 35 | L-Arginine | 358.62 | N | N | DEE | Y | Gel | — | — | — |
| 2-21 | 35 | L-Lysine | 148.56 | Y | Y | DEE | Y | 10-A | 10-A | 10-A | Solid |
| 2-22 | 35 | L-Histidine | 399.12 | N | N | DEE | Y | Gel | — | — | — |
| 2-23 | 35 | sodium hydroxide | 39.53 | Y | Y | IPA:water (95:5) | Y | 1-D | 1-E | — | oily |
| 2-24 | 35 | Ammonium hydroxide | 17.63 | Y | Y | IPA:water (95:5) | — | — | — | — | — |
| 2-25 | 35 | ethylenediamine | 7.00 | Y | Y | IPA:water (95:5) | Y | 3-A | 3-A | — | Greasy |
| 2-26 | 35 | diethylamine | 10.78 | N | N | IPA:water (95:5) | — | — | — | — | — |
| 2-27 | 35 | tromethamine (Tris) | 124.60 | N | N | IPA:water (95:5) | — | — | — | — | — |
| 2-28 | 35 | hydroxyethyl morpholine | 12.71 | N | N | IPA:water (95:5) | — | — | — | — | — |
| 2-29 | 35 | benzathine | 24.08 | N | N | IPA:water (95:5) | — | — | — | — | — |
| 2-30 | 35 | dimethylamino ethanol | 10.48 | N | N | IPA:water (95:5) | — | — | — | — | — |
| 2-31 | 35 | L-Arginine | 358.62 | N | N | IPA:water (95:5) | Y | Gel | — | — | — |
| 2-32 | 35 | L-Lysine | 148.56 | Y | Y | IPA:water (95:5) | Y | NE | — | — | — |
| 2-33 | 35 | L-Histidine | 399.12 | N | N | IPA:water (95:5) | Y | Gel | — | — | — |
| 2-34 | 35 | sodium hydroxide | 39.53 | Y | Y | THF | Y | 1-C | — | — | oily |
| 2-35 | 35 | Ammonium hydroxide | 17.63 | Y | Y | THF | — | — | — | — | — |
| 2-36 | 35 | ethylenediamine | 7.00 | Y | Y | THF | Y | 3-A | — | — | Creamy/oily |
| 2-37 | 35 | diethylamine | 10.78 | N | N | THF | — | — | — | — | — |
| 2-38 | 35 | tromethamine (Tris) | 124.60 | N | N | THF | — | — | — | — | — |
| 2-39 | 35 | hydroxyethyl morpholine | 12.71 | N | N | THF | — | — | — | — | — |
| 2-40 | 35 | benzathine | 24.08 | N | N | THF | — | — | — | — | — |
| 2-41 | 35 | dimethylamino ethanol | 10.48 | N | N | THF | — | — | — | — | — |

TABLE 5-continued

Rx100 salt screening results in the first round of experiment in stage 1. "NE" refers to "not enough".

| 1980- | FA, mg | Base | Base, uL | Solid upon reaction | Solid upon evaporation | Solvent | Slurry (crystal/oil) | XRPD, Wet | XRPD, Dry | RH > 90% overnight | On XRPD plate |
|---|---|---|---|---|---|---|---|---|---|---|---|
| 2-42 | 35 | L-Arginine | 358.62 | N | N | THF | Y | Gel | — | — | — |
| 2-43 | 35 | L-Lysine | 148.56 | Y | Y | THF | Y | NE | — | — | — |
| 2-44 | 35 | L-Histidine | 399.12 | N | N | THF | Y | Gel | — | — | — |

In the second round of experiment of stage one, another four (4) solvent systems, i.e., methanol (MeOH), tert-Butyl methyl ether (tBME), ethyl acetate and toluene, were used in the same 44 vials as used in the first round experiment. The solvents in all 44 vials from the first round were evaporated to dryness under vacuum and nitrogen bleed. The 4 new solvents were then added into the vials. Methanol was added to the first set of 11 vials (1-11), tBME added to the second set of 11 vials (12-22), Ethyl acetate added to the third set of 11 vials (23-33), and Toluene added to the fourth set of 11 vials (34-44). The same procedure as in the first round of experiment was followed for these new solvents and samples were taken for XRPD analysis. See Table 6 for the results.

TABLE 6

Rx100 salt screening results in the second round of experiment in stage 1.

| 1980- | Base | New solvents added | Slurry (crystal/oil)? | XRPD, wet | On Plate |
|---|---|---|---|---|---|
| 3-1 | sodium hydroxide | MeOH | Y | 1-B | Oily |
| 3-2 | Ammonium hydroxide | MeOH | Y | 2-A | Oily |
| 3-3 | ethylenediamine | MeOH | Y | 3-A | Creamy/oily |
| 3-4 | diethylamine | MeOH | — | — | — |
| 3-5 | tromethamine (Tris) | MeOH | — | — | — |
| 3-6 | hydroxyethyl morpholine | MeOH | — | — | — |
| 3-7 | benzathine | MeOH | — | — | — |
| 3-8 | dimethylamino ethanol | MeOH | — | — | — |
| 3-9 | L-Arginine | MeOH | Y | — | Gel |
| 3-10 | L-Lysine | MeOH | Y | 10-A | Pasty |
| 3-11 | L-Histidine | tBME | Y | 11-A | Greasy |
| 3-12 | sodium hydroxide | tBME | Y | 1-B | Oily |
| 3-13 | Ammonium hydroxide | tBME | Y | 2-C | Oily |
| 3-14 | ethylenediamine | tBME | Y | 3-A | Creamy/oily |
| 3-15 | diethylamine | tBME | — | — | — |
| 3-16 | tromethamine (Tris) | tBME | — | — | — |
| 3-17 | hydroxyethyl morpholine | tBME | — | — | — |
| 3-18 | benzathine | tBME | — | — | — |
| 3-19 | dimethylamino ethanol | tBME | — | — | — |
| 3-20 | L-Arginine | tBME | — | — | — |
| 3-21 | L-Lysine | tBME | Y | 10-A | Pasty |
| 3-22 | L-Histidine | tBME | Y | 11-B | Greasy |
| 3-23 | sodium hydroxide | Ethyl acetate | Y | 1-A | Greasy |
| 3-24 | Ammonium hydroxide | Ethyl acetate | Y | — | — |
| 3-25 | ethylenediamine | Ethyl acetate | Y | 3-A | Creamy/oily |
| 3-26 | diethylamine | Ethyl acetate | — | — | — |
| 3-27 | tromethamine (Tris) | Ethyl acetate | — | — | — |
| 3-28 | hydroxyethyl morpholine | Ethyl acetate | — | — | — |
| 3-29 | benzathine | Ethyl acetate | — | — | — |
| 3-30 | dimethylamino ethanol | Ethyl acetate | — | — | — |
| 3-31 | L-Arginine | Ethyl acetate | Y | — | Gel |
| 3-32 | L-Lysine | Ethyl acetate | Y | 10-A | Pasty |
| 3-33 | L-Histidine | Ethyl acetate | — | — | — |
| 3-34 | sodium hydroxide | Toluene | — | — | — |
| 3-35 | Ammonium hydroxide | Toluene | — | — | — |
| 3-36 | ethylenediamine | Toluene | Y | 3-A | — |
| 3-37 | diethylamine | Toluene | — | — | — |
| 3-38 | tromethamine (Tris) | Toluene | — | — | — |
| 3-39 | hydroxyethyl morpholine | Toluene | — | — | — |
| 3-40 | benzathine | Toluene | — | — | — |
| 3-41 | dimethylamino ethanol | Toluene | — | — | — |
| 3-42 | L-Arginine | Toluene | Y | — | Gel |
| 3-43 | L-Lysine | Toluene | Y | — | Gel |
| 3-44 | L-Histidine | Toluene | Y | — | Gel |

In the third round of experiment, effect of base equivalence was assessed. Here, an extra one equivalent (one molar basis) of base was added to the vials that did not form a solid in the first and second rounds of experiment. After addition of the extra base, the previous solvent was evaporated and new solvents added. Table 7 shows the results after adding one extra equivalent of base in the indicated reactions.

gen bleed at room temperature overnight to evaporate the solvent. The vials were then kept under full vacuum for about an hour to make sure the solvents (ethanol and water) are evaporated. Observations on formation of solid upon evaporation were recorded. Then, stir bars were added to each vial and four selected solvents (each 5 volumes with respect to free acid) were added. The vials were capped. IPA

TABLE 7

Rx100 salt screening results in the third round of experiment using 2 equivalent of base in stage 1.

| 1980- | Base | Solvent | Additional base to 2.1 eq, uL | Precipitation? | on Plate | XRPD, wet | RH > 900% overnight |
|---|---|---|---|---|---|---|---|
| 4-2 | Ammonium hydroxide | MeOH | 14.4 | Y | Oily | 2-C | 2-D |
| 4-4 | diethylamine | MeOH | 9.8 | — | — | — | — |
| 4-5 | tromethamine (Tris) | MeOH | 113 | — | — | — | — |
| 4-6 | hydroxyethyl morpholine | MeOH | 11.6 | — | — | — | — |
| 4-7 | benzathine | MeOH | 21.9 | — | — | — | — |
| 4-8 | dimethylamino ethanol | MeOH | 9.5 | — | — | — | — |
| 4-9 | L-Arginine | MeOH | 32.6 | Y | Gel | — | — |
| 4-13 | Ammonium hydroxide | tBME | 14.4 | — | — | — | — |
| 4-15 | diethylamine | tBME | 9.8 | — | — | — | — |
| 4-16 | tromethamine (Tris) | tBME | 113 | Y | Greasy | 5-A + Tris | 5-A + Tris |
| 4-17 | hydroxyethyl morpholine | tBME | 11.6 | — | — | — | — |
| 4-18 | benzathine | tBME | 21.9 | — | — | — | — |
| 4-19 | dimethylamino ethanol | tBME | 9.5 | — | — | — | — |
| 4-20 | L-Arginine | tBME | 326 | Y | Greasy | 9-A | Turned into an amorphous gel |
| 4-24 | Ammonium hydroxide | Ethyl acetate | 14.4 | Y, gel | — | — | — |
| 4-26 | diethylamine | Ethyl acetate | 9.8 | — | — | — | — |
| 4-27 | tromethamine (Tris) | Ethyl acetate | 113 | Y, gel | — | — | — |
| 4-28 | hydroxyethyl morpholine | Ethyl acetate | 11.6 | — | — | — | — |
| 4-29 | benzathine | Ethyl acetate | 21.9 | — | — | — | — |
| 4-30 | dimethylamino ethanol | Ethyl acetate | 9.5 | — | — | — | — |
| 4-31 | L-Arginine | Ethyl acetate | 326 | Y | Solid | 9-A | Turned into an amorphous gel |
| 4-35 | Ammonium hydroxide | DEE | 14.4 | — | — | — | — |
| 4-37 | diethylamine | DEE | 9.8 | — | — | — | — |
| 4-38 | tromethamine (Tris) | DEE | 113 | Y | Greasy | 5-A | 5-B |
| 4-39 | hydroxyethyl morpholine | DEE | 11.6 | — | — | — | — |
| 4-40 | benzathine | DEE | 21.9 | — | — | — | — |
| 4-41 | dimethylamino ethanol | DEE | 9.5 | — | — | — | — |
| 4-42 | L-Arginine | DEE | 326 | Y | Solid | 9-A | Turned into an amorphous gel |

In stage 2 of the screening, four additional bases were tested according to the same procedure in stage 1. The four bases were KOH, Ca(OH)$_2$, Diethanolamine, and Meglumine.

In the first round of experiment in stage 2, four solvents, i.e., IPA, MeOH, IPA:water (95:5 vol), and tBME, were used. Briefly, 0.7821 g free acid liquid was dissolved in 3.91 mL (5 vol.) ethanol (1980-1-3). In each of the 20 vials, 211.1 µL of the prepared liquid, which was equivalent to about 35 mg of the Rx100.FA, was dispensed. Among the 20 vials, 16 were used for salt formation and 4 for evaluating the free acid precipitation as negative controls. One molar equivalent of each of the bases was dispensed in their corresponding vials. All vials were left under moderate vacuum and nitrowas added to the first set of 4 vials (1-4), methanol added to second set of 4 vials (5-8), IPA:water (95:5) added to the third set of 4 vials (9-12), and tBME added the third set of vials (13-16). In the fifth set of four vials which do not contain base, IPA, Methanol, IPA:water (95:5), and tBME were added, respectively. The capped vials were left at room temperature while stirring for at least 5 hours. Observations were recorded during the process. Samples were taken from the vials that showed precipitation for XRPD analysis. Data are reported in Table 8. The first set of XRPD analyses were recorded as "wet" samples. The solids were dried under vacuum and room temperature for one hour followed by XRPD as "dry" sample.

TABLE 8

Rx100 salt screening results in the first round of experiment in stage 2.

| 1980- | FA, mg | FA, uL | Base | Base, uL | Solid formation upon reaction | Solid upon evaporation | Solvent | Wet | Dry | Slurry (crystal/oil) upon solvent condition |
|---|---|---|---|---|---|---|---|---|---|---|
| 8-1 | 35 | 211.1 | KOH | 131.01 | — | — | IPA | — | — | gel |
| 8-2 | 35 | 211.1 | Ca(OH)$_2$ | 8.07 mg | Y | Y | IPA | Calcium hydroxide | — | Greasy |
| 8-3 | 35 | 211.1 | Diethanolamine | 10.99 | — | — | IPA | — | — | — |
| 8-4 | 35 | 211.1 | Meglumine | 93.06 | — | — | IPA | — | — | — |
| 8-5 | 35 | 211.1 | KOH | 131.01 | — | — | MeOH | 12-A | 12-A | Oily |
| 8-6 | 35 | 211.1 | Ca(OH)$_2$ | 8.07 mg | Y | Y | MeOH | — | — | Gel |
| 8-7 | 35 | 211.1 | Diethanolamine | 10.99 | — | — | MeOH | — | — | — |
| 8-8 | 35 | 211.1 | Meglumine | 93.06 | — | — | MeOH | — | — | — |
| 8-9 | 35 | 211.1 | KOH | 131.01 | — | — | IPA:water (95:5) | — | — | Gel |
| 8-10 | 35 | 211.1 | Ca(OH)$_2$ | 8.07 mg | Y | Y | IPA:water (95:5) | Calcium hydroxide | — | Greasy |
| 8-11 | 35 | 211.1 | Diethanolamine | 10.99 | — | — | IPA:water (95:5) | — | — | — |
| 8-12 | 35 | 211.1 | Meglumine | 93.06 | — | — | IPA:water (95:5) | — | — | — |
| 8-13 | 35 | 211.1 | KOH | 131.01 | — | — | tBME | 12-B | 12-B | Oily |
| 8-14 | 35 | 211.1 | Ca(OH)$_2$ | 8.07 mg | Y | Y | tBME | Calcium hydroxide | — | Greasy |
| 8-15 | 35 | 211.1 | Diethanolamine | 10.99 | — | — | tBME | — | — | — |
| 8-16 | 35 | 211.1 | Meglumine | 93.06 | — | — | tBME | — | — | — |
| 8-17 | 35 | 211.1 | None | — | — | — | IPA | — | — | — |
| 8-18 | 35 | 211.1 | None | — | — | — | MeOH | — | — | — |
| 8-19 | 35 | 211.1 | None | — | — | — | IPA:water (95:5) | — | — | — |
| 8-20 | 35 | 211.1 | None | — | — | — | tBME | — | — | — |

In the second round of experiment in stage 2, four additional solvents were tested. The solvents in all 20 vials of the first round in stage 1 were evaporated to dryness under vacuum and nitrogen bleed. Then 4 new solvents were added; Ethyl acetate, IPA:water (1:1 vol), diethyl ether and THF. The same procedure as that in the first round in stage 1 was followed with these new solvents and samples were taken for XRPD analysis as shown in Table 9.

TABLE 9

Rx100 salt screening results in the second round of experiment in stage 2.

| 1980- | Base | New solvents added | Slurry (crystal/oil)? | XRPD, wet | ON PLATE |
|---|---|---|---|---|---|
| 10-1 | KOH | Ethyl acetate | Y | 12-C | Greasy |
| 10-2 | Ca(OH)$_2$ | Ethyl acetate | Y | Calcium hydroxide | — |
| 10-3 | Diethanolamine | Ethyl acetate | — | — | — |
| 10-4 | Meglumine | Ethyl acetate | — | — | — |
| 10-5 | KOH | IPA:water (1:1) | Y | 12-D | Pasty |
| 10-6 | Ca(OH)$_2$ | IPA:water (1:1) | Y | Calcium hydroxide | — |
| 10-7 | Diethanolamine | IPA:water (1:1) | — | — | — |
| 10-8 | Meglumine | IPA:water (1:1) | — | — | — |
| 10-9 | KOH | DEE | — | — | — |
| 10-10 | Ca(OH)$_2$ | DEE | Y | — | — |
| 10-11 | Diethanolamine | DEE | — | — | — |
| 10-12 | Meglumine | DEE | — | — | — |
| 10-13 | KOH | THF | — | — | — |
| 10-14 | Ca(OH)$_2$ | THF | — | — | — |
| 10-15 | Diethanolamine | THF | Y | — | — |
| 10-16 | Meglumine | THF | — | — | — |
| 10-17 | — | Ethyl acetate | — | — | — |
| 10-18 | — | IPA:water (1:1) | — | — | — |
| 10-19 | — | DEE | — | — | — |
| 10-20 | — | THF | — | — | — |

In stage 3 of the screening, three additional bases together with L-lysine were tested according to the same procedure in stage 1. The three additional bases were D-lysine, Glycine, and Piperazine. In addition to the three new counter ions, L-Lysine was also used at 2 molar equivalents. Two solvents were selected for screening. These solvents were methanol and methanol:water (9:1). Briefly, 0.3 g free acid liquid was dissolved in 1.5 mL (5 vol.) ethanol (1980-12). In each of 8 vials, 211.1 µL of the prepared liquid, which was equivalent to about 35 mg of the free acid, was dispensed. Likewise, one molar equivalent of each of the bases was dispensed in the corresponding vials with the exception for L-Lysine where 2 equivalents were used. All vials were left under vacuum and nitrogen bleed at room temperature to evaporate the solvent. Observations on formation of solid upon evaporation were recorded. Then, stir bars were added to each vial and four selected solvents (each 5 volumes with respect to free acid) were added and capped the vials. The capped vials were left at room temperature while stirring for at least 5 hrs. Observations were recorded. Samples were taken from the vials that showed precipitation for XRPD analysis. Data are reported in Table 10. The first set of XRPD analyses were recorded as "wet" samples. The solids were dried under vacuum and room temperature for one hour followed by XRPD as "dry" sample. The dry sample was exposed to high humidity for two days followed by XRPD analysis.

TABLE 10

Rx100 salt screening results in the first round of experiment in stage 3.

| 1980- | Free Acid (mg) | Base | Base eq. | Base (uL) | Cloudy upon reaction (Y/N)? | Solid upon evaporation (Y/N) | Solvents | Slurry (crystal/oil) upon solvent addition | Wet | Dry | Exposed to high RH overnight | All solvents evaporated were to get a gel |
|---|---|---|---|---|---|---|---|---|---|---|---|---|
| 12-5 | 35 | L-lysine | 2.00 | 86.18 | Y | Gel | MeOH | Y | 10-B | 10-B | 10-B | Filterable solid |
| 12-6 | 35 | D-lysine | 1.05 | 30.23 | Y | Gel | MeOH | Y | 16-A | 16-B | 16-D | Greasy. Tiny amount recovered |
| 12-7 | 35 | Glycine | 1.05 | 18.88 | Y | Gel | MeOH | Y | 17-A | 17-B | 17-E | Greasy. Tiny amount recovered |
| 12-8 | 35 | Piperazine | 1.05 | 18.32 | Y | Gel | MeOH | Y | 18-A | 18-B | 18-C | Greasy. Tiny amount recovered |
| 12-9 | 35 | L-lysine | 2.00 | 86.18 | Y | Gel | MeOH:Water [9:1] | Y | 10-B | 10-B | 10-B | Solid |
| 12-10 | 35 | D-lysine | 1.05 | 30.23 | Y | Gel | MeOH:Water [9:1] | Y | 16-C | 16-C | 16-E | Greasy. Tiny amount recovered |
| 12-11 | 35 | Glycine | 1.05 | 18.88 | Y | Gel | MeOH:Water [9:1] | Y | 17-C | 17-D | 17-E | Greasy. Tiny amount recovered |
| 12-12 | 35 | Piperazine | 1.05 | 18.32 | Y | Gel | MeOH:Water [9:1] | Y | 18-A | 18-B | 18-C | Greasy. Tiny amount recovered |

From the results shown in Tables 5-10, Rx100 was either not forming a solid salt or in many cases, formed an oily solid salt which was not filterable. Among the bases studies, the following seven (7) bases did not result in any solid or salt in any of the studied solvents: diethylamine, hydroxyethyl morpholine, benzathine, dimethylamino ethanol, calcium hydroxide, diethanolamine and meglumine and therefore were not further characterized. Based on the criteria of crystallinity, filterability, solubility, stability at high humidity and polymorphic behavior, Rx100 salts formed with the remaining eleven bases are briefly characterized as shown in Table 11.

Among the eleven Rx100 salts, Rx100.L-Lysine salt and Rx100 Ethylenediamine salt showed desirable features. The Rx100.L-Lysine salt was in a pasty form, was filterable and stable at high humidity, and showed crystallinity in XRPD analysis. Similarly, the Rx100 Ethylenediamine salt was in a creamy and oily form, was filterable and stable at high humidity, and showed crystallinity in XRPD analysis.

TABLE 11

Characterization of eleven Rx100 salts.

| Base Name | Crystallinity | Filterability | Polymorphic behavior |
|---|---|---|---|
| Sodium | yes | no | Polymorphic on XRPD |
| Ammonium | yes | no | Oily on XRPD |
| Ethyldiamine | yes | yes | Creamy/oily on XRPD |
| Tromethamine | no | no | Oily on XRPD |
| L-Arginine | yes | yes* | Greasy on XRPD |
| L-Lysine | yes | yes | No change in form with one pattern on XRPD |
| Potassium | yes | no | Polymorphic on XRPD |
| D-Lysine | yes | no | Polymorphic on XRPD |
| Glycine | no | no | Multiple patterns on XRPD |
| Piperazine | yes | yes | Multiple patterns on XRPD |

*indicates that the salt is not filterable with one molar equivalent of base but is filterable with two molar equivalent.

Further characterization of the Rx100.L-Lysine and ethylenediamine salts were performed and it was determined that L-Lysine salt was soluble both in water and the simulated formulation solvent while ethylenediamine salt showed poor solubility. The simulated formulation solvent is composed of 3% polyethylene glycol 200, 1% ethanol, 10 mM monosodium phosphate and the balance water. Incremental addition method was used to determine the solubility: a known amount of the salt was used and water or formulation solution was added slowly until dissolution was observed at room temperature.

As a result, the Rx100.L-Lysine salt could be dissolved in water more than 48 mg/ml, and in the formulation solvent more than 43 mg/ml (much less foamy in the formulation solvent than in water). In contrast, Rx100 ethylenediamine salt could be dissolved in water no more than 0.4 mg/ml, and in the formulation solvent no more than 0.7 mg/ml.

The solubility of Rx100.L-Lysine salt was further tested in 13 additional solvents. As shown in Table 12, Rx100.L-Lysine salt was found to be soluble in the following five solvents: IPA-water (1:1), ethanol:water (1:1), methanol:water (1:1), methanol:water (8:2), and acetone:water (1:1).

TABLE 12

Qualitative solubility of Rx100.L-Lysine salt.

| 1980- | Solvent | Solid (mg) | Volume Added, mL | Observation |
|---|---|---|---|---|
| 14-1 | IPA | ~50 | 0.75 | slurry |
| 14-2 | EtOH | ~50 | 0.75 | slurry |
| 14-3 | MeOH | ~50 | 0.75 | slurry |
| 14-4 | Acetone | ~50 | 0.75 | slurry |
| 14-5 | THF | ~50 | 0.75 | slurry |
| 14-6 | IPA:water (1:1) | ~50 | 0.75 | dissolved |
| 14-7 | IPA:water (8:2) | ~50 | 0.75 | oil |
| 14-8 | EtOH:water (1:1) | ~50 | 0.75 | dissolved |
| 14-9 | EtOH:water (8:2) | ~50 | 0.75 | cloudy |
| 14-10 | MeOH:water (1:1) | ~50 | 0.5 | dissolved |
| 14-11 | MeOH:water (8:2) | ~50 | 0.75 | dissolved |
| 14-12 | Acetone:water (1:1) | ~50 | 0.5 | dissolved |
| 14-13 | THF:water(1:1) | ~50 | 0.5 | oil |

2.2. Stoichiometry Assessment of Rx100.L-Lysine Salt Form

Figure 1:
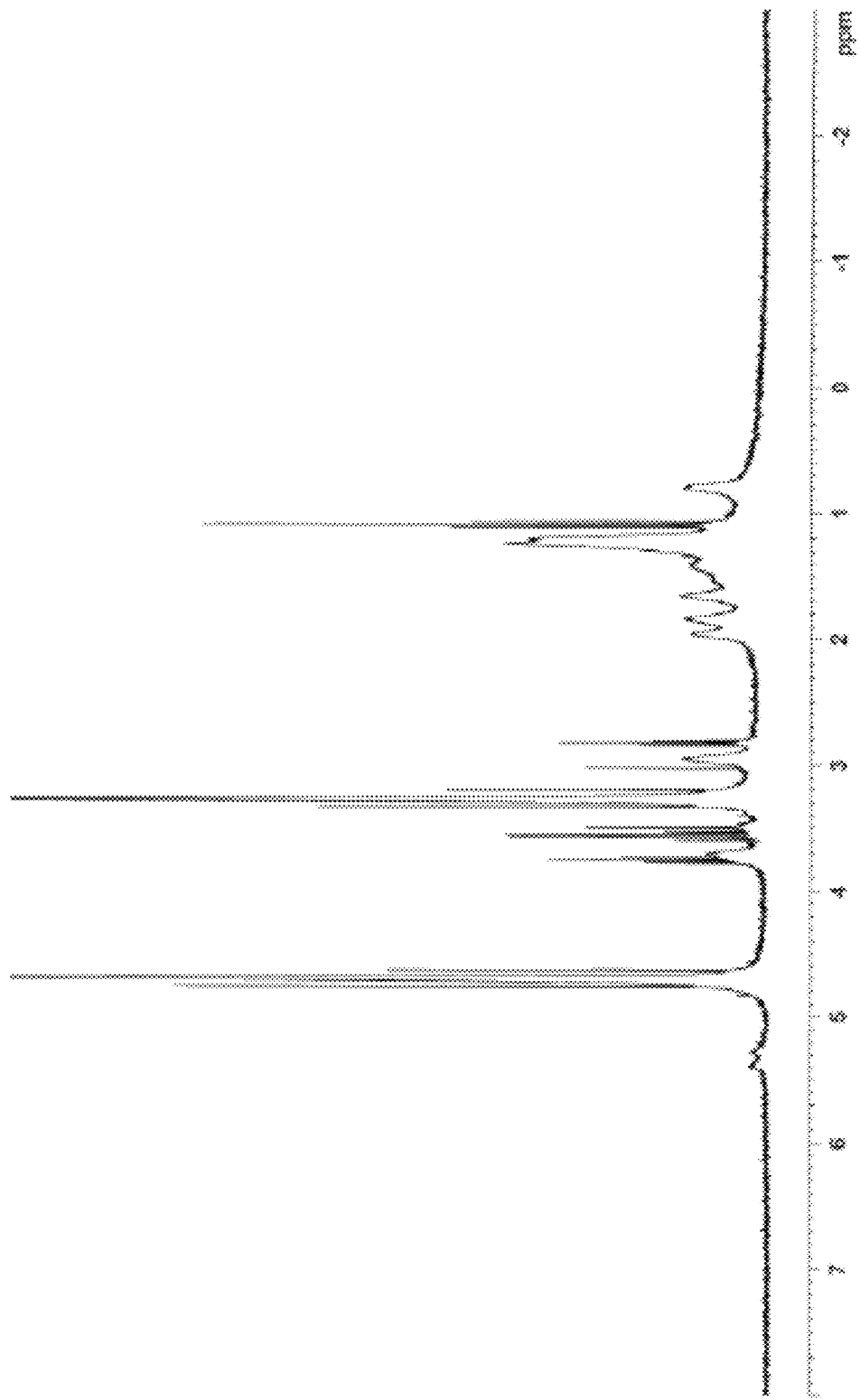
FIG. 1 shows a graph depicting a proton NMR analysis result of Rx100.L-Lysine salt prepared with 0.5 equivalent L-Lysine base.
Figure 2A:
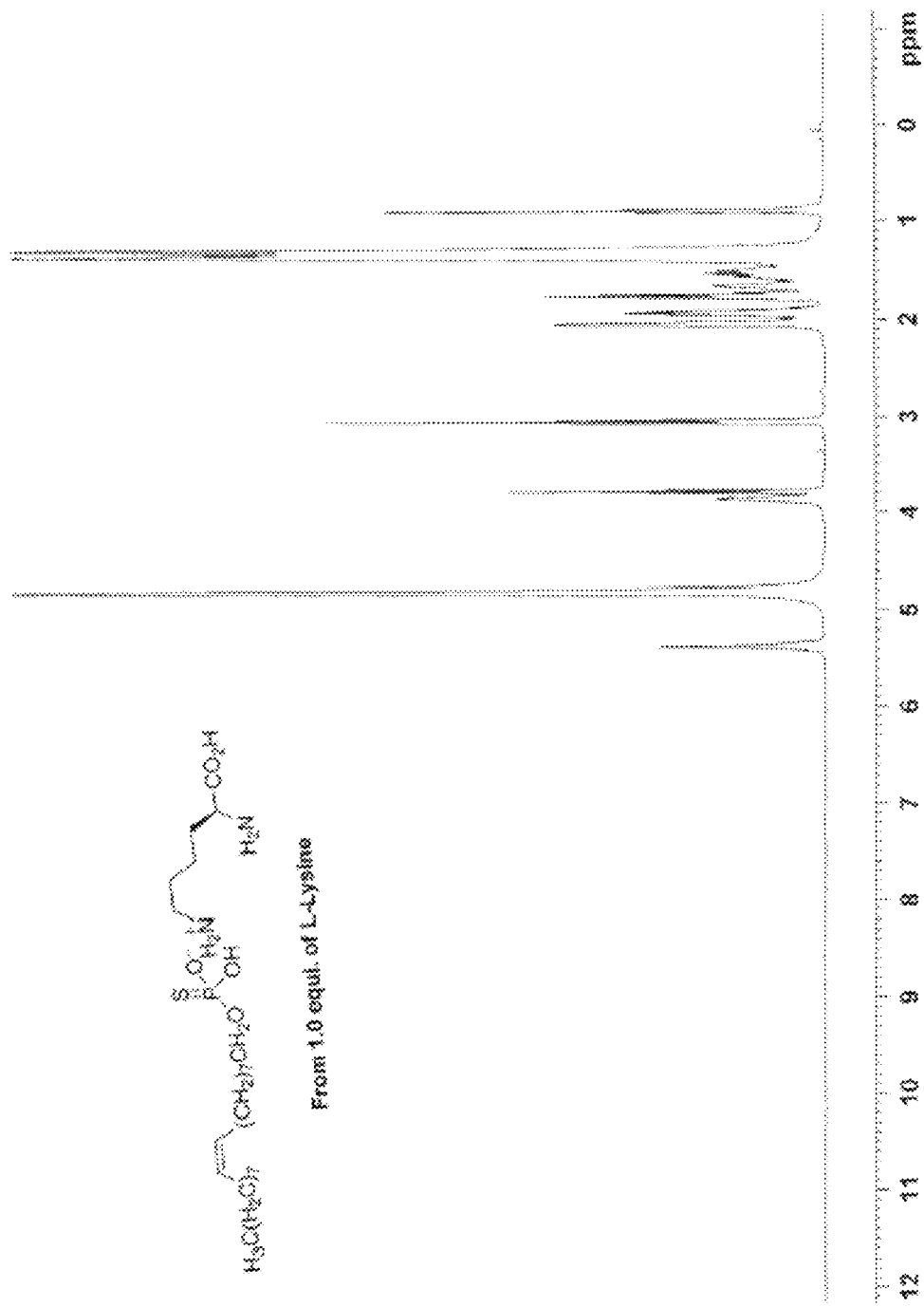
FIG. 2a shows a graph depicting a proton NMR analysis result of Rx100.L-Lysine salt prepared with 1.0 equivalent L-Lysine base.
Figure 2B:
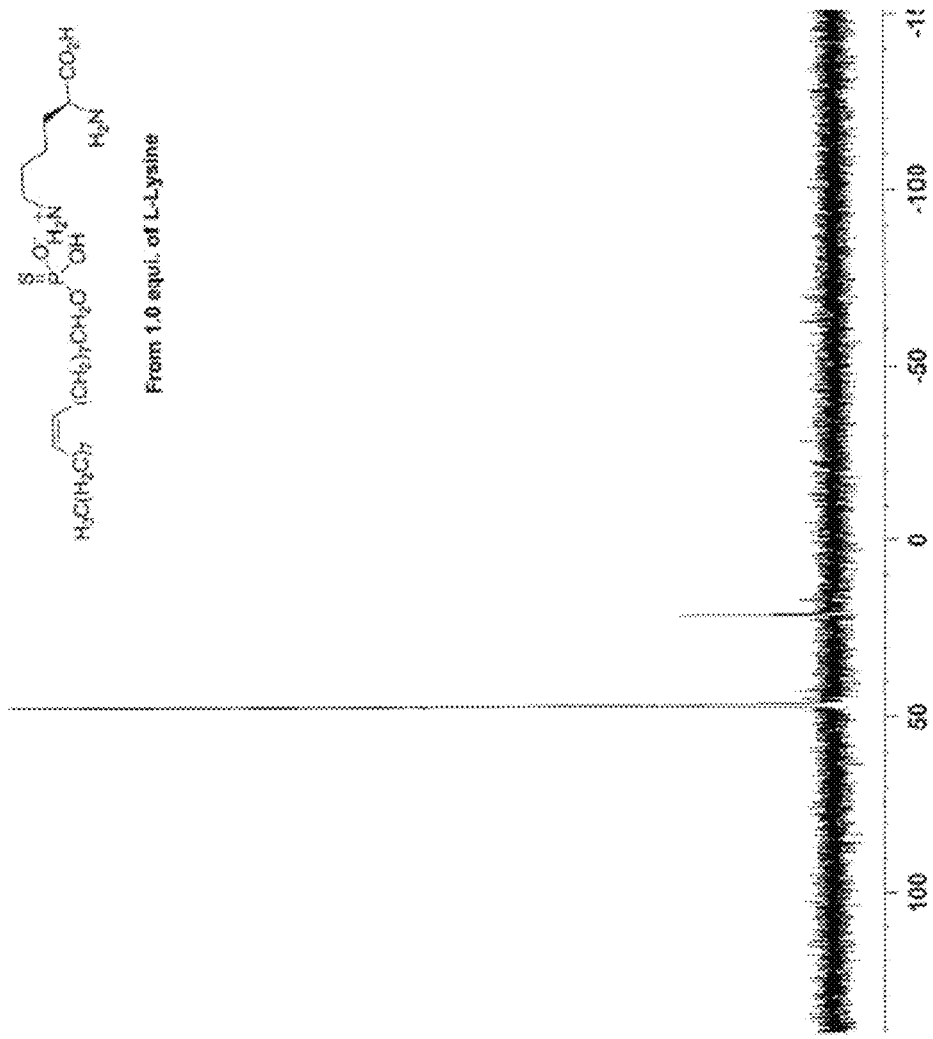
FIG. 2b shows a graph depicting a phosphorus NMR analysis result of Rx100.L-Lysine salt prepared with 1.0 equivalent L-Lysine base.
Figure 3A:
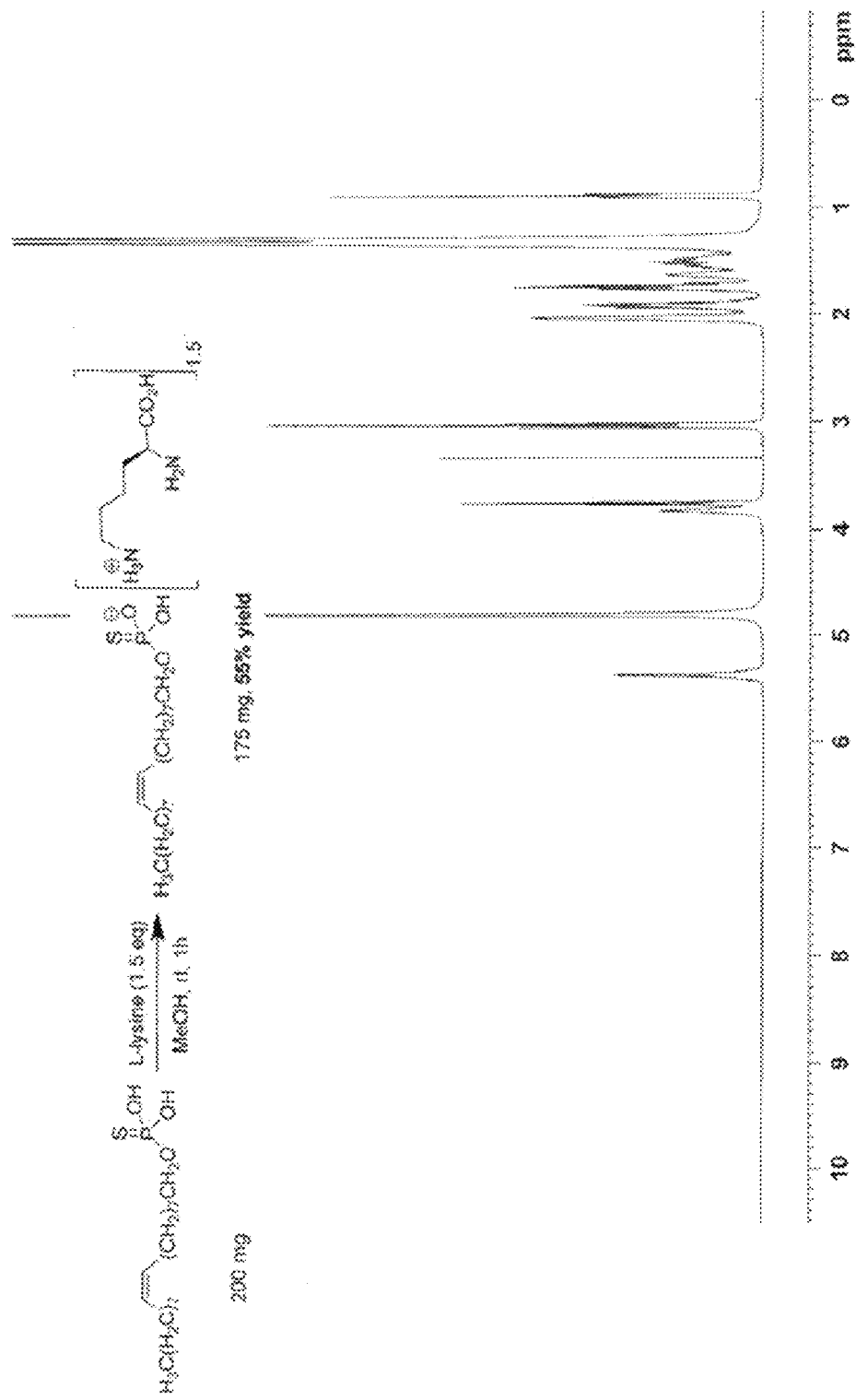
FIG. 3a shows a graph depicting a proton NMR analysis result of Rx100.L-Lysine salt prepared with 1.5 equivalent L-Lysine base.
Figure 3B:
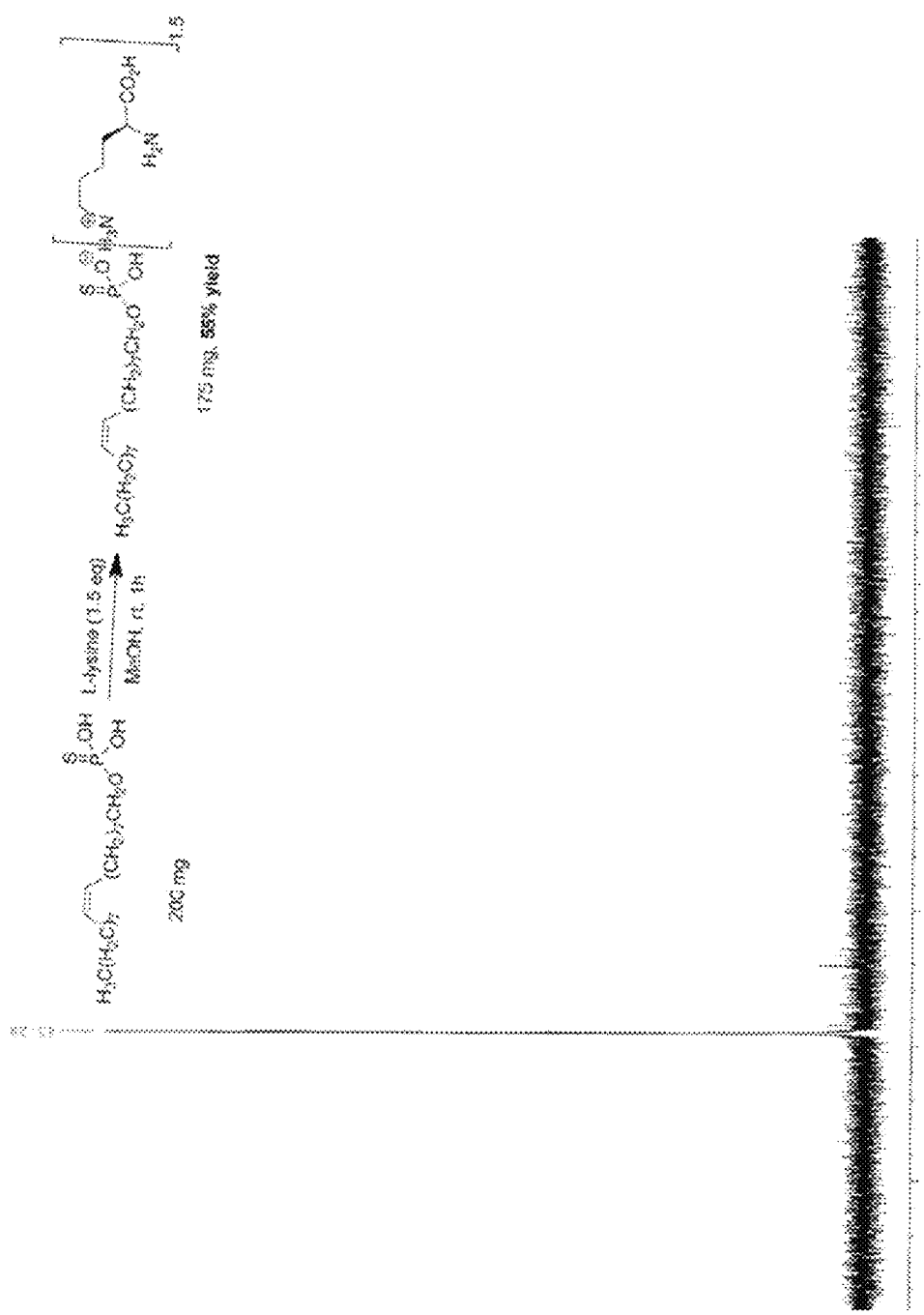
FIG. 3b shows a graph depicting a phosphorus NMR analysis result of Rx100.L-Lysine salt prepared with 1.5 equivalents of L-lysine base.
Figure 4A:
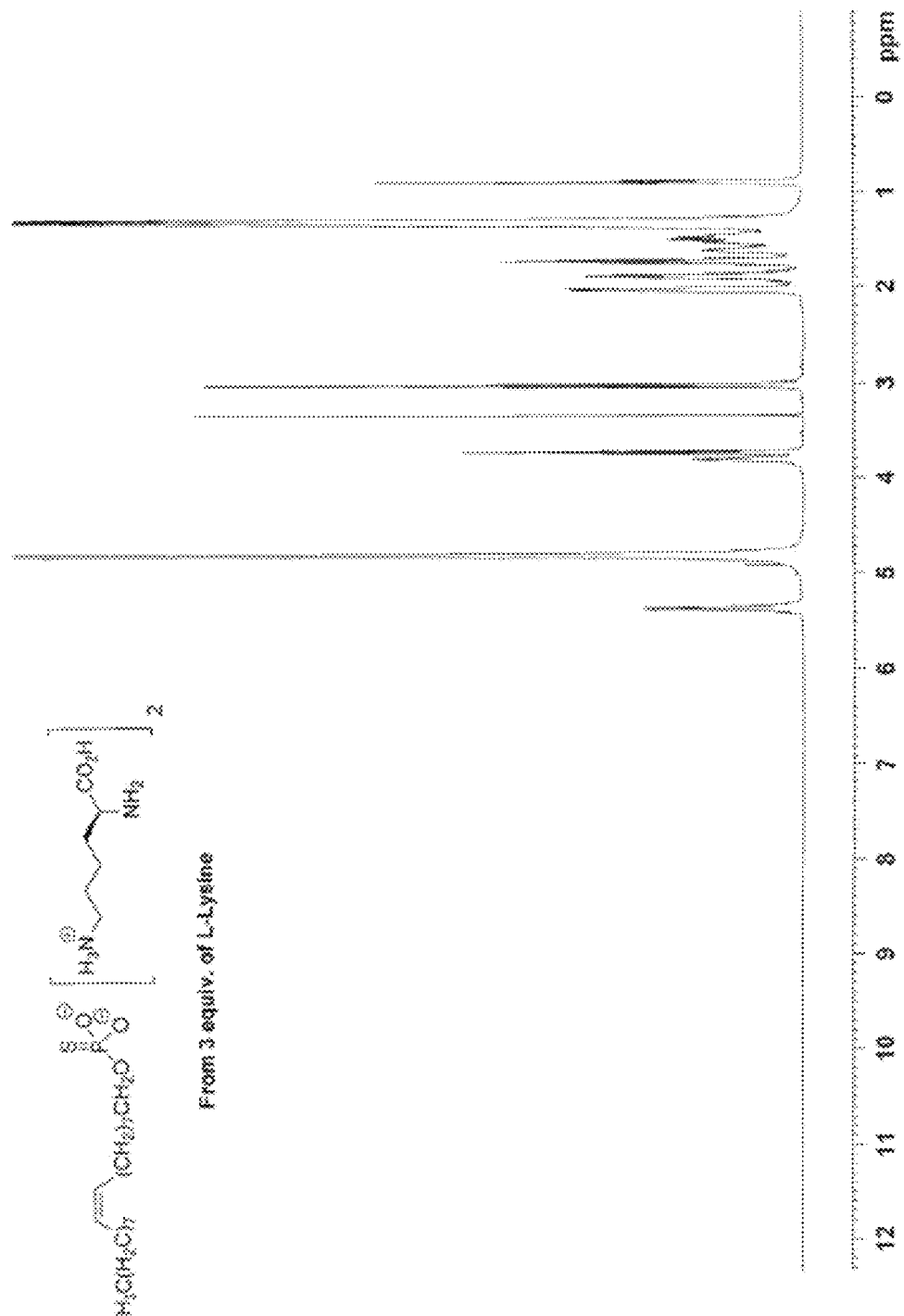
FIG. 4a shows a graph depicting a proton NMR analysis result of Rx100.L-Lysine salt prepared with 3.0 equivalent L-Lysine base.
Figure 4B:
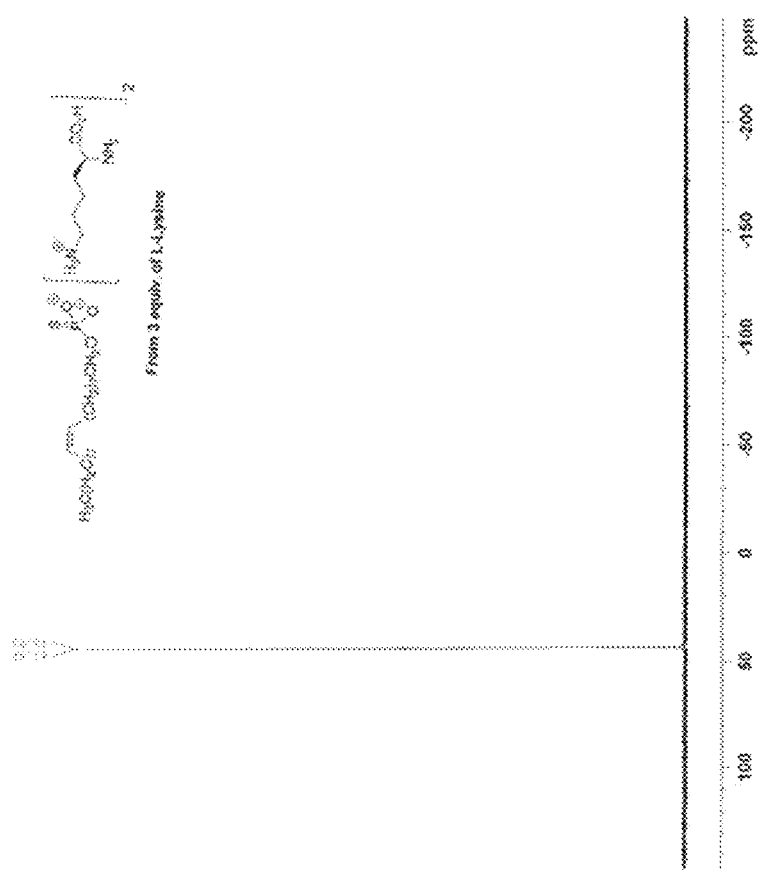
FIG. 4b shows a graph depicting a phosphorus NMR analysis result of Rx100.L-Lysine salt prepared with 3 equivalents of L-lysine base.

Various molar equivalencies of L-Lysine (0.5, 1.1, 1.5 and 2.1) were added to evaluate the impact of equivalency. Rx100.L-Lysine salts at the four different molar equivalencies were obtained according to the same procedure as detailed in Example 1. At 0.5 equivalency, a gummy salt formed. But at 1.0, 1.5, 2.0 and 3.0 equivalencies, filterable solid salts formed. At 1.5 molar equivalency, the Rx100.L-Lysine salt appeared to have a more resolved $^1$H NMR spectrum. FIGS. 1, 2a, 3a and 4a show the $^1$H NMR results of the salts at various L-Lysine equivalents. FIGS. 2b, 3b and 4b show the phosphorus NMR results of the salts at various L-Lysine equivalents. The results indicated that L-Lysine base stoichiometry was at about 2 molar equivalency to Rx100.FA.

2.3 Scaled-Up Preparation of Rx100.L-Lysine Salt Form

The example provides a proof of concept scaled-up Rx100.L-Lysine salt manufacturing. The manufacturing was on 2 gram (g) scale utilizing MeOH:water (8:2) and 1.5 equivalents of L-Lysine at room temperature. Briefly, approximately 2 g of the starting material Rx100.FA was dispensed into a 40 mL glass vial fitted with magnetic stir bar. MeOH (16.11 mL) and water (1.54 mL) were added to the vial and allowed to stir. To this solution, 1.5 molar equivalent of L-Lysine solution (30% L-lysine in water; total 3.54 mL of solution) was added to form a thick white precipitate. This mixture was allowed to equilibrate for approximately 3.5 hours before the solids were filtered and 1.8 g of the Rx100 L-Lysate salt was recovered. Calculating for a sesqui-salt, the yield was determined to be approximately 57% because the theoretical yield was about 3.2 g.

The Rx100.L-Lysine salts were dried overnight under vacuum at 35° C. and then characterized by XRPD, DSC, TGA, $^1$HNMR, Karl Fischer (KF), optical microscopy and moisture sorption assays. All results are summarized in Table 13.

of the salt. Set-A protons are from Rx-100 part of the molecule and set-B protons are from L-Lysine part of the molecule. These two set of protons were selected because they are very well separated from rest of the protons in the $^1$HNMR of the molecule. As shown in the molecular scheme in FIG. 39, set-A protons correspond to two olefinic protons of Rx100 and appear at δ5.2 ppm in the $^1$H NMR. In contrast, set-B protons correspond to methylene of lysine part and appear at δ2.9 ppm. Comparison of $^1$H NMR integration values for set-A and set-B protons indicates the ratio of Rx100 to lysine as 1:1.5.

Figure 7:
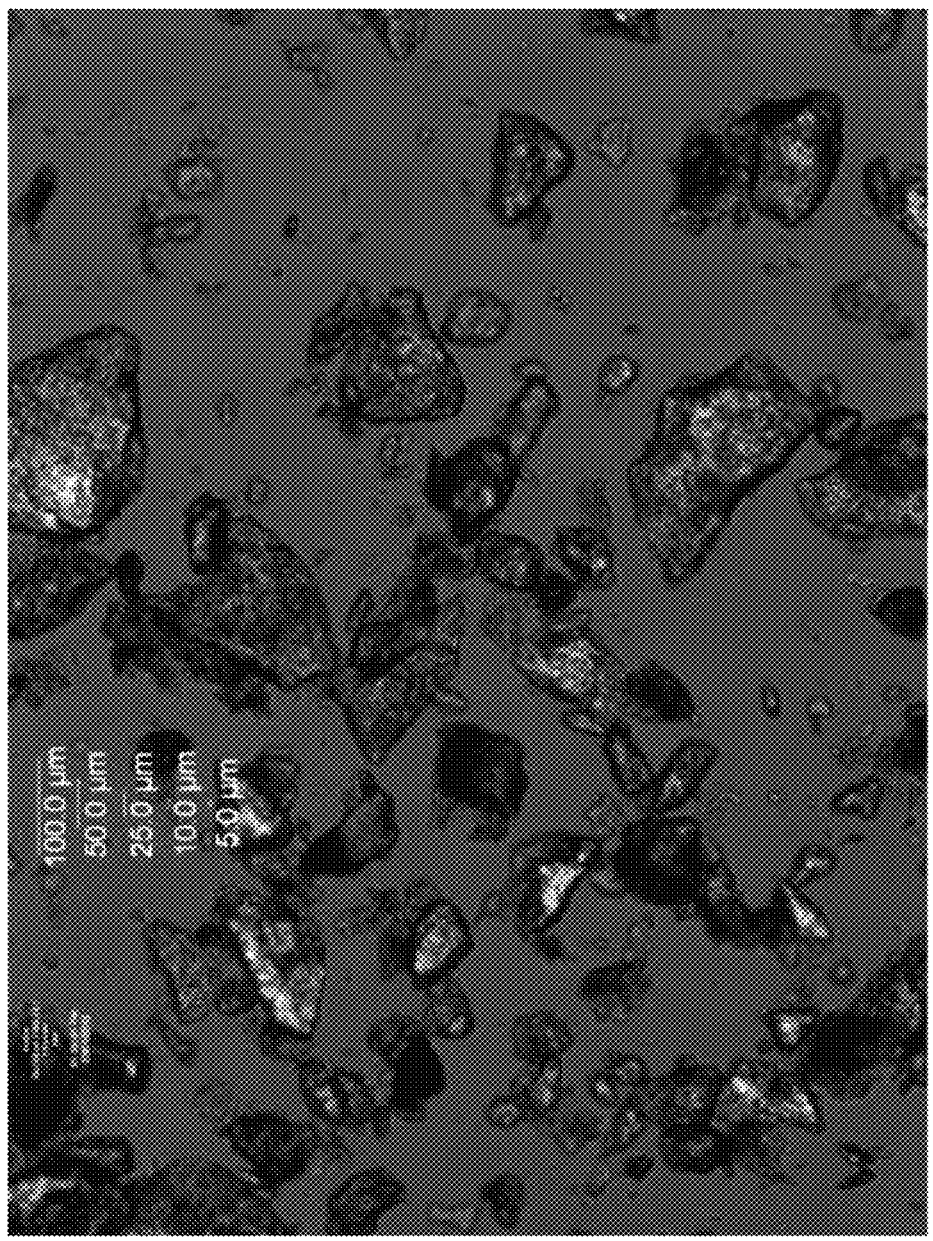
FIG. 7 shows an optical microscopy image of Rx100.L-Lysine salt XRPD Pattern A.
Figure 8:
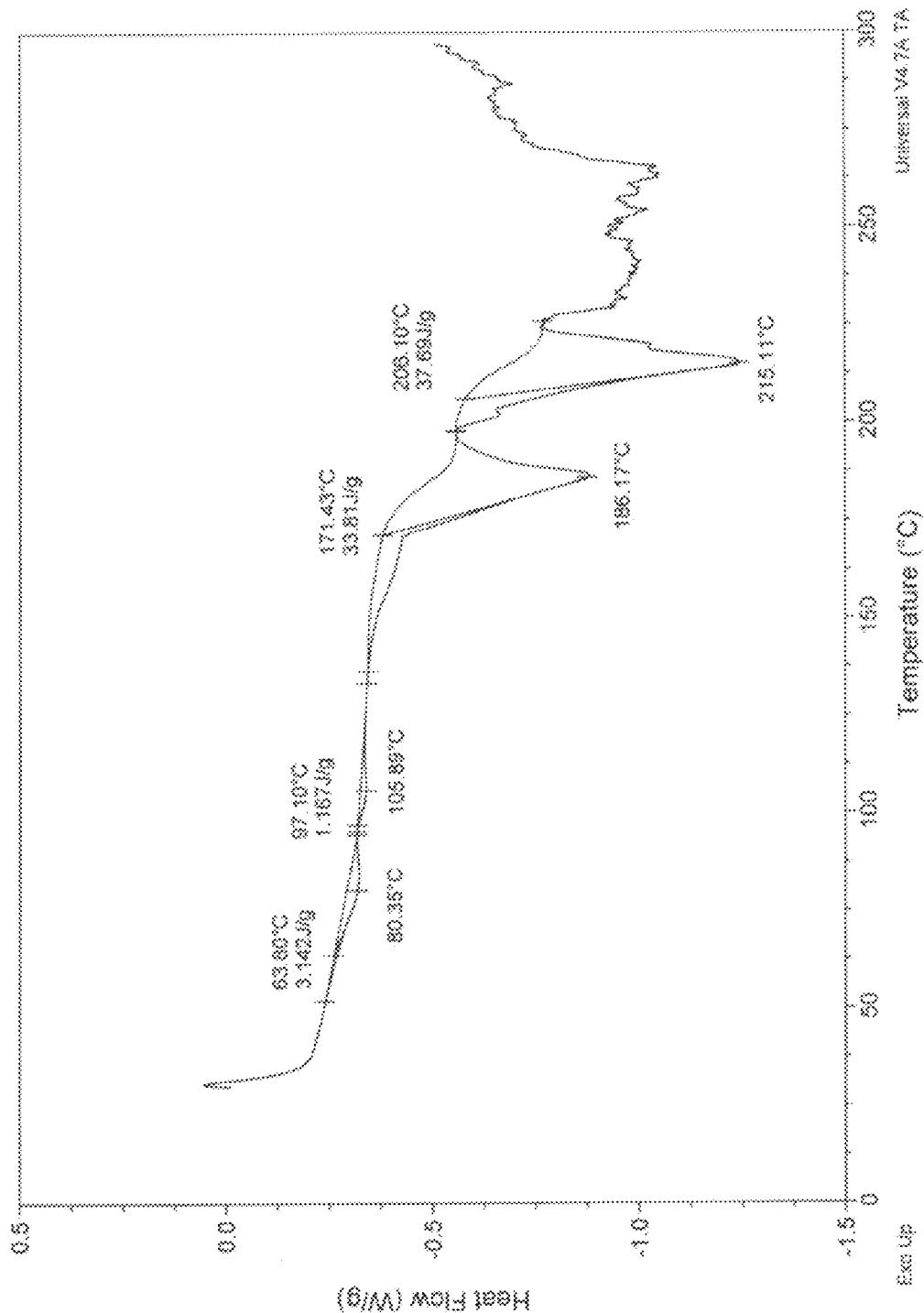
FIG. 8 shows a DSC thermogram of Rx100.L-Lysine salt Pattern A.

As shown in FIG. 7, the morphology of the crystals was determined to be irregularly shaped. The exhibition of birefringence observed by optical microscopy confirmed the crystallinity observed by XRPD As shown in FIG. 8, thermal analysis by DSC showed multiple transitions with endothermic events observed with the major melting peak at 186.2° C. Endothermic events observed at 80.4° C. and 105.9° C. can be attributed to the loss of solvent followed by melting and decomposition at the latter transitions.

Figure 9:
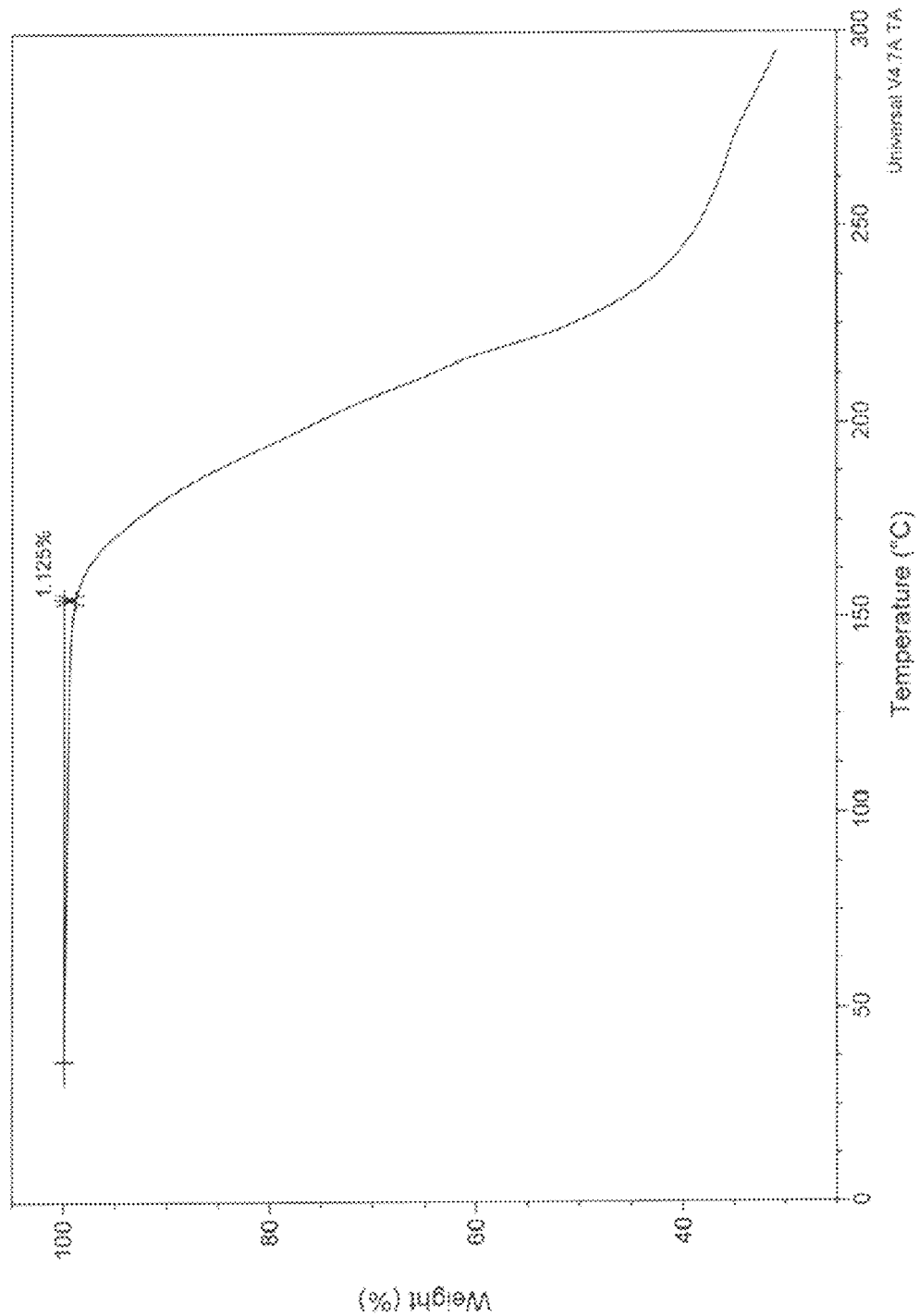
FIG. 9 shows a TGA thermogram of Rx100.L-Lysine salt that has a lot number 1980-18-1 and shows XRPD Pattern A.

As shown in FIG. 9, TGA analysis showed a 1.1% weight loss between 45-155° C., with melting/decomposition observed from 160-300° C. Karl Fischer analysis showed the materials to contain approximately 1.8 wt % water.

TABLE 13

Characterization Summary of Rx100.L-Lysine salt.

| Sample Lot | XRPD [Form] | DSC [° C.] | TGA [% Wt. loss] | $^1$H NMR | KF [Wt % water] | Optical Microscopy | Moisure Sorption [Wt. % at 95% RH] |
|---|---|---|---|---|---|---|---|
| 1980-18-1 | Crystalline [L-Lysine Salt, 10A] (Off-white) | 80.4, 105.9, 186.2, 215.1 | 1.1 | Consistent with structure | 1.8 | Birefringent | 20.6 (reversible) |

Figure 5:
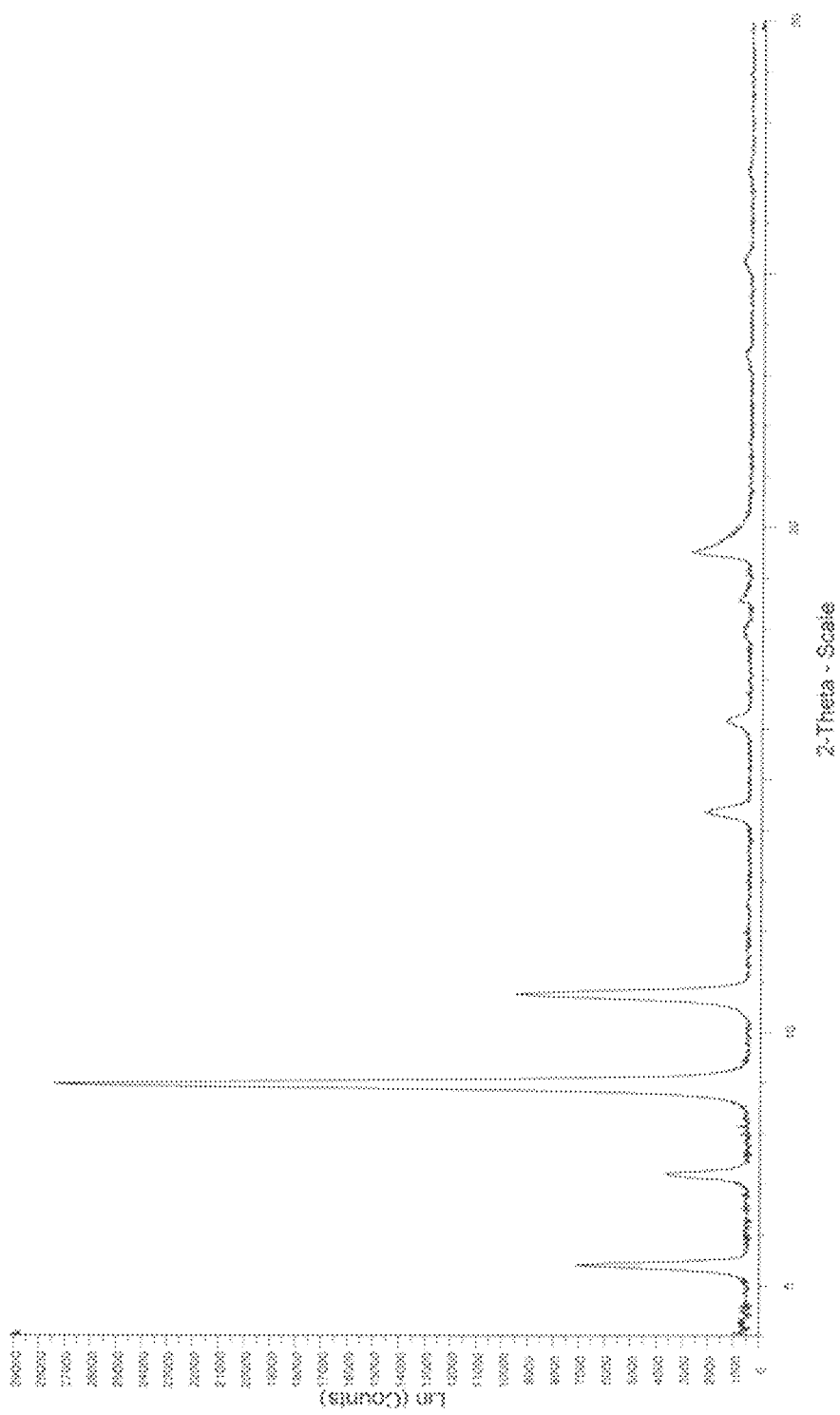
FIG. 5 shows a graph depicting x-ray powder diffraction (XRPD) analysis result of Rx100.L-Lysine salt that has a lot number 1980-18-1 and shows XRPD Pattern A.

As shown in FIG. 5, XRPD analysis of the off-white colored solid was found to afford a crystalline XRPD pattern designated as Pattern A. The parameters are shown in Table 14.

TABLE 14

The parameters identified in the XRPD analysis of the solid.

| 2-Theta | % | count | d |
|---|---|---|---|
| 5.285 | 31.1 | 8177 | 16.70651 |
| 7.074 | 17 | 4461 | 12.48542 |
| 8.834 | 100 | 26289 | 10.00248 |
| 10.618 | 35.1 | 9219 | 8.32537 |
| 14.19 | 8.6 | 2257 | 6.23665 |
| 16.003 | 6.9 | 1823 | 5.53371 |
| 17.787 | 6.7 | 1757 | 4.98246 |
| 18.517 | 10.3 | 2698 | 4.7878 |
| 18.987 | 7.1 | 2255 | 4.6703 |
| 19.404 | 22.5 | 5915 | 4.57088 |
| 23.265 | 4.3 | 1129 | 3.82024 |
| 25.052 | 4.2 | 1117 | 3.55173 |
| 32.852 | 5.9 | 1546 | 2.72402 |

Figure 6:
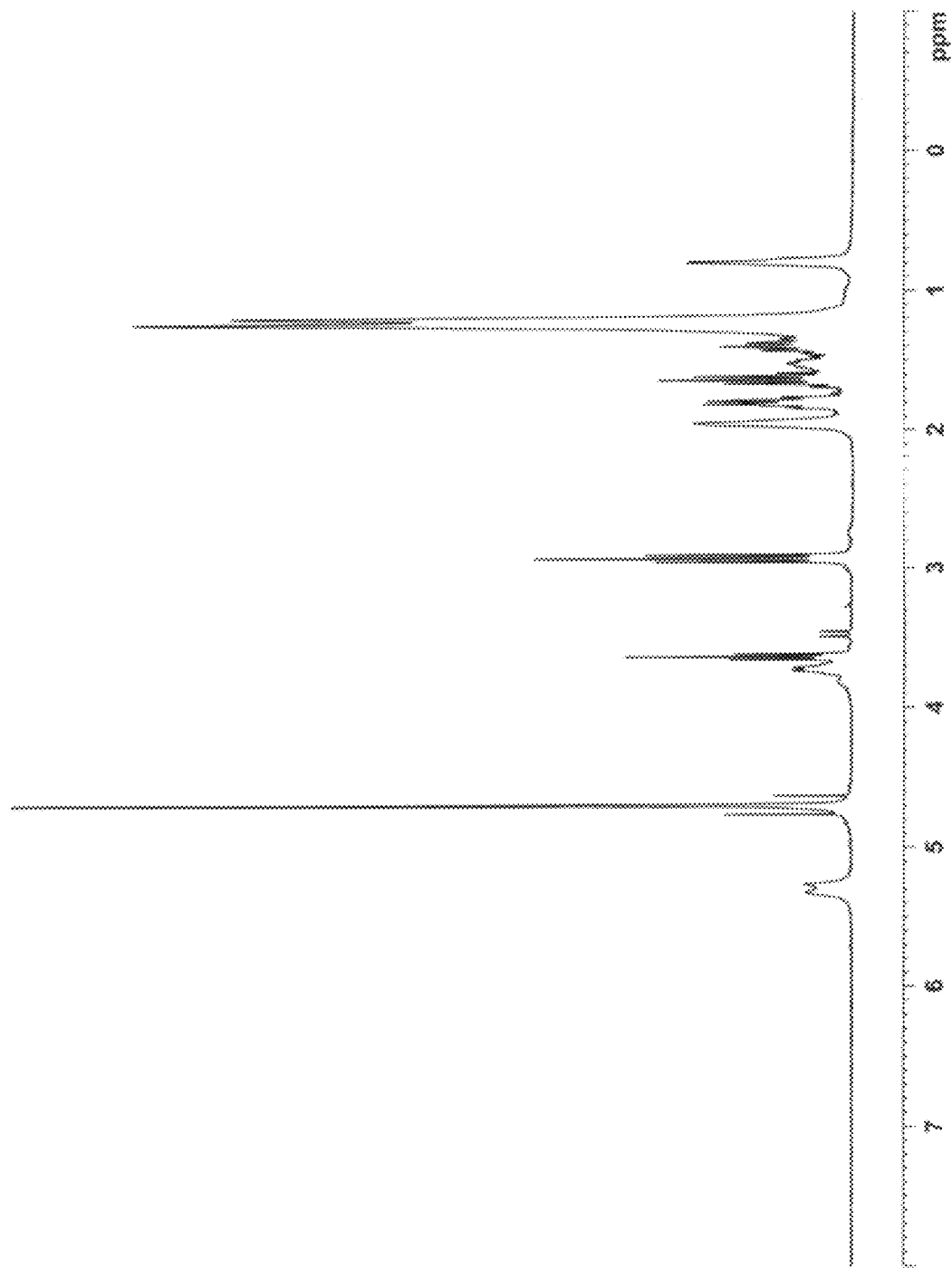
FIG. 6 shows a graph depicting a proton NMR analysis result of Rx100.L-Lysine salt that has a lot number 1980-18-1 and shows XRPD Pattern A.
Figure 10:
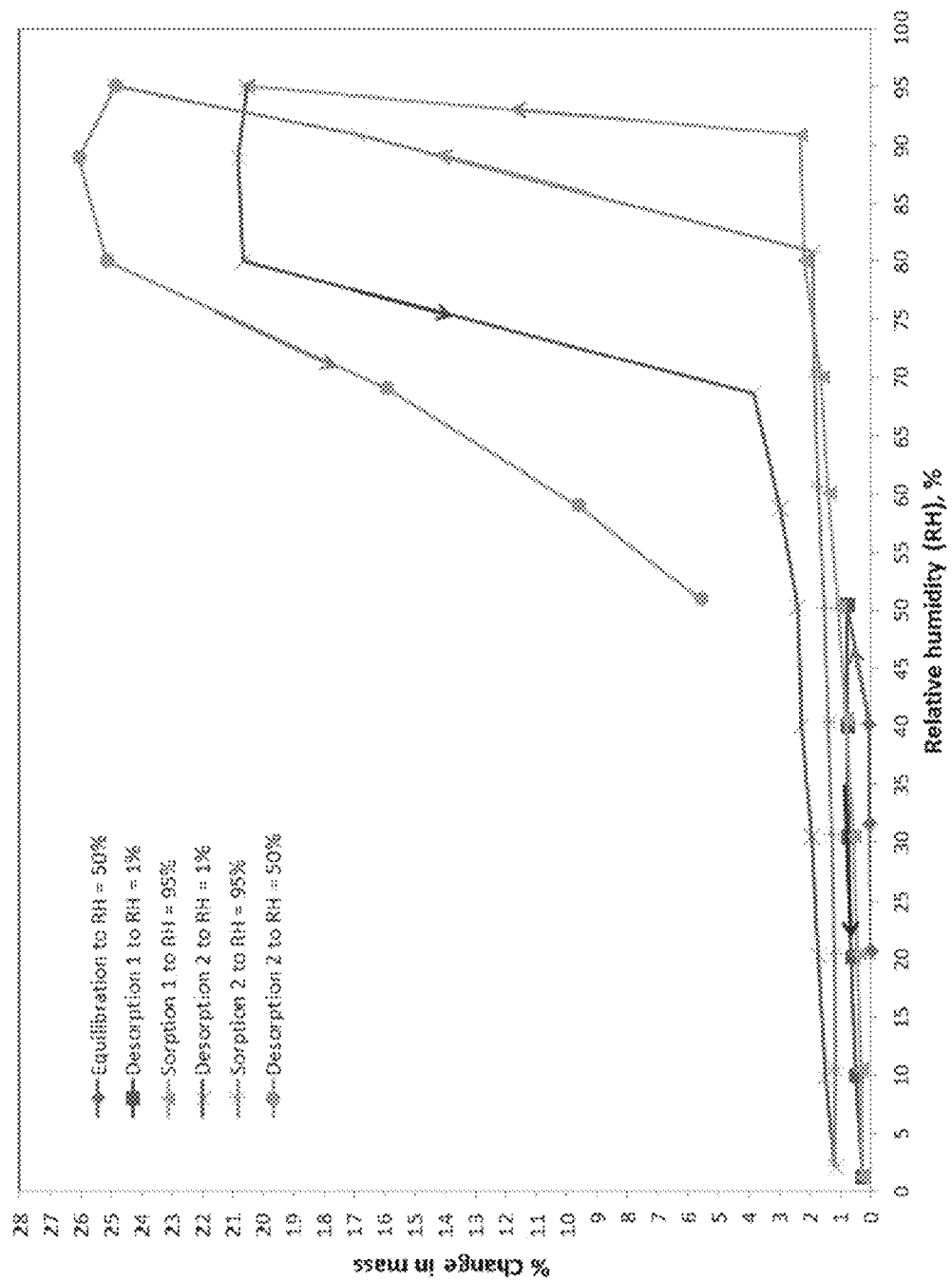
FIG. 10 shows a Gravimetric moisture sorption plot of Rx100.L-Lysine salt that has a lot number 1980-18-1 and shows XRPD Pattern A.

As shown FIG. 6, the analysis by $^1$H NMR showed the L-Lysine salt to be consistent with structure of Rx100 with 1.5 equivalent of L-Lysine. $^1$H NMR of Rx100.lysine in D$_2$O was recorded using 300 MHz NMR instrument. Ratio of Rx-100 to L-Lysine in the salt was calculated based on the $^1$HNMR integration ratio of set-A protons to set-B protons Moisture sorption analysis of the Rx100.L-Lysine salt was performed by equilibrating the sample at 25° C. and 50% RH to simulate ambient lab conditions. Humidity then decreased to 0% RH, increased from 0 to 95% RH, reduced from 95 to 0% RH, increased from 0 to 95% RH and then decreased from 95 to 50% RH. The L-Lysine salt was found to be hygroscopic, adsorbing 20.6% water at 95% RH. Upon desorption, hysteresis was observed as the solids were able to lose the gained moisture as shown in FIG. 10. Based on these data, Rx100.L-Lysine salt is preferably handled at a relative humidity of less than 50-60% and more preferably stored with desiccant.

Figure 11:
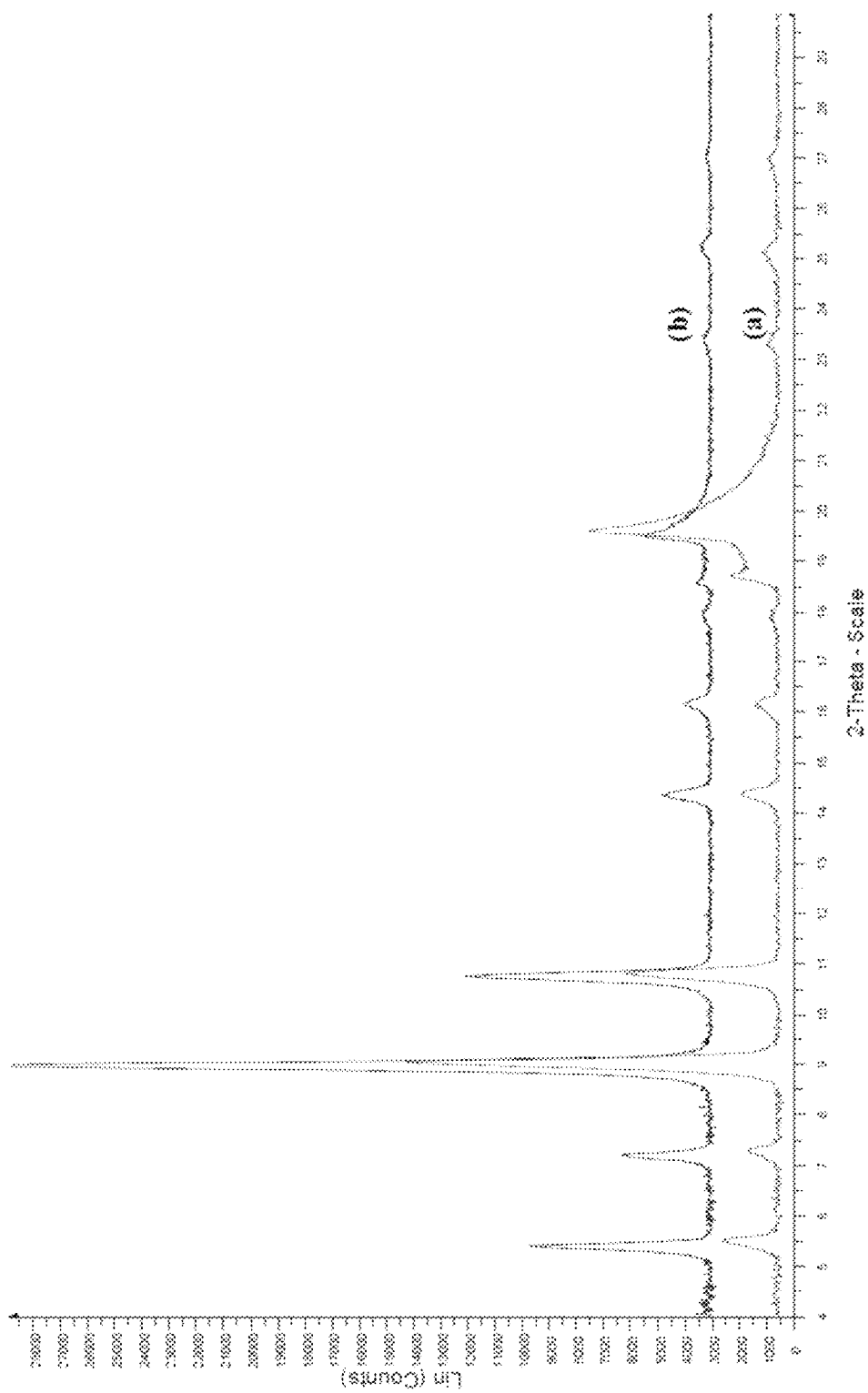
FIG. 11 shows a XRPD stack plot of Rx100.L-Lysine salts that has a lot number 1980-18-1 and shows XRPD Pattern A, (a) before moisture sorption analysis and (b) after moisture sorption analysis.

As shown in FIG. 11, XRPD analysis of the solids following moisture sorption analysis showed no change in form and was consistent with Pattern A.

In addition, the Rx100 L-Lysate salt was further characterized under abbreviated polymorph evaluation. First, the solubility measurement by gravimetric method was performed. Briefly, excess amount of solid was slurried in various solvents at ambient conditions and elevated temperature (50° C.) for minimum of 24 hours. The slurry was centrifuged using a temperature controlled centrifuge and the supernatant was used for gravimetric method. Table 15 presents the solubility data measured using this gravimetric method in various solvents for the L-Lysine salt. In cases where the solvent dissolved all of the solid, the value is shown as "greater than".

TABLE 15

Solubility of Rx100.L-Lysine Salt in various solvent systems using the gravimetric method.

| 1980- | Solvent | mg/mL at 25° C. | mg/mL at 50° C. |
|---|---|---|---|
| 19-1, 20-1 | *IPA:water (v/v) [3:7] | >46 | >70 |
| 19-2, 20-2 | *IPA:water (v/v) [1:1] | >40 | >86 |
| 19-3, 20-3 | *IPA:water (v/v) [7:3] | Gelled | Gelled |
| 19-4, 20-4 | *EtOH:water (v/v) [3:7] | >40 | >84 |
| 19-5, 20-5 | *EtOH:water (v/v) [1:1] | Gelled | >68 |
| 19-6, 20-6 | *EtOH:water (v/v) [7:3] | Gelled | Gelled |
| 19-7, 20-7 | *MeOH:water (v/v) [3:7] | >48 | >86 |
| 19-8, 20-8 | *MeOH:water (v/v) [1:1] | Gelled | >80 |
| 21-1 | MeOH:water (v/v) [7:3] | 20 | Gelled |
| 21-2, 21-7 | Heptane | — | 3 |
| 21-3, 21-8 | MTBE | — | 4 |
| 21-4, 21-9 | IPA | — | 5 |
| 21-5, 21-10 | EtOH | — | 3 |
| 21-6, 21-11 | MeOH | — | 4 |
| 19-15, 20-15 | *Water | >48 | >76 |

*All solids fully dissolved and used for evaporative crystallizations
*indicated that all solids fully dissolved and used for evaporative crystallizations.

Figure 12:
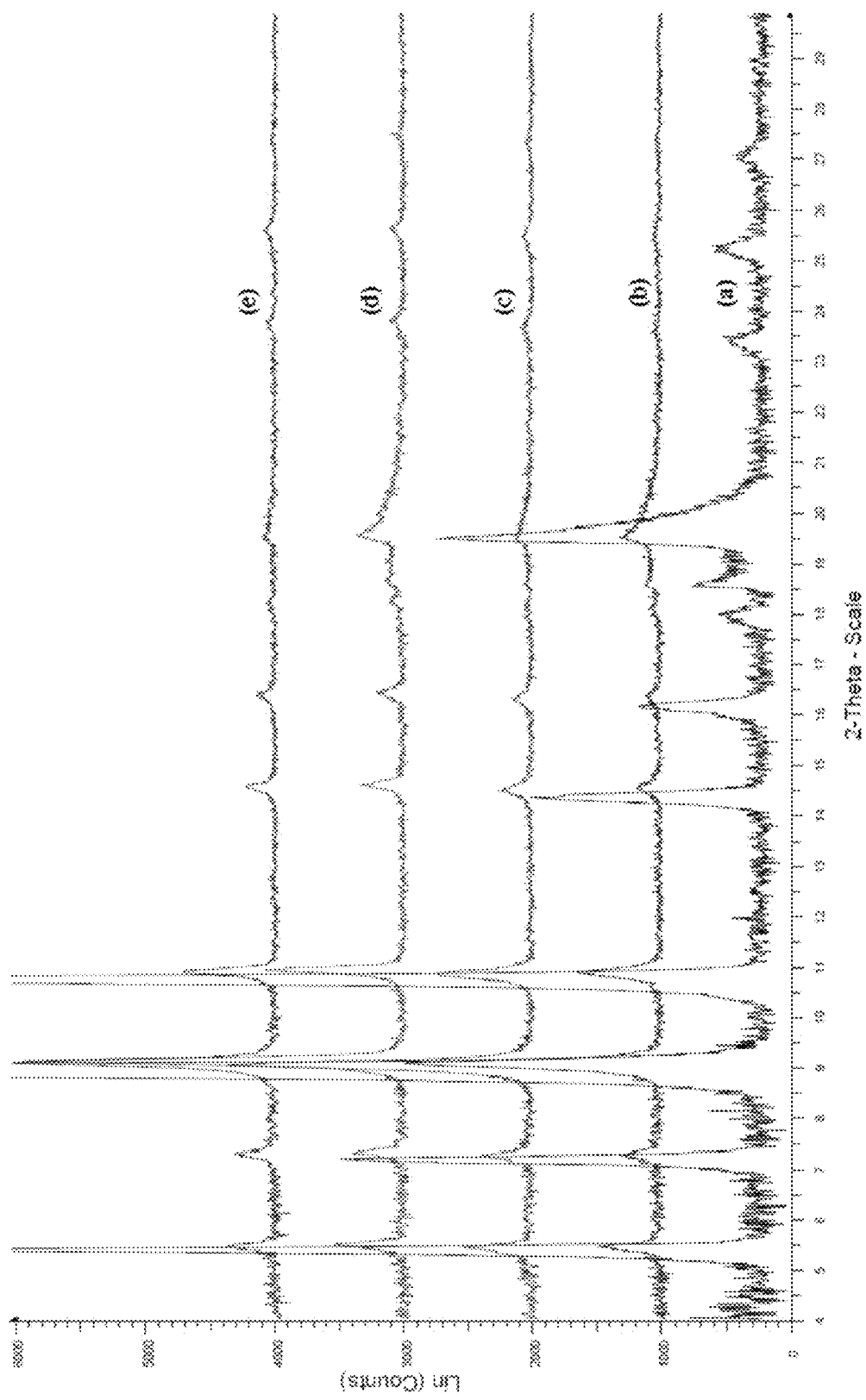
FIG. 12 shows a XRPD stack plot of Rx100.L-Lysine salts isolated from short term slurries (a) lot number 1980-18-1, Pattern A, (b) lot number 1980-19-14 dry, isolated from slurry in methanol at 25° C. after drying, (c) lot number 1980-19-14 wet, isolated from slurry in Methanol at 25° C., (d) lot number 1980-20-14 dry, isolated from slurry in methanol at 50° C. after drying and (e) lot number 1980-20-14 wet, isolated from slurry in Methanol at 50° C.

Second, short term slurry tests were performed. Rx100.L-Lysine salt was slurried for a minimum of 24 hours in 15 different solvent systems at two different temperatures (25 and 50° C.) in an attempt to provide information for crystallization experiments and design of polymorph screening experiments. A 48 position Chemglass reaction block was used for heating and stirring the slurries which were in 2 mL HPLC vials. After the due time, vials were centrifuged and the wet solids were used for X-ray diffraction. The wet solids were dried and re analyzed by XRPD which showed no change in form and was consistent with Pattern A as shown in FIG. 12. Table 16 summarizes the results of the short term slurry experiments.

TABLE 16

Summary of a 24 hour slurry of Rx100. L-Lysine Salt.

| | | | 25° C. | | 50° C. | |
|---|---|---|---|---|---|---|
| 1980- | Solvent | Starting Form | Resulting Form, Wet | Resulting Form, Dry | Resulting Form, Wet | Resulting Form, Dry |
| 19-9, 20-9 | MeOH:water (v/v) [7:3] | A | A | A | — | — |
| 19-10, 20-10 | Heptane | A | A | A | A | A |
| 19-11, 20-11 | tBME | A | A | A | A | A |
| 19-12, 20-12 | IPA | A | A | A | A | A |
| 19-13, 20-13 | Ethanol | A | A | A | A | A |
| 19-14, 20-14 | Methanol | A | A | A | A | A |
| 19-15, 20-15 | Water | A | | Dissolved | | |

Figure 13:
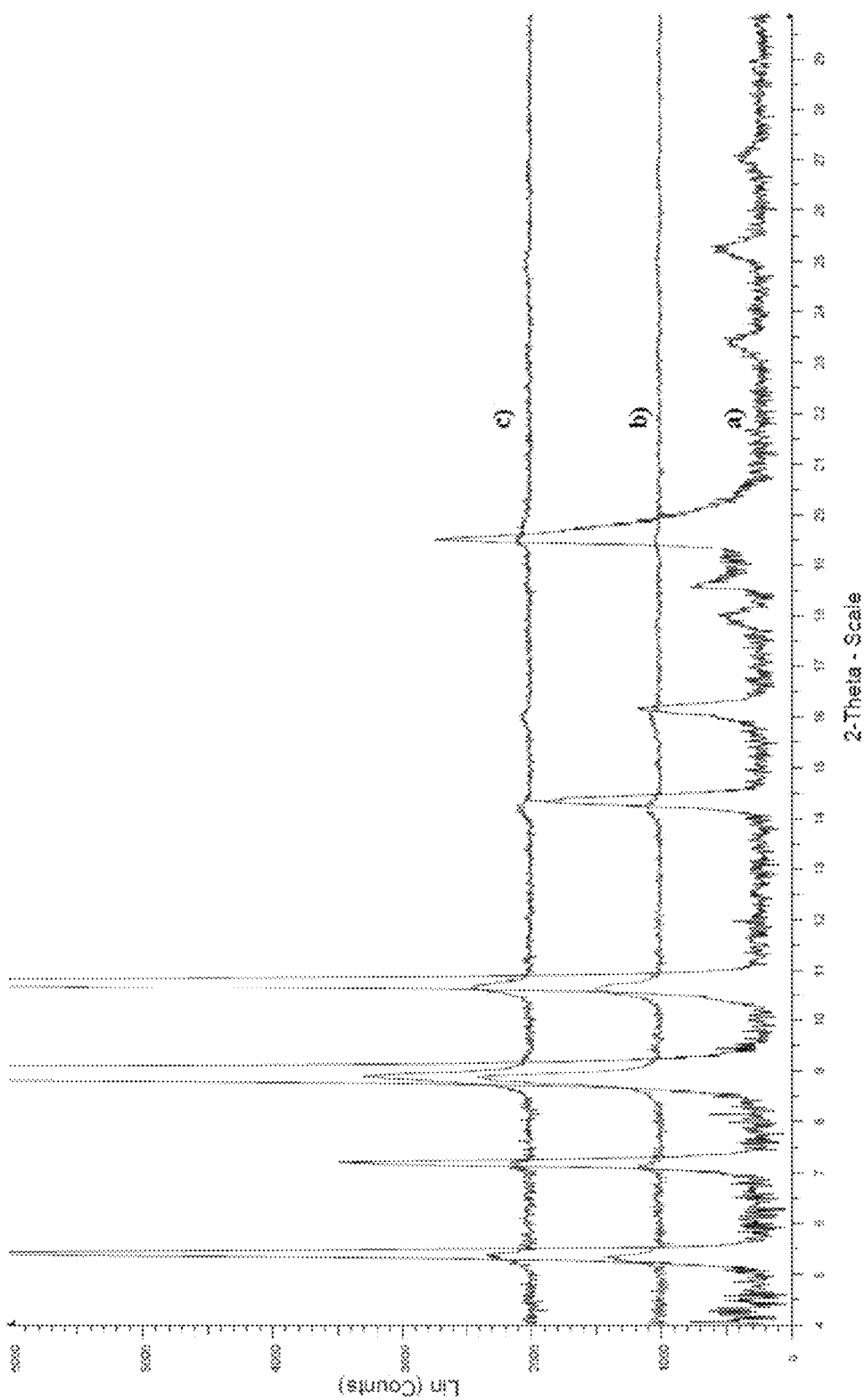
FIG. 13 shows a XRPD stack plot of Rx100.L-Lysine salts isolated from evaporative crystallizations (a) lot number 1980-18-1, Pattern A, (b) lot number 1980-19-8 Evap, isolated from evaporative crystallization from methanol.

Third, Evaporative Crystallization tests were performed. Based on the short term slurry experiments, all samples which experienced full dissolution were utilized for evaporative crystallizations. Samples were evaporated to dryness under vacuum at ambient conditions. XRPD analysis of the evaporated solids showed no change in form from the starting material, Pattern A as shown in FIG. 13. Table 17 summarizes the results of the evaporative crystallization experiments.

TABLE 17

Summary of Evaporative Crystallization Experiments of Rx100. L-Lysine Salt.

| 1980- | Solvent | Starting Form | 25° C. Resulting Form, Dry | 50° C. Resulting Form, Dry |
|---|---|---|---|---|
| 19-1, 20-1 | IPA:water (v/v) [3:7] | A | A | A |
| 19-2, 20-2 | IPA:water (v/v) [1:1] | A | A | A |
| 19-3, 20-3 | IPA:water (v/v) [7:3] | A | A | A |
| 19-4, 20-4 | EtOH:water (v/v) [3:7] | A | A | A |
| 19-5, 20-5 | EtOH:water (v/v) [1:1] | A | A | A |
| 19-6, 20-6 | EtOH:water (v/v) [7:3] | A | A | A |
| 19-7, 20-7 | MeOH:water (v/v) [3:7] | A | A | A |
| 19-8, 20-8 | MeOH:water (v/v) [1:1] | A | A | A |
| 20-9 | MeOH:water (v/v) [7:3] | A | — | A |
| 19-15, 20-15 | Water | A | A | A |

EXAMPLE 3

Process Development 3.1 Evaluation of the Process Variables that were Suspected to Influence the Quantity of Impurities in the Two Step Synthesis and Purification of Rx100.FA.

We evaluated the process variables that were suspected to influence the quantity of impurities in the two step synthesis and purification of Rx100.FA in Scheme III FIG. 38. This study was performed at 5 g batch synthesis. The variable process factors were reaction temperature in reaction Step 1, and the stoichiometry of triethylamine and sodium hydroxide used in reaction Step 2. In step 1, the union of pyridine and thiophosphoryl chloride prior to the addition of cis-oleyl alcohol produces a heterogeneous solution which upon stirring turns clear. The length of time it takes the solution to turn clear was suspected to be temperature dependent, but to vary this factor and include it in the study design would dramatically increase the number of runs so we waited until the solution turned clear (a process control point held constant) prior to addition of cis-oleyl alcohol and recorded the time. The temperature variables were −20 & 0° C. and 0 & 25° C. The reagents were added and mixed at the lower temperature until clear then warmed to the second temperature at which time cis-OA was added and mixed for the duration of the experiment. In Step 2, TEA and NaOH equivalences were independently varied. TEA was varied from 0.5 to 2 equivalence, while NaOH was varied from 2 to 3 equivalence of intermediate (IM).

The design of experiments (DOE) used to capture the data was a full factorial design with center points (12 runs total) using the factor settings in outlined in Table 18. Data was analyzed using commercial software 'Stat-Ease' (http://www.statease.com/).

TABLE 18

Factors and settings used in the 2-level full factorial DOE.

| Factor | Name | Units | Type | Minimum | Maximum |
|---|---|---|---|---|---|
| A | Step 1 Reaction Temp profile | °C. | Categorical | −20/0° C.* | 0/25° C.* |
| B | TEA level | eq | Numeric | 0.5 | 2 |
| C | NaOH level | eq | Numeric | 2 | 3 |

*Two reagents added and mixed at the first temperatute listed; then waited until the mixture turned clear (20-45 minutes); then cis-oleyl alchohol added at the second temperature; after addition the reaction was allowed to warm to room temperature (20-25° C.).

Six and twelve responses were collected during the process or on samples generated from Step 1 and 2, respectively. The four main responses that were statistically significant are: (Response 1, or R1) amount of impurities collected in alkaline wash during Step 2; (Response 2, or R2) level of impurities in Rx100 (drug) detected by $^{31}$P-NMR; (Response 3, or R3) percentage of impurity Rx103 (trans isomer of Rx100) in Rx100 by HPLC-CAD, and (Response 4, or R4) percentage of unknown impurity at RT=5 minutes in Rx100 by HPLC-CAD. These four responses all showed the same trends which should result in the ability to decrease the impurities in the reactions.

Factors Affecting Amount of Impurities in Alkaline Wash Following Hydrolysis.

This response reports the quantity (grams) of impurities is captured in the Alkaline extraction. If more impurities are captured, they are not allowed into the final product, which is a good thing. However, capturing more impurities also indicates that more impurities were produced, and the goal is to decrease impurities, so lower impurities are better. FIG. 14 is a Pareto chart showing the largest effects from left to right. Any effect above the red (Bonferonni) line is most likely significant using a corrected (Bonferroni) t-test. Any effect falling above the black (t-value limit) could be significant. Anything below both lines (like effect 3 in FIG. 1), is most likely not significant. In this case, factors A and B are likely significant, while the 3rd effect (which in this case was factor C) is most likely insignificant.

To determine if the effects, and the model, are actually significant, an Analysis of Variance (ANOVA) was conducted. The results for the ANOVA on R1 are presented in Table 19. Here, you can see that the model is significant (p-value <0.05) and both the A effect and B effect are very significant. These terms were used in the model, from which FIGS. 15 and 16 are drawn.

TABLE 19

ANOVA for R1. A and B are significant, indicated by the low p-values.

| Source | Sum of Squares | df | Mean Square | F Value | p-value Prob> | |
|---|---|---|---|---|---|---|
| Model | 1.106 | 2 | 0.55 | 23.06 | 0.0015 | significant |
| A-Temp | 0.357 | 1 | 0.36 | 14.88 | 0.0084 | |
| B-TEA | 0.714 | 1 | 0.71 | 29.77 | 0.0016 | |
| Curvature | 0.004 | 1 | 0.00 | 0.17 | 0.6960 | not |

TABLE 19-continued

ANOVA for R1. A and B are significant, indicated by the low p-values.

| Source | Sum of Squares | df | Mean Square | F Value | p-value Prob> | |
|---|---|---|---|---|---|---|
| Residual | 0.144 | 6 | 0.02 | | | |
| Lack of Fit | 0.143 | 5 | 0.03 | 63.76 | 0.0948 | not |
| Pure Error | 0.000 | 1 | 0.00 | | | |
| Cor Total | 1.254 | 9 | | | | |

FIG. 15 shows the effect of the Step 1 temperature profile (Factor A) on the impurities in the alkaline wash R1 from Step 2. It is clear that lower Step 1 reaction temperatures are desirable to lower the impurities in the alkaline wash. FIG. 16 shows that higher levels of TEA also had the effect of lowering the impurities in the alkaline wash. The graphs model around 85% of the variation in the data, as indicated by the adjusted R^2 of 0.85 and pred. R^2 of 0.72 which were reported. This indicates a very strong model with little noise.

Factors Affecting Level of Impurities in Drug by P-NMR.

Response 2 was the level of impurities in Drug, which was measured by P-NMR. FIG. 17 is the Pareto chart of effects for this response. B and C are clearly the largest effects. As shown in Table III that these effects were significant, as indicated by the low p-values. So, factors B-TEA and C—NaOH, had a significant effect on the impurities in the Drug.

TABLE 2

ANOVA for R2. B and C are significant, indicated by the low (<0.05) p-values.

| Source | Sum of Squares | df | Mean Square | F Value | p-value Prob> | |
|---|---|---|---|---|---|---|
| Model | 42.25 | 2 | 21.125 | 19.13 | 0.0025 | significan |
| B-TEA | 21.125 | 1 | 21.125 | 19.13 | 0.0047 | |
| C-NaOH | 21.125 | 1 | 21.125 | 19.13 | 0.0047 | |
| Curvature | 15.625 | 1 | 15.625 | 14.15 | 0.0094 | significan |
| Residual | 6.625 | 6 | 1.1042 | | | |
| Lack of Fit | 6.625 | 5 | 1.325 | | | |
| Pure Error | 0 | 1 | 0 | | | |
| Cor Total | 64.5 | 9 | | | | |

These effects are shown in the graph in FIGS. 18 and 19. These graphs model around 56% of the variation in the data, as indicated by the adjusted R^2 of 0.56 and predicted R^2 of 0.40. The other half of the data appears to be random noise, but the trends are still valid and strong, with the low p-values. FIG. 18 shows that more TEA decreases the level of impurities in Drug, a desirable effect. FIG. 19 shows that higher levels of NaOH should also be used to decrease impurities.

Factors Affecting Percentage of Impurity Rx103 in Rx100 by HPLC-CAD.

Response 3 is the percentage of impurity Rx103 in Drug as detected using High Performance Liquid Chromatography (HPLC). The largest effect for this response was factor A, as shown in FIG. 20. Here, it is seen that factor A is the largest and probably significant. However, the next largest effect, which was C, does not appear to be significant.

To test the significance, look at the ANOVA presented in Table 21. The low p-value for the model and factor A indicate they are significant. To see the modeled effect of A, see FIG. 21. Here, you can see that a higher temperature produces more impurities, so a lower temperature profile is desired. For this model, the adj. R^2 of 0.49 and pred. R^2 of 0.29 indicate that the model is explaining about half of the total variation in the response. This is adequate to predict the trend in the data.

TABLE 21

ANOVA for R3. Factor A is significant, indicated by the low (<0.05) p-value.

| Source | Sum of Squares | df | Mean Square | F Value | p-value Prob > F | |
|---|---|---|---|---|---|---|
| Model | 0.7504 | 1 | 0.7504 | 9.559 | 0.0148 | Significant |
| A-Temp profile | 0.7504 | 1 | 0.7504 | 9.559 | 0.0148 | |
| Residual | 0.62801 | 8 | 0.0785 | | | |
| Lack of Fit | 0.49281 | 7 | 0.0704 | 0.521 | 0.7916 | not |
| Pure Error | 0.1352 | 1 | 0.1352 | | | |
| Cor Total | 1.37841 | 9 | | | | |

Factors Affecting Percentage of Impurity 50 (HPLC RT at 5 Minutes).

Response 4 (R4) was the percentage of impurity 50 (HPLC RT at 5 minutes). Again, the goal with this response is to minimize it. FIG. 22 shows the size of the effects in this design. Factors C and B were the largest effects and look like they will be significant. The ANOVA in Table 22 confirms this is the case.

TABLE 22

ANOVA table for R4 (% impurity 50).

| Source | Sum of Squares | df | Mean Squares | F Value | p-value Prob > F | |
|---|---|---|---|---|---|---|
| Model | 19.6616 | 2 | 9.8308 | 65.819 | <0.0001 | significant |
| B-TEA | 6.42611 | 1 | 6.4261 | 43.024 | 0.0006 | |
| C-NaOH | 13.2355 | 1 | 13.236 | 88.615 | <0.0001 | |
| Curvature | 4.0259 | 1 | 4.0259 | 26.954 | 0.0020 | significant |
| Residual | 0.89616 | 6 | 0.1494 | | | |
| Lack of Fit | 0.88896 | 5 | 0.1778 | 24.693 | 0.1516 | not |
| Pure Error | 0.0072 | 1 | 0.0072 | | | |
| Cor Total | 24.5837 | 9 | | | | |

FIGS. 23 and 24 show the effects of B and C on the % impurity 50 response (R4). The high level of TEA and high level of NaOH decreased the amount of impurities.

Therefore, Factor A (reaction temperature in Step 1) showed a positive effect of temperature on the percent impurity Rx103 (trans isomer of Rx100) observed in the drug substance; figure not shown. Both Factors B and C (TEA and NaOH concentration in Step 2) showed a negative effect of base concentration on the amount of unknown impurity (Retention Time=5 minutes).

The goal of this experiment was to learn more about the conditions that would minimize impurities created in the reaction process. Review of all four responses with significant process factors indicate that a lower temperature range should be used in Step 1 during the activation of the $PSCl_3$-pyridine complex and addition of cis-oleyl alcohol, and that a high level of NaOH (3 eq) and TEA (2 eq) should be used to minimize impurities. Higher levels of sodium hydroxide and triethylamine reduce the duration of the reaction and therefore reduce the amount of by-products.

3.2 IM (2) Stability During Acid Wash in Step 1.

IM (2) stability in the acid wash (1N HCl solution) was evaluated by 1H- and 31P NMR and HPLC over various time points (30, 60, 90, 120 and 180 minutes). See Scheme IV in FIG. 40. Step 1 reaction and stability monitoring of IM in 1N hydrochloride acid solution. The results indicated that the no new impurities were observed during the 3 hours of stability monitoring time.

3.3 Rx100 Stability in Alkaline Wash.

During the synthesis of the first of three 20 g batches (mentioned in Section 6.2.4), crude Rx100 from aqueous phase was extracted three times with IPAc to remove non-acidic impurities. During the first extraction, the aqueous layer was sampled at 15 and 30 minutes. During the second and third extraction, the aqueous layer was sampled after 45 minutes. There was no difference in the drug and impurity content between the first extraction samples. However, the amount of known impurities (Rx200 and Rx103, the phosphate and trans isomer of Rx100) and an unknown impurity (RT=5 minutes) was significantly increased (Rx200 2.5% to 5%, Rx103 0.08% to 0.8-0.9%, and RT=5 minutes 3% to 7%). The amount of cis-oleyl alcohol detected was increasing with time, which indicated that Rx100 was hydrolyzing. Multiple IPAc extractions negatively affected the purity of Rx100. The Rx100 oil produced in this batch had a low HPLC purity of 92%. Based on DOE studies on 20 g scale batches, we found three alkaline extractions in step-2 alkaline-acidic work up led to Rx100 decomposition. Thus in preparing 20 g batches, one alkaline extraction is preferred.

3.4 Mixed Solvent Crystallization.

Crystallization in a variety of solvents was screened. Aqueous methanol systems were used until JMPS experienced difficulty to produce a 100 g batch of solid and there was minimal difference in purity between Rx100 oil and Rx100.L-lysine. Varying the order of addition and water content were also unsuccessful. In further attempts, either THF or isopropyl acetate was added to the system. Isopropyl acetate content varied between 10% and 50% were successful in producing semi-crystalline material with reduced impurity content. Rx100 (oil) was dissolved in isopropyl acetate and diluted with methanol, and transferred to the reaction flask. A minimum amount of water to dissolve L-lysine is required prior to dilution with methanol. While stirring the Rx solution, the aqueous L-lysine solution was added drop-wise. A transient precipitate was observed which re-dissolves until approximately half of the lysine solution was added, then a persistent solid remained in suspension. The semi-crystalline material is easier to handle from batches produced with 20-50% isopropyl acetate. The purity profile dramatically increased in these batches as well.

3.5 Process Demonstration of (20 g) Batches.

The process variables recommended by the DOE experiment were used to produce three 20 g batches of Rx100, which were crystallized using the mixed solvent crystallization process discussed in Example 4.4. The HPLC-CAD purity of Rx100 (free acid) was approximately 95% for two batches and 88% for the third batch. HPLC-CAD purity of Rx100.L-lysine samples were >97% for all three batches. This process was scaled up to 50 g to produce the QC reference standard as detailed below in Example 5.

EXAMPLE 4

50 G Scale API Synthesis of Rx100.L-Lysine Salt

A 50 g demonstration batch was produced according to Scheme V in FIG. 41. The process included only one alkaline extraction in step-2 and use of the mixed solvent crystallization solvent system (MeOH/IPAC/H2O).

4.1 Synthesis of Dichloro Intermediate (IM, 2) from Oleyl Alcohol.

The reaction procedure is as follows: 2-Liter four-neck round bottom flask equipped with overhead stirrer, 250 mL additional funnel, 60 mL additional funnel and temperature probe was kept under argon atmosphere. The flask was charged with 200 mL of heptane and cooled to −5° C.; and overhead stirring was started. Pyridine (22.5 mL) was charged into the flask via 60 mL additional funnel, and 70 mL of heptane was used to rinse the funnel. The mixture was cooled to −5° C. Thiophosphoryl chloride (28.3 mL) was charged into the flask via 60 mL additional funnel drop by drop over 15 minutes, and 30 mL of heptane was used to rinse the funnel ($T_{initial}$ −5° C. and $T_{final}$ 5° C.). The stirring was continued at 10° C. for 30 minutes and allowed to warm to 10° C. The reaction mixture became a clear solution with fine precipitate at this point. Cis-Oleyl alcohol (OA) (50 g) dissolved in 250 mL of heptanes. The reaction mixture was first cooled to 0° C., then the cis-OA was charged into the reaction flask via 250 mL additional funnel over 25 minutes (11 to 12 mL per minute) and the reaction temperature was maintained below 10° C.; and heptane (50 mL) was then charged as a rinse. The stirring was continued for 5 h and TLC examination (Hexanes or 10% Ethylacetate in Hexanes) at this time revealed the absence of the starting material. The internal temperature of the reaction mixture was 20° C. at the end of the reaction. The reaction mixture was filtered through a sintered funnel to remove the pyridinium salt. The amount of precipitate appeared to be low, which was similar to previous 5 g process development batches prepared under the same conditions. Heptane (50 mL) was used to rinse the flask and to wash the solid. To the filtrate was added 200 mL of water followed by 200 mL of 1 N HCl and the resulting mixture was stirred by overhead stirrer for 15 minutes. The mixture was transferred into a separatory funnel to separate the organic layer from the aqueous layer. The organic layer was again washed by addition of 200 mL of water followed by 200 mL of 1 N HCl; and stirred with overhead stirrer for 15 minutes. The mixture was transferred into the separatory funnel and the organic layer was separated from the aqueous layer. The organic layer was washed with 200 mL of water to remove excess HCl and separated from aqueous layer using a separatory funnel. The organic layer was dried over $Na_2SO_4$ (10 g) and evaporated under reduced pressure to yield 78 g of acidic washed intermediate (2). The headspace of the container with intermediate (2) was purged with argon and the resulting capped container was placed at −20° C. This intermediate was used in the subsequent step without further purification.

Analytical results of the intermediates are as follows: $^1$H NMR (CDCl$_3$, 400 MHz): 5.40-5.20 (m, 2H), 4.30-4.98 (m, 2H), 2.05-1.90 (m, 4H), 1.8-1.6 (m. 2H), 1.48-1.08 (m, 11H), 0.87 (t, Z=5.8 Hz, 3H); $^{31}$P NMR (CDCl$_3$, 400 MHz): δ58.28; Impurities peaks were seen at δ 68.13, 57.95, 7.81 with 0.03% peak height with respect to product peak. $^{13}$C NMR (CDCl$_3$, 125 MHz): 130.02, 129.95, 129.70, 72.57, 72.46, 31.92, 31.90, 29.78, 29.69, 29.57, 29.54, 29.48, 29.34, 29.31, 29.2, 29.14, 29.04, 28.98, 27.23, 27.16, 25.55, 25.35, 22.70. IR (cm$^{-1}$): 2900, 2800, 1500, 1000, 700, 660. HPLC-CAD: HPLC data determines the purity of the sample as 93.42%.

4.2 Synthesis of Rx100 (Free Acid) from Dichloro Intermediate (2) Via Hydrolysis.

The reaction procedure is as follows: 2-Liter four-neck round bottom flask equipped with overhead stirrer, additional funnel, temperature probe and argon inlet was kept under argon atmosphere. The flask was charged with 75 g of dichloro intermediate (IM) dissolved in 700 mL of THF via additional funnel and 50 mL of THF was used to rinse the flask and the additional funnel. Heptane (150 mL) was charged into the reaction flask via an additional funnel and the flask was cooled to 0° C., and the stirring was started with overhead stirrer. NaOH (22.3 g, 558 mmol, 3 eq) dissolved in 700 mL of water (pre-made and allowed to cool to room temperature) was added to the reaction mixture via additional funnel over 30 minutes and 50 mL of water was used to rinse the flask ($T_{initial}$ 0° C. and $T_{final}$ 10° C.). After stirring the reaction mixture for 10 minutes, internal temperature was decreased to 6° C., then Et$_3$N (48 mL, 372.4 mmol, 2 eq) was charged to the reaction mixture via additional funnel, maintaining the temperature below 10° C. (0-10° C.). The ice bath was removed to allow the reaction temperature to warm to room temperature (<25° C.) over 30 minutes. The cloudy reaction mixture was stirred vigorously using an overhead stirrer at room temperature for 6 h. The reaction progress was monitored via TLC and at 6 h TLC revealed the absence of the starting material. It was observed that the reaction mixture became a clear solution at the end of the reaction and two layers were well separated. The reaction mixture was transferred into the 5-liter round-bottom flask, and the reaction mixture (measured at pH 10) was adjusted to pH 12 by adding 150 mL of 1N NaOH solution (drop-wise or all at once). IPAc (800 mL) was added to the reaction mixture, and the mixture was stirred by overhead stirrer for 15 minutes vigorously to extract alkaline and non-polar impurities into the organic layer. Stirring was stopped and the reaction mixture kept under argon aside for 45 minutes to get two layers separated from each other. The aqueous organic reaction mixture was transferred into the 4-liter separatory funnel and washed consecutively with 2×50 mL of water and 2×50 mL of IPAc which was first used to rinse the round bottom flask. The clear upper organic layer (IPAc wash) was separated from alkaline solution and was evaporated under reduced pressure to yield 1.68 g of non-acidic impurities. The combined alkaline aqueous layer was transferred into a round bottom flask, cooled with ice water bath and was added 500 mL of IPAc. The mixture was stirred with overhead stirrer and 300 mL of 1 N HCl was added to it to bring the pH to pH 2; and vigorous stirring was continued for 10 minutes. The mixture was transferred into a separatory funnel to separate two layers; and the two layers collected in clear glassware. The acidic aqueous layer (still pH 2) was stirred once again for 10 minutes after the addition of 400 mL of IPAc, and then transferred to a separatory funnel. The layers were collected separately from the separatory funnel. The combined IPAc solutions (containing Rx100.FA) were washed with 500 mL of water to reduce HCl content, followed by 400 mL of brine solution; and the organic layer was dried over anhydrous sodium sulfate. Evaporation of the solvent under reduced pressure yielded Rx100.FA (3) in 90% overall yield (61.5 g) for two steps.

Analytical results of the Rx100.FA are as follows: $^1$H NMR (CDCl$_3$, 400 MHz): 5.40-5.28 (m, 2H), 4.15-4.06 (m, 2H), 2.04-1.95 (m, 4H), 1.74-1.65 (m. 2H), 1.40-1.20 (m, 22H), 0.9-0.82 (m, 3H), and two impurity peaks were seen at δ 3.75 and 3.4. $^{31}$P NMR (CDCl$_3$, 400 MHz): δ 37.82; $^{13}$C NMR (CDCl$_3$, 125 MHz): 129.97, 129.60, 68.57, 68.22, 68.18, 31.93, 30.05, 29.99, 29.77, 29.55, 29.46, 29.35, 29.27, 29.19, 27.22, 25.47, 22.69, 21.76, 21.52, 14.13. ESI (m/z): 363.1 (M−H$^+$). IR (cm$^{-1}$): 2900, 2800, 1700, 1500, 1350, 1300, 1000, 700. HPLC-CAD: HPLC-CAD indicates the purity of the sample as 91.31%. Rx-200 is present in 3.53% and Rx-103 is present in 0.1%.

4.3 Crystallization of Rx-100.L-Lysine Salt from Rx-100 (free acid; 3).

The reaction procedure is as follows: water (55 g, 1.5 v) was added to L-Lysine (36.3 g) in a flask and the mixture was stirred at room temperature for 20 minutes to dissolve Lysine. Methanol (163 g) was added to the aqueous L-lysine solution and the stirring continued at room temperature for 20 minutes. 1-liter three-neck round bottom flask equipped with overhead stirrer, 120 mL additional funnel, and argon inlet was kept under argon atmosphere. Rx-100 (60 g) dissolved in 80 g of IPAc was transferred into the 1-liter RBF via additional funnel and two 20 g of IPAc were used to rinse the flask. MeOH (360 g) was charged into the flask via the additional funnel. The mixture was stirring with the overhead stirrer at room temperature under argon atmosphere. The above prepared L-lysine solution was transferred into the additional funnel and it was charged into the Rx-100 solution drop by drop over a period of 1 h under vigorous stirring with overhead stirrer at the room temperature. As the lysine solution was added a fine precipitate formed but disappeared, until about one-quarter of the lysine solution was added at which time the precipitate persisted. MeOH (50 g) was used to rinse the lysine solution flask and additional funnel. It was observed that no salt formation took place until the addition of 50 mL of L-lysine solution to Rx-100 solution, and at the end of the addition very nice free floating white solid was seen in the reaction mixture. The reaction mixture was stirred at room temperature for an additional 2 h and then filtered through a sintered funnel to isolate the solid. The filter cake was washed with 2×300 mL of MeOH and dried under vacuum for 15 minutes before it was transferred into a freeze drying flask. The solid was dried under vacuum at room temperature for 6 h to get the free flowing white solid in 80% yield (75.8 g).

Analytical results of Rx100.L-Lysine salt are as follows: MP Range: 152.9° C. to 184° C. (Single MP 160.9° C.). $^1$H NMR (D$_2$O, 400 MHz): 5.26 (m, 2H), 3.66-3.74 (m, 4H), 2.93 (t, J=8 Hz, 3H), 1.94 (m, 4H), 1.81 (m, 4H), 1.62 (m, 4H), 1.3-1.6 (m, 4H), 1.19-1.3 (m, 22H), 0.77 (t, J=8 Hz, 3H). $^{31}$P NMR (D$_2$O, 400 MHz): δ 46.60; Impurities peaks were seen at δ 45.84, 23.09 and 7.60 with 0.02% peak height with respect to product peak; $^{13}$C NMR (D$_2$O, 125 MHz): 174.85, 129.78, 129.50, 54.28, 38.86, 31.93, 29.89, 29.77, 29.63, 29.54, 29.39, 27.29, 27.17, 26.38, 25.94, 22.62, 21.41, 13.88. ESI (m/z): 657.3 (di salt, M+H$^+$), 511.2 (mono salt M+H$^+$). IR (cm$^{-1}$): 2900, 2800, 1580, 1500, 1400, 1080, 1000, 800, 700, 600. HPLC-CAD: HPLC-CAD indicates the purity of the sample as 98.81%, and Rx-200 was not detected while Rx-103 is present in 0.12%.

Therefore, we have demonstrated in the above examples the successful synthesis of Rx100.L-lysine (salt) starting with cis-oleyl alcohol and thiophosphoryl chloride. The salt isolated showed HPLC-CAD purity of 98.81% (% area) and a purity % w/w as is 95.8%. Known impurities detected are 0.58% Rx103 and 0.21% cis-oleyl alcohol; unknown impurities are 1.4% RRT 0.71, 0.29% RRT 0.79, 0.13% RRT 0.78 and 0.08% RRT 1.31. 1H-NMR of Rx100.L-Lysine does not show any impurity peaks. Three phosphorus impurity peaks were detected in 31P-NMR at δ 45.84, 23.09, 7.60 at approximately 0.02% of peak height with respect to drug peak height at δ 46.60. Residual methanol was high (3500 ppm) because the material was briefly dried under vacuum at ambient temperature. Water content determined by oven Karl Fisher (130° C.) is 1.2%.

EXAMPLE 5

CGMP Manufacturing of Rx100.L-Lysine

The Rx100.L-Lysine salt used in pilot animal and toxicology studies was manufactured and tested in accordance with cGMP. The manufacturing process for Rx100.L-Lysine was based on thiophosphorylation of cis-oleyl alcohol with thiophosphoryl chloride in presence of anhydrous base, followed by aqueous alkaline hydrolysis to form Rx100.FA, which is purified by alkaline and acid extractions. Rx100.L-Lysine salt was formed by the precipitation with L-lysine. Synthesis of Rx100.lysine utilizes only class 2 and class 3 solvents and readily available commercially available reagents, purification by precipitation, and vacuum oven drying to remove residual solvents. An inert atmosphere is maintained during manufacture to reduce the formation of oxidative degradation products. IPC refers to in-process controls. The manufacturing process (i.e., stage 1a, stage 1b and stage 2) is described as follows.

Stage 1a—Synthesis of Dichloro Intermediate.

Pyridine (0.67 kg) was charged to n-heptanes (1.4 kg) in a 100 L jacketed glass reactor, and cooled to <0° C. Thiophosphoryl chloride (1.42 kg) was added slowly to maintain a temperature below 5° C., with a nitrogen gas flow to remove HCl gas. The reaction mixture was allowed to warm to 10° C. for the reagents to activate, which was visually apparent when the liquid turns from hazy to clear with a fine white suspension (IPC 1). The mixture was cooled to 5° C., and cis-oleyl alcohol (1.5 kg) in n-heptanes (5 kg) was added slowly to maintain a temperature below 5° C. All solutions and the reaction were performed under a nitrogen atmosphere. The mixture was stirred for 30 minutes as the temperature before raised to 10° C. The reaction mixture was stirred for 4-5 h as the temperature was permitted to rise from 10° C. to 20° C. Consumption of cis-oleyl alcohol was monitored by TLC on silica plates. Reaction completion was confirmed by HPLC monitoring (<1% cis-oleyl alcohol remaining); (IPC 2 & 3). The reaction mixture was filtered through a polypropylene or polyethylene filter cloth to remove pyridinium hydrochloride salt. The filtrate was washed once with 1N HCl solution; washed with water and dried over anhydrous sodium sulfate. The n-heptane solution was evaporated under reduce pressure to afford approximately 90% of the theoretical amount of dichloro intermediate in less than 3 volumes of oil in residual n-heptane (IPC 4), which may be stored under nitrogen headspace at −20° C. for hours to days, and taken to the next step without further purification. Sample was submitted for identification testing, physical appearance, purity and impurity by HPLC-CAD analysis (IPC 5-9).

Stage 1b—Hydrolysis of Dichloro Intermediate to Form Rx100.FA.

Dichloro intermediate containing less than 3 volumes of n-heptanes was diluted with BHT stabilized THF (20 kg). Filter the liquid through a polypropylene or polyethylene filter if it contains fine precipitate due to residual water or precipitated sodium sulfate from the oil (IPC 1). Transfer to the jacketed 100 kg reactor, and cool to <10° C. All solutions and the reaction were performed under a nitrogen atmosphere. 1N sodium hydroxide solution (0.64 kg in 20 kg water, 3 eq) was slowly added to maintain the temperature below 10° C. Triethylamine (1 kg, 1 eq) was added to accelerate hydrolysis of the dichloro intermediate. Reaction progress was monitored by TLC until the reaction was complete (approximately 4-6 hr at room temperature (20-25° C.); (IPC 2). The reaction mixture was adjusted from approximately pH 10 to pH 11-12 with 1N sodium hydroxide solution and washed once with IPAc to extract non-acidic impurities into the organic layer. The aqueous layer was cooled to <10° C., and 1N hydrochloric acid solution was added slowly to maintain the temperature under 10° C. to pH 1 to 2.5. The endpoint for addition of acid was when the visual appearance (IPC 3) of the organic layer turns clear; typically between pH 1.5 and 2. The layers were separated and the aqueous layer was extracted again with IPAc. The two IPAc layers contain Rx100.FA. The IPAc layers were combined and washed with water and brine solution, and dried over anhydrous sodium sulfate. The organic layer was evaporated under reduced pressure to an oil containing Rx100.FA and up to 2 volumes of residual IPAc (IPC 4). Rx100.FA oil was sampled for IPC Tests (IPC 5-9).

Stage 2—Rx100.Lysine Formation.

All solutions and mixing was performed under a nitrogen atmosphere. The IPAc content in Rx100 oil (from Stage 1b) was adjusted to a total of 2 volumes of IPAc, if necessary, and was then diluted with methanol (5 volumes) and filtered through a 0.2 μm filter as it was transferred to the clean 100 L jacketed glass reactor. Filter was rinsed with 1 volume of methanol and added to the reactor. L-lysine was dissolved in water (1.5 volumes to lysine) at room temperature or slightly warmed to aid dissolution, and then diluted with methanol (4.5 volumes to lysine). The L-lysine solution was filtered to a clean side container. While stirring the reactor solution vigorously, the 0.2 μm filtered L-lysine solution was added drop wise to the reactor mixture. When the lysine solution addition was complete, a white slurry was formed which was stirred for 2-3 hours at room temperature. Under nitrogen gas pressure, the suspension was transferred to a 3 to 10 μm pore polypropylene or polyethylene bag filter under vacuum (with nitrogen gas headspace). The solid was collected by vacuum filtration and washed with methanol (6-12 volumes) on the filter. The filter cake was dried under vacuum for 12 h on the filter. The cake was transferred to oven trays and dried at 30° C. under vacuum. The powder was dried to constant weight and low residual solvent levels (IPC 1 & 2) in a vacuum oven, with nitrogen gas back flow.

The resultant salt was analyzed by proton NMR ($^1$H NMR) spectroscopy. The $^1$H NMR data are consistent with the structure of Rx100.L.Lysine. The spectra were obtained as solutions in $D_2O$ at 300 MHz. A table of chemical shift assignments is shown below in Table 23 and Formula II (Lot# RxB-RS-015-122; JMPS Lot No. 4252.C.12.601).

TABLE 23

Proton chemical shift data for Rx100.lysine.

| No. | δ (ppm) | Comment | Assignment |
| --- | --- | --- | --- |
| 1 | 0.84 | (t, J = 8 Hz, 3H) | —$CH_3$(Rx100 part) |
| 2 | 1.35-1.19 | (m, 22H) | —$CH_2$-(Rx100 part) |
| 3 | 1.51-1.37 | (m, 6 H) | —$CH_2$-(Rx100 part) |
| 4 | 1.72-1.64 | (m, 4H) | —$CH_2$-(lysine part) |
| 5 | 1.89-1.78 | (m, 4H) | —$CH_2$-(lysine part) |
| 6 | 2.08-1.95 | (m, 4H) | —$CH_2$-(lysine part) |
| 7 | 2.97 | (t, J = 8 Hz, 3 H) | —$CH_2$-(lysine part) |
| 8 | 3.80-3.65 | (m, 4H) | —$CH_2$-(Rx100 part); —CH-(lysine part) |
| 9 | 5.35-5.25 | (m, 2) | —$CH_2$=$CH_2$-(Rx100 part) |

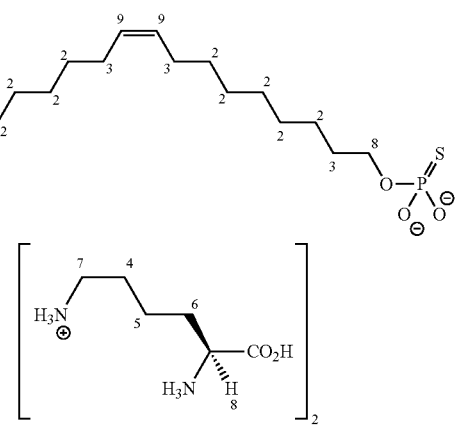

Formula II

The $^{13}$C NMR spectra of the resultant salt is also consistent with the structure of Rx100.L.Lysine. The spectra were obtained as solutions in $D_2O$ at 75 MHz. A table of chemical shift assignments is shown below in Table 24 and Formula III.

TABLE 24

$^{13}C$ Chemical Shift Assignments for Rx100.lysine in $D_2O$ at 25° C.

| Carbon No. | δ(ppm) |
|---|---|
| 1 | 13.78 |
| 2 | 129.48 |
| 3 | 129.75 |
| 4 | 54.28 |
| 5 | 174.83 |
| 6 | 38.84 |

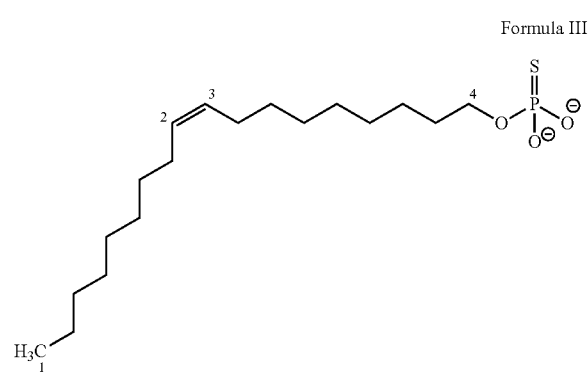

Formula III

The $^{31}P$ NMR spectra of the resultant salt are consistent with the structure of Rx100.L.Lysine. The spectra were obtained as solutions in $D_2O$ at 162 MHz. Peak at δ 46.6 in $^{31}P$ NMR spectrum confirms the thiophosphate group is present.

EXAMPLE 6

Pharmacokinetic Studies of Rx100.L-Lysine Salts 6.1 Pharmacokinetics of Rx100.Ammonia and Rx100.Lysine in Irradiated and Unirradiated Mice We performed a randomized, open-label, single-dose, four-arm, subcutaneously-administered, study of the pharmacokinetics of Rx100.Ammonia and Rx100.Lysine in irradiated and unirradiated C57BL/6 mice to evaluate the effect of salt form and irradiation on extravascular pharmacokinetics. The purpose of this study was to evaluate the pharmacokinetic parameters for two salt forms of Rx100 (Lysine and Ammonia) in healthy and PB irradiated (IR) mice when administered as a single dose. Each animal received a 1 mg/kg dose of Rx100.Lysine or Rx100.Ammonia. The animals receiving Rx100.Lysine or Rx100.Ammonia after irradiation were dosed 26±2 hours after irradiation and sampling times are relative to the time of test article dosing.

More specifically, randomized, acclimated, C57BL/6 mice were administered Rx100.Lysine or Rx100.Ammonia (10 mM L-histidine in sterile water for injection, or 1% ethanol, 2% propylene glycol in PBS, respectively) as a single dose as indicated in Table 25.

TABLE 25

Outline of study design.

| Group | Test Article | Test Article Dose (mg/kg) | Vehicle | Irradiation Dose (Gy)[1] | Timing of Dose relative to Irradiation | Animal Number[2] |
|---|---|---|---|---|---|---|
| 1 | Rx100.Lysine | 1 | WFI[3] | 15.6 | 26 ± 2 | 80 |
| 2 | Rx100.Ammonia | 1 | EPGPBS[4] | 15.6 | 26 ± 2 | 80 |
| 3 | Rx100.Lysine | 1 | WFI[3] | 0 | N/A | 80 |
| 4 | Rx100.Ammonia | 1 | EPGPBS[4] | 0 | N/A | 80 |

[1]The dose rate at the time of irradiation was 147.13 cGy/min, and the exposure time was 10.6 minutes.;
[2]Male to Female ratio was 1:1;
[3]water for injection;
[4]1% ethanol, 2% propylene glycol in PBS.

Blood was collected from 4 male and 4 female mice via cardiac puncture at pre-defined time points relative to test article dosing (0.5, 1, 2, 4, 6, 8, 12, 18, 24, and 48 hours) and collected into micro plasma separator vials (BD Microtainer®) containing lithium heparin. Blood was maintained on ice until centrifugation and subsequent processing. Blood draws were a terminal procedure. Plasma was frozen at −80° C. until submitted for bioanalysis. Sample collection was completed in September 2012. Samples were transferred to Covance in December 2013, and sample analysis was complete in the first quarter of 2014.

A total of 160 male and 160 female C57BL/6 10-12 week old mice were used in this study. Animals were randomized with weight stratification into treatment groups and given a second ear tag. Animals were acclimated for 16-19 days (See below Table 26). Prior to irradiation or dosing (in non-irradiated groups), animals were weighed a second time which was the basis of the animal dose delivered.

TABLE 26

Summary of acclimation start and end dates, and total number of days acclimated.

| Group | Acclimation stat date | Acclimation stat date | # Days acclimated |
|---|---|---|---|
| 1 | Aug. 12, 2012 | Aug. 26, 2012 | 16 Days |
| 2 | Aug. 12, 2012 | Aug. 28, 2012 | 18 Days |
| 3 | Aug. 22, 2012 | Sep. 10, 2012 | 19 Days |
| 4 | Aug. 31, 2012 | Sep. 18, 2012 | 18 Days |

Following completion of acclimation, the appropriate groups (1 and 2) of animals were irradiated (Aug. 27, 2012-Aug. 29, 2012) for 10.6 minutes resulting in a calculated dose of 15.6 Gy because the dose rate at the time of irradiation was 147.13 cGy/minute. TLDs were used for dosimetry and confirmation of the delivered dose. TLDs were analyzed by MD Anderson and have a +/−5% accuracy. A total of 19 dosimeters were used with a mean measured dose of 15.33±0.166 Gy.

Analysis was performed using qualified and validated Phoenix® WinNonlin® Software. The final data provided was imported into Phoenix® WinNonlin®. All data presented in the tables and figures within the results section of this report were generated using the validated Phoenix® WinNonlin® Software.

Rx100.Lysine was rapidly absorbed after subcutaneous (SC) administration to healthy subjects with a $T_{max}$ of 1.0 hour and a corresponding $C_{max}$ of 455 ng/mL in females and 570 ng/mL in males. The exposure (AUC) in females is 1593 h*ng/mL and 1751.1 ng/mL in males. The concentration vs. time profile, clearance (CL), volume of distribution (Vd), and Exposure (AUCINF_obs) of Rx100.Lysine in healthy subjects can be found below in FIG. 25 and Table 27.

TABLE 27

Pharmacokinetic parameters of a single dose (1 mg/kg) of Rx100.Lysine in healthy mice.

| Gender | Cmax (ng/mL) | Tmax (h) | HL_Lambda_z (h) | AUCINF_obs (h * ng/mL) | CLss_F (mL/h/kg) | Vz_F (mL/kg) |
|---|---|---|---|---|---|---|
| F | 454.50 | 1.00 | 1.84 | 1593.20 | 627.71 | 1664.32 |
| M | 570.00 | 1.00 | 1.91 | 1751.12 | 571.10 | 1570.87 |

The $C_{max}$ (355 ng/mL in IR females and 299 ng/mL in IR males compared with 455 ng/mL in healthy females and 570 ng/mL in healthy males), $T_{max}$ (0.5 h compared with 1 h), and AUC (1238 h*ng/mL in IR females and 1169 h*ng/mL in IR males compared with 1593 h*ng/mL in healthy females and 1751 h*ng/mL in healthy males) for Rx100.Lysine appears lower and earlier after irradiation. However, the concentration vs. time profiles overlap (within error) as illustrated in FIG. 27. The pharmacokinetic parameters and concentration vs. time profile for Rx100.Lysine in irradiated mice are found in Table 28 and FIG. 26.

TABLE 28

Pharmacokinetic parameters of a single dose (1 mg/kg) of Rx100.Lysine in irradiated mice.

| Gender | Cmax (ng/mL) | Tmax (h) | HL_Lambda_z (h) | AUCINF_obs (h * ng/mL) | CLss_F (mL/h/kg) | Vz_F (mL/kg) |
|---|---|---|---|---|---|---|
| F | 354.67 | 0.50 | 1.87 | 1237.84 | 807.93 | 2173.84 |
| M | 298.75 | 0.50 | 1.32 | 1168.48 | 855.81 | 1625.47 |

Rx100.Ammonia was rapidly absorbed after subcutaneous (SC) administration to healthy subjects with a $T_{max}$ of 0.5-1.0 hour and a corresponding $C_{max}$ of 302 ng/mL in females and 476 ng/mL in males. The exposure (AUC) in females is 1152 h*ng/mL and 1521 ng/mL in males. The concentration vs. time profile, clearance (CL), volume of distribution (Vd), and Exposure (AUCINF_obs) of Rx100.Ammonia in healthy subjects are found below in FIG. 28 and Table 29.

TABLE 29

Pharmacokinetic parameters of a single dose (1 mg/kg) of Rx100.Ammonia in healthy mice.

| Gender | Cmax (ng/mL) | Tmax (h) | HL_Lambda_z (h) | AUCINF_obs (h * ng/mL) | CLss_F (mL/h/kg) | Vz_F (mL/kg) |
|---|---|---|---|---|---|---|
| F | 301.75 | 1.00 | 1.38 | 1152.19 | 867.93 | 1728.37 |
| M | 475.50 | 0.50 | 1.41 | 1521.44 | 657.27 | 1340.70 |

The $C_{max}$ (407 ng/mL in IR females and 622 ng/mL in IR males compared with 302 ng/mL in healthy females and 476 ng/mL in healthy males), CL (629 mL/h/kg in IR females and 581 mL/h/kg in IR males compared with 868 mL/h/kg in healthy females and 657 in healthy males), and), and AUC (1591 h*ng/mL in IR females and 1721 h*ng/mL in IR males compared with 1152 h*ng/mL in healthy females and 1521 h*ng/mL in healthy males) appear lower after irradiation. However, the concentration vs. time profiles overlap (within error) as illustrated in FIG. 30. There was no change in the Tmax (0.5-1.0 hr) or half-life after irradiation. The pharmacokinetic parameters and concentration vs. time profile for Rx100.Ammonia in irradiated mice are found in Table 30 and FIG. 29.

8, 24, 48, 72, 96, and 120 hours after dosing for phases 1 and 2. The phase 3 (post-irradiation phase) blood was collected at baseline (7-10 days prior to dose administration), pre-dose (within 30 minutes), 0.5, 1, 2, 4, 6, 8, 24, 48, 72, and 96 hours after dosing. The dose in phase 3 was administered approximately 24 hours after exposure to 11.5 Gy Partial Body Irradiation. Samples, approximately 1.0 mL, were collected and maintained on wet ice in vials containing Di-Potassium EDTA until centrifugation. Samples were stored in a freezer set to maintain −70° C. to −90° C. until shipped on dry ice for analysis.

TABLE 30

Pharmacokinetic parameters of a single dose (1 mg/kg) of Rx100.Ammonia in irradiated mice.

| Gender | Cmax (ng/mL) | Tmax (h) | HL_Lambda_z (h) | AUCINF_obs (h * ng/mL) | CLss_F (mL/h/kg) | Vz_F (mL/kg) |
| --- | --- | --- | --- | --- | --- | --- |
| F | 406.66 | 1.00 | 1.36 | 1591.05 | 628.50 | 1229.69 |
| M | 622.25 | 0.50 | 1.52 | 1720.87 | 581.10 | 1276.97 |

As such, there were no substantial differences in either the concentration vs. time profiles (FIG. 31) or the pharmacokinetic parameters of Rx100.Ammonia vs. Rx100.Lysine in healthy or irradiated mice (Table 31).

TABLE 31

Comparison of the pharmacokinetics of Rx100.Lysine to Rx100.Ammonia in healthy and irradiated mice.

| Group | Cmax (ng/mL) | Tmax (h) | HL_Lambda_z (h) | AUCINF_obs (h * ng/mL) | CLss_F (mL/h/kg) | Vz_F (mL/kg) |
| --- | --- | --- | --- | --- | --- | --- |
| Rx100 Ammonia | 383.75 | 0.50 | 1.78 | 1342.00 | 745.16 | 1918.18 |
| Rx100 Ammonia + IR | 466.71 | 0.50 | 1.37 | 1644.99 | 607.91 | 1200.34 |
| Rx100.Lysine | 512.25 | 1.00 | 1.16 | 1661.33 | 601.93 | 1006.22 |
| Rx100.Lysine + IR | 322.71 | 0.50 | 1.44 | 1205.77 | 829.35 | 1722.42 |

6.2 Comparison of Subcutaneous and Intravenous Pharmacokinetics of Rx100.L-Lysine in Healthy Rhesus Macaques and Subcutaneous Pharmacokinetic and Pharmacodynamics of Rx100.L-Lysine after a Single Irradiation in Rhesus Macaques.

We performed a cross-over comparison of subcutaneous and intravenous pharmacokinetics of Rx100.L-Lysine in six healthy Rhesus Macaques and subcutaneous pharmacokinetic and Pharmacodynamics of Rx100.L-Lysine after a single irradiation in six Rhesus Macaques.

Rhesus macaques (male, 3-5 kg) were administered vehicle control article (10 mM Histidine in sterile water for Injection, USP) or Rx100.Lysine salt as a single injection via subcutaneous injection or as an intravenous bolus as indicated in Table 32.

Blood was collected at baseline (7-10 days prior to dose administration), pre-dose (within 30 minutes), 0.5, 1, 2, 4, 6,

TABLE 32

Dosing group schedule for Pharmacokinetic evaluation

| Phase | Route of Administration | Dose Level (mg/kg) | Irradiation (Gy) | No. of Animals |
| --- | --- | --- | --- | --- |
| 1 | IV | 1 | 0 | 3 |
|   | SC | 1 | 0 | 3 |
| 2 | IV | 1 | 0 | 3 |
|   | SV | 1 | 0 | 3 |
| 3 | SC | 1 | 11.5* | 6 |

*11.5 Gy represents the target irradiation dose. Actual irradiation doses delivered to each subject varied.

Analysis was performed using qualified and validated Phoenix® WinNonlin® Software and RxBio™ SOP PRE-0030™, Phoenix® WinNonlin® Software for Statistical Analysis. The final data provided was imported into Phoenix® WinNonlin®. All data presented were generated using the validated Phoenix® WinNonlin® Software. Concentrations reported as BLOQ were treated as missing values for the purpose of this analysis. A non-compartmental pharmacokinetic analysis was performed for each subject separately for IV, SC, and SC+IR. The automatic terminal slope selector function was used along with nominal dose (1 mg/kg) with a dosing interval set at 120 hours since this was a single dose study. The terminal slope was selected from the last 3 quantifiable plasma concentrations for each subject (48-96 hours for the Phase 3 Irradiated subjects and 72-120 for all healthy subjects). Selected pharmacokinetic estimations are presented in Table 33, time of maximum concentration ($T_{max}$ (h)), maximum concentration observed ($C_{max}$ (ng/mL)), exposure or area under the concentration vs time curve (AUC (h*ng/mL)), volume of distribution (Vz_F (mg/kg)), clearance (CL_F (mL/h/kg), and half-life (T½ or HL_Lambda_z (h)).

TABLE 33

Key pharmacokinetic parameters of each animal and the mean for each route of administration +/− irradiation.

| Route | Animal ID | Cmax (ng/mL) | Tmax (h) | $\lambda z$ (1/h) | $T_{1/2}$ (h) | $AUC_{OBS}$ (h * ng/ mL) | $AUC_{INF}$ (hr * ng/ mL) | CL (mL/hr/kg) | Vd (mL/kg) |
|---|---|---|---|---|---|---|---|---|---|
| SC | RQ8976 | 3180 | 4 | 0.066 | 10.6 | 70702 | 70742 | 14 | 215 |
|  | 1006231 | 3420 | 2 | 0.065 | 10.7 | 66561 | 66593 | 15 | 231 |
|  | 1004197 | 3490 | 2 | 0.069 | 10.0 | 50387 | 50402 | 20 | 287 |
|  | 1004039 | 2390 | 2 | 0.066 | 10.6 | 40623 | 40641 | 25 | 376 |
|  | 1004037 | 3940 | 6 | 0.072 | 9.67 | 101174 | 101196 | 10 | 138 |
|  | 1003049 | 2350 | 6 | 0.061 | 11.4 | 52620 | 52659 | 19 | 313 |
|  | Average | 3128 ± 637 | 4 ± 2 | 0.066 ± 0.004 | 10.5 ± 0.600 | 63678 ± 21420 | 63706 ± 21422 | 17 ± 5 | 260 ± 83 |
| IV | RQ8976 | 15900 | 0.5 | 0.052 | 13.4 | 73501 | 73515 | 14 | 262 |
|  | 1006231 | 18800 | 0.5 | 0.071 | 9.74 | 77120 | 77133 | 13 | 182 |
|  | 1004197 | 18700 | 0.5 | 0.038 | 18.3 | 55594 | 55609 | 18 | 474 |
|  | 1004039 | 20000 | 0.5 | 0.037 | 18.8 | 49030 | 49043 | 20 | 552 |
|  | 1004037 | 20900 | 0.5 | 0.074 | 9.37 | 78965 | 78978 | 13 | 171 |
|  | 1003049 | 17600 | 0.5 | 0.024 | 28.8 | 44874 | 44892 | 22 | 926 |
|  | Average | 18650 ± 1765 | 0.5 ± 0 | 0.049 ± 0.020 | 16.4 ± 7.29 | 63181 ± 15119 | 63195 ± 15117 | 17 ± 4 | 428 ± 290 |
| SC (p 11.5 Gy) | RQ8976 | 2980 | 6 | 0.075 | 9.21 | 61742 | 61784 | 16 | 218 |
|  | 1006231 | 3600 | 4 | 0.088 | 7.88 | 54344 | 54372 | 18 | 209 |
|  | 1004197 | 3410 | 2 | 0.072 | 9.66 | 55035 | 55077 | 18 | 245 |
|  | 1004039 | 2320 | 2 | 0.079 | 8.81 | 34319 | 34336 | 29 | 355 |
|  | 1004037 | 4380 | 6 | 0.082 | 8.45 | 101292 | 101338 | 10 | 120 |
|  | 1003049 | 1950 | 2 | 0.081 | 8.56 | 36808 | 36851 | 27 | 335 |
|  | Average | 3107 ± 887 | 4 ± 2 | 0.079 ± 0.006 | 8.76 ± 0.621 | 57257 ± 24153 | 57293 ± 24160 | 20 ± 7 | 251 ± 91 |

When Single dose PK of Rx100.L-Lysine is administered in healthy subjects through either extravascular (SC) or intravenous route, Rx100 is rapidly absorbed after extravascular administration (SC) with a $T_{max}$ of 4±2 hours and a corresponding $C_{max}$ of 3128±637 ng/mL, and is expectedly higher ($C_{max}$) and earlier ($T_{max}$) after intravenous bolus administration ($C_{max}$ 18650±1765 ng/mL, 0.5±0 hr). The clearance (CL) and volume of distribution (Vd) of Rx100 are not affected by the route of administration (CL 17±5, 17±4 mL/hr/kg for SC, IV; Vd 260±83, 428±290, mL/kg for SC, IV). The exposure ($AUC_{INF}$) of Rx100 is not reduced by subcutaneous administration ($AUC_{INF}$ 63706±21422, 63195±15117 hr*ng/mL for SC, IV) indicating complete bioavailability. The fraction absorbed after subcutaneous administration (F) is 1.0±0.18. The half-life of Rx100 is not different between subcutaneous and intravenous administration in healthy subjects (SC 10.5±0.600 h, IV 16.4±7.29 h). Of note, there is a high degree of variability between subjects after intravenous administration (ranging from 9.37 hours in subject 1004037 to 28.8 hours in subject 1003049 and a group standard deviation of 7.29 hours). In contrast, the SC group has $T_{1/2}$ that range from 9.67 to 10.7 hours (subjects 1004037 and 1003049) with a corresponding standard deviation of 0.600 hours.

When Single Dose of Rx100.L-Lysine is extravascularly administered in irradiated animals, the $C_{max}$ and $T_{max}$ are unchanged when administration is delayed until after (~24 hours) irradiation ($C_{max}$ 3128±637, 3107±887 ng/mL for SC and SC post IR; $T_{max}$ 4±2 hr for both groups). The clearance and volume of distribution are not affected by irradiation under the tested conditions (CL 17±5, 20±7 mL/hr/kg; Vd 260±83, 251±91 mL/kg for SC and SC post IR). The exposures ($AUC_{INF}$s) are not different after irradiation (63706±21422, 57293±24160 hr*ng/mL for SC and SC post IR), and consequently the F does not significantly change (0.89±0.2). The half-life is shorter (10.5±0.600, 8.76±0.621 hr for SC and SC post IR) after irradiation, however the ranges of individual subjects nearly overlap (9.67 to 11.4 hours in healthy animals compared with 7.88 to 9.66 hours in irradiated animals). Of note, the last sampling point for the irradiated animals was 96 hours after dosing compared with 120 hours for healthy subjects which could impact the estimated half-life. The impact of shortening the sampling time cannot be completely assessed, however, if the 120 hour time point were not included in the half-life estimation for the healthy SC group, the estimated half-life would be shorter. Additionally, the primary parameters of Vd and CL drive the half-life estimation. Since there is no difference between these parameters (Vd and CL) after irradiation, a significant difference between the half-lives of the groups is unlikely.

EXAMPLE 7

Efficacy Studies of Rx100.L-Lysine Salt in Animal Models

Using a partial body irradiation (tibial sparing) animal model in the female C57BL/6 mice, we tested the survival advantages conferred by GMP Rx100.L-Lysine salt. As a result, when administered at 0.3 to 3 mg/kg/12 h×6 doses starting at +24 hours after exposure to 15.5 to 15.7 Gy from a [137]Cesium irradiator which otherwise reliably produces an $LD_{70-90/10}$ (in 10 days, 70-90% mice die after irradiation), the mortality was reduced by 20% to 50%. When administered at 0.1 mg/kg/day×6 doses in a partial body irradiation Animal Model in 19 male Rhesus macaque, a 37% increase in survival at a normally $LD_{70/34}$ dose of X-ray radiation was observed. By allometric scaling using body surface area, these lowest effective doses translate to 0.02 mg/kg/day and to 0.03 mg/kg/day in humans, respectively.

These Animal Model studies were all conducted using partial body irradiation (PBI) with tibial bone marrow sparing except the earliest study which was performed with Total Abdominal Irradiation (TAI). The male Rhesus macaque model was developed by MacVittie. The female inbred murine PBI GI-ARS Animal Model was developed by the inventors. Pilot studies suggested that a corresponding male murine model may not be amenable to drug testing as the radiation dose survival curve is variable, the source of variability must be related to gender (as the female mice do not have a similar issue in our facility under the same GLP condition), and an $LD_{50-90/10-30}$ cannot be predicted in advance of study conduct. Differences in radiation sensitivity by gender in rodent species are well appreciated. We are not aware of PBI GI-ARS models other than these that meet criteria required to conduct a prospective, blinded, controlled, randomized study of efficacy.

A synopsis from each of the completed three sequential efficacy studies in the C57BL/6 murine partial body irradiation model of GI-ARS is provided below. The first and second studies (WBS 4.1.4 and WBS 4.1.5) were: (1) Rx100 dose ranging efficacy study that was conducted in both male and female C57BL/6 mice after partial body irradiation; (2) evaluation of increasingly delayed initiation of the regimen (24, 48 and 72 hours after irradiation in both male and female C57BL6 mice). Upon better understanding of the relative radioresistance of the male C57BL/6 mouse, males were dropped from the pilot repeat efficacy study (Study WBS 4.1.8) while evaluation of the male model was undertaken on a separate path We have now concluded that, even with randomization, the male mortality in the control arm is unpredictable and thus, assessment of the active versus vehicle is impaired. Study WBS 4.1.8 was a pilot study of the efficacy of Rx100 at the preferred dose and regimen. The latter two studies (4.1.5) and 4.1.8) were blinded, randomized and controlled. The former study was not blinded but was controlled and randomized (WBS 4.1.4). Table 34 summarizes the observations in these studies.

TABLE 34

Summary of Survival and Survival Advantage in studies of Rx100 versus vehicle in the female murine and male rhesus Animal Models of GI-ARS (partial body irradiation)

| Species (♀/♂) | Date | Rx100 (mg/kg) | Radiation Dose (Gy) | Rx100 Start | GLP[1] | Survival Advantage Day 10 | Day ≥ 30 |
|---|---|---|---|---|---|---|---|
| NIAID HHAN272201300021C |||||||| 
| Rhesus (♂) | 2014 | 0.1 (q12x6) | $LD_{60}$ | +24 | Yes | Planned | Planned |
| RxBio ™ 418F[2] ||||||||
| Murine (♀) | 2013 | 3 (q12x6) | 15.55-67 | +24 | Yes | 32% (52/105 v 19/107)* | 25% (42/105 v 16/107)* |
|  |  |  | 15.55 | +24 | Yes | 25% (16/34 v 8/36)* | 22% (13/34 v 6/36)* |
|  |  |  | 15.62 | +24 | Yes | 47% (21/36 v 4/36)* | 39% (17/36 v 3/36)* |
|  |  |  | 15.67 | +24 | Yes | 23% (15/35 v 7/35)* | 14% (12/35 v 7/35) |
| Rx Bio 415[3] ||||||||
| Murine (♀) | 2013 | 3 (q12x6) | 15.62-64 | +24 | Yes | 50% (18/32 v 2/32)* | 28% (9/32 v 0/32)* |
| RxBio ™ 414[4] ||||||||
| Murine (♀) | 2013 | 3 (q12x6) | 15.65-8 | +24 | Yes | 23% (41/64 v 25/61)* | 26% (23/64 v 6/61)* |
| Murine (♀) | 2013 | 0.3 (q12x6) | 15.65-8 | +24 | Yes | 5% (29/60 v 25/61) | 23% (20/60 v 6/61)* |
| UC Davis ||||||||
| Rhesus (♂) | 2011 | 0.1 (q24x6) | 11.5 | +4 | No | 8% (2/9 v 3/10) | 37% (6/9 v 3/10) |
| UTHSC ||||||||
| Murine (♀) | 2010 | 0.1 | 15.0 (TAI)[5] | +24 | No | 42% (10/14 v 4/14)* |  |

*p < 0.05 by Chi Square test (two-tailed).
[1]These studies were conducted at University facilities. GLP exceptions are identified in the study reports by the RxBio ™ Quality Assurance Unit and, in the opinion of the Study Director, did not affect the quality or integrity of the data.
[2]418F was designed to confirm efficacy of Rx100 at 3 mg/kg/12hx6 in a GLP study conducted at three radiation doses that were each targeted at around or at the $LD_{50-70}$ based on prior model development work. Given poolability of lethality by Breslow-Day, the data are presented by arm and also pooled.
[3]415 was designed to confirm efficacy of Rx100 at 3 mg/kg/12hx6 in a GLP study and evaluate whether a greater delay in initiation of the regimen would provide efficacy. Rx100 dosing regimens at ≥48 h did not provide a Day 30 survival advantage and are not presented. The study was conducted in two phases based on facility limitations and to permit randomization to the three dosing regimens in each phase - each with a vehicle control. Given poolability by Breslow-Day and intent to pool, phases 1 and 2 are presented as pooled data.
[4]414 was designed as a dose range finding study. Data from Phase 1 (dose ranging from 0.3-10 mg/kg) are not presented. Data from phases 2 and 3 were pooled after Breslow-Day assessment and based on intent to pool.
[5]TAI is a total abdominal irradiation model of GI-ARS where bone marrow is maximally preserved (≈40%).

WBS 4.1.4 (Study 4.1.4) Synopsis:

The study is a randomized, open-label, dose-range-finding, vehicle-controlled, two-phase (0.3, 1.0, 3.0 and 10 mg/kg and then 0.3 and 3.0 mg/kg) pilot efficacy study of a multi-dose, subcutaneous, regimen (q12 hx6 doses) of Rx100.lysine or vehicle starting at 24 hours after partial body irradiation (PBI) with tibial sparing in male and female C57BL/6 murine Animal Model (Nonclinical Study Number: RxBio™ 2013-01-01; WBS: 4.1.4). Study was initiated on Feb. 11, 2013. Experiments were started on Feb. 11, 2013 and completed on May 2, 2013.

The primary objective of the study was to determine the most effective dose of Rx100 in RxBio™'s male and female murine Animal Model of GI-ARS with an effective dose defined as the dose giving the highest survival advantage in percent increase in survival as compared to vehicle. This study was a randomized, open-label, vehicle-controlled, two-phase (0.3, 1.0, 3.0, and 10 mg/kg and then 0.3 and 3.0 mg/kg) pilot efficacy study of a multi-dose, subcutaneous regimen (q12 hx6 doses) of Rx100.lysine or vehicle starting at 24 hours after partial body irradiation (PBI) with tibial sparing in a C57BL/6 murine Animal Model. Phase 1 (n=32 per group per sex) was designed as an expanded pilot dose-ranging study (0.3, 1.0, 3.0, and 10 mg/kg) to select two Rx100 doses for additional testing in phases 2 and 3. Phases 2 and 3 (enrolled n=64 per group per gender) were conducted at the selected Rx100 doses (0.3 and 3.0 mg/kg) to ensure sufficient sample size to power an assessment of survival advantage. The latter study was conducted in two phases based on facility limitations (up to 120 animals can be handled readily in one radiation sequence). Because the irradiation exposure times were not adjusted for the natural decay in the cesium source, the irradiation dose delivered in phase 1 was initially overestimated. As a result, the survival outcomes in the vehicle arms of Phase 1 were higher than expected and specific doses in the range could not be assessed for relative efficacy. A higher radiation dose was used in Phases 2 and 3 and two intermediate doses selected empirically (0.3 and 3.0 mg/kg). The study was carried out to 30 days post irradiation in all phases. The primary endpoint in this study was survival at Day 10. The modified intent-to-treat primary study population was defined as those animals that survived anesthesia following irradiation. Survival advantage was calculated as the percent survival in the active arm minus the percent survival in the vehicle arm for males and females separately with pairwise comparison by Chi-Square as a test of significance without adjustment for multiple testing. Significance was declared at the 0.05 level (two-sided). Based on Breslow-Day probability statistics (>0.05), data from phases 2 and 3 were pooled as intended. As shown in Table 35, there was a statistically significant survival advantage of 23.1% at Day 10 in female animals with 3 mg/kg/12 h×6 Rx100. The increase in survival at Day 10 of 7.3% for 0.3 mg/kg/12 h/6 was not statistically significant at the 0.3 mg/kg level. However, by Day 30, there was additional mortality in the vehicle but not in the active arms so that a benefit was seen at both 0.3 mg/kg and 3 mg/kg in the female animals. See Kaplan-Meier FIG. 32. There was no survival benefit in the male animals. The reasons for this disparity are unknown but could relate to the high variability in mortality at a given radiation dose in males which may not have been evenly distributed between vehicle and active arms or inappropriate dose selection.

This study confirmed the efficacy of Rx100 when administered every 12 hours starting 24 hours for a total of six doses of 3 mg/kg (q12 h×6) after potentially lethal partial body irradiation (tibial bone marrow sparing) in RxBio™'s female murine C57BL/6 Animal Model of GI-ARS which produced a survival advantage of 50% at Day 10 (and which was maintained at 28% through Day 30). Efficacy was not seen in this model in this study when dosing was started ≥48 hours after radiation injury initiated. Please see FIG. 33. Vehicle arm lethality in the male continued to show evidence of relative radioresistance but also variability. Male Day 10 lethality in the control arms was 28.1%, 43.8% and 55.2% in the 24, 48 and 72 hour groups, respectively. In contrast, at the same radiation dose, female lethality in the control arms was 93.8%, 93.8% and 71.9%, respectively. These data supported the evolving hypothesis that evaluation of Rx100 efficacy in a male murine model requires preliminary refinement of the male Animal Model to identify the source of variability and to ensure distribution or elimination of that variability between animals assigned to active and control arms. A similar concern was not evident in the female murine C576BL/6 animal model. In any event, at the Rx100 dose provided, neither efficacy nor toxicity was seen in male mice notwithstanding the attempt to distribute the variability evenly through randomization.

In sum, there was a statistically significant survival advantage in the female animals when Rx100 was given 24 hours post irradiation where the delivered radiation doses were at the preferred inflection point of the model's radiation dose response curve. Similar efficacy was not seen with further delayed initiation of therapy (≥48 hours). The parallel male study was not able to demonstrate efficacy or toxicity of Rx100 presumably based on the need for further refinement of the male murine C57BL/6 PBI Animal Model of GI-ARS and/or research into proper dose selection. We can thus conclude that the female PBI GI-ARS C57BL/6 murine Animal Model is robust and reliable in the female mice and that Rx100 provides a statistically significant 50% survival advantage when given ≤24 hours post irradiation.

TABLE 35

Study 4.1.4 dose ranging assessment of Rx100 efficacy (Day 10 Survival) in male and female C57BL/6 mice.

| Phase | Day | Vehicle | 0.3 mg/kg | 3 mg/kg | Survival advantage 0.3 mg/kg | Survival advantage 3 mg/kg |
|---|---|---|---|---|---|---|
| Females | | | | | | |
| 2 + 3 | 10 | 41.0% (25/61) | 48.3% (29/60) | 64.1% (41/64) | 7.3% | 23.1%* |
| 2 + 3 | 30 | 9.8% (6/61) | 33.3% (20/60) | 35.9% (23/41) | 23.5%* | 26.1%* |
| Males | | | | | | |
| 2 + 3 | 10 | 40.4% (23/57) | 38.2% (21/55) | 41.4% (24/58) | −2.2% | 1.0% |
| 2 + 3 | 30 | 29.8% (17/57) | 12.7% (7/55) | 17.2% (10/58) | −17.1% | 12.6% |

*p < 0.05 (Chi-square)

WBS 4.1.5 (Study 4.1.5) Synopsis.

This study is a randomized, blinded, six-arm, vehicle-controlled, pilot efficacy study of three multi-dose regimens (q12 h×6 doses) of 3 mg/kg Rx100.lysine or vehicle starting at, respectively, three different time points (e.g., 24, 48 and 72 hours) after partial body irradiation (PBI) with tibial sparing in a C57BL/6 murine Animal Model of gastrointestinal (GI) acute radiation syndrome (ARS) (Nonclinical Study Number: RxBio™ 2013-03-01/WBS 4.1.5). The study was initiated on Apr. 8, 2013. Experiments were started on Apr. 28, 2013 and completed on Jun. 26, 2013.

WBS 4.1.8 (Study 4.1.8) Synopsis.

This study is a randomized, blinded, confirmatory, seven-arm, pilot efficacy study of a multi-dose regimen (q12 h×6 doses) of 3.0 mg/kg of Rx100.lysine or vehicle each starting at 24 hours after either 15.52, 15.57 or 15.62 Gy (estimated LD50+/10) of partial body irradiation (PBI) with tibial sparing in the female in a C57BL/6 murine Animal Model of gastrointestinal (GI) acute radiation syndrome (ARS) (Nonclinical Study Number: RxBio™ 2013-07-01/WBS 4.1.8).

This study was designed to confirm the efficacy of 3 mg/kg of Rx100 when administered every 12 hours starting 24 hours for a total of six doses after potentially lethal partial body irradiation (tibial bone marrow sparing) in RxBio™'s female murine C57BL/6 Animal Model of GI-ARS. Under the study design, four radiation doses were selected for vehicle administration. The lowest dose was selected as a potential LD10/10 at 15.50 Gy and then low, mid and high radiation doses of 15.52, 15.57 and 15.62 Gy were selected to evaluate drug effect against vehicle at these higher radiation doses. There were three active test agent arms with radiation doses of 15.52, 15.57 and 15.62. The study was performed in female mice only. Thirty-six (36) mice were enrolled per arm divided into 18 per group for each phase for a total of 144 animals. Animals were randomized but stratified by weight to assure equivalent weights in each arm. The study was conducted in two phases to assure adequate subject numbers based on limitations on the number of animals that can be processed per phase (120). The primary endpoint in this study was survival at Day 10 but the study was carried out to Day 30. The modified intent-to-treat primary study population was defined as those animals that survived anesthesia following irradiation. Survival advantage was calculated as the percent survival in the active arm minus the percent survival in the vehicle arm for males and females separately with pairwise comparison by Chi-Square as a test of significance without adjustment for multiple testing. Significance was declared at the 0.05 level (two-sided). Kaplan-Meier mean survival time was also calculated and compared by the log rank test. Data from phase 1 and 2 were pooled. Survival advantage was identified as the survival in the treated group minus the survival in the vehicle control group. Based on similarity in survival among vehicle groups, a probit curve and dose modification factor was not calculated. Please see Table 36 below and FIGS. 34A, 34 B and 34C.

TABLE 36

Survival advantage at Day 10 (primary) and Day 30 of Rx100 with a dosing regimen of 3 mg/kg/12hx6 administered to female C57BL/6 mice with partial body irradiation (tibial sparing) at 15.55, 15.62, and 15.67 Gy.

| Phase | Day | Vehicle | Rx100 at 3 mg/kg/12x6 | Survival advantage |
|---|---|---|---|---|
| | | 15.55 Gy | | |
| 1 + 2 | 10 | 22.2% (8/36) | 47.1% (16/34) | 24.9%* |
| 1 + 2 | 30 | 16.7% (6/36) | 38.2% (13/34) | 21.5%* |
| | | 15.62 Gy | | |
| 1 + 2 | 10 | 11.1% (4/36) | 58.3 (21/36) | 47.2%* |
| 1 + 2 | 30 | 8.3% (3/36) | 47.2% (17/36) | 38.9%* |
| | | 15.67 Gy | | |
| 1 + 2 | 10 | 20% (7/35) | 42.9% (15/35) | 22.9%* |
| 1 + 2 | 30 | 20% (7/36) | 34.3% (12/35) | 14.3% |

*p < 0.05 (Chi-square)

In sum, Study 4.1.8 confirms that the selected Rx100 dosing regimen provides a clinically and statistically significant survival advantage in C57BL/6 female mice who receives a potentially lethal dose of partial body irradiation with tibial sparing at Day 10 and Day 30 after irradiation.

EXAMPLE 8

Toxicology Studies of Rx100.Lysine Salts

Rx100.L-Lysine has been subjected to a nonclinical toxicology program as shown in Table 37.

TABLE 37

Toxicology Program on Rx100.Lysine

| Study type and duration | Route of administration | Species | Compound administered* |
|---|---|---|---|
| Single-dose toxicity Repeat-dose toxicity | SC | Rats, Dogs, Monkeys | Parent |
| 1 Month Genetic toxicity | SC | Rats, Monkeys | Parent |
| Ames | In vitro | S. typhimurium, E. coli | Parent |
| In vitro cytogenetics | In vitro | HPL cells | Parent |
| Micronucleus | SC | Rats | Parent |

Single-Dose Toxicity in Rats.

Sprague-Dawley rats (n=3/sex/group) received single subcutaneous doses of Rx100.Lysine at 10, 25, 50, and 100 mg/kg and were observed for 14 days (Phase 1). In the second phase of the study, animals (n=3/sex/group) received 25 mg/kg/day for seven consecutive days with injections being rotated between two sites. Parameters evaluated included clinical signs, body weight, and gross pathology. In Phase I, doses of >10 mg/kg produced scabs beginning several days post-dose. At >50 mg/kg, transient loss of body weight occurred over the first 3 days post-dose followed by subsequent body weight gain over the following 4 days. At necropsy, scabs were observed on the skin overlying the injection site of rats given >50 mg/kg. In Phase II, transient body weight loss was followed by rebound during the 7 day treatment period. Additionally, scabs developed with delayed onset at the first two dosing sites. At necropsy, small organ size was noted for the epididymis, prostate, seminal vesicle, and testis of all three males.

Single-Dose Toxicity in Dogs.

One group of one male and one female Beagle dogs received single escalating subcutaneous doses of Rx100.Lysine at 10 and 1 (female)/1.52 (male) mg/kg. In a third dosing, both animals received 6 mg/kg of the lysine component of the formulation and were observed for 14 days (Phase 1). Parameters evaluated included clinical signs, body weight, and gross pathology. The male and female dog survived until scheduled necropsy on Day 15. Administration of Rx100 had no effect on body weight or general health of the animals. Noteworthy clinical observations were confined to skin and behavior effects. Both animals scratched at the dose site, likely contributing to observations of redness at the dose site. Swelling and a thickened/raised area were also observed during the observation period. Clinical observations were sufficient to warrant the injection of diphenhydramine. Microscopic examination revealed chronic-active inflammation with necrosis and vascular thrombus formation were present at injection site A (10 mg/kg) of both animals. Following injection of the 1 mg/kg dose, persistent scratching and swelling at dose sites was observed. No remarkable findings were noted macroscopically or microscopically at any of these dose sites. Following injection of the L-lysine component of the formulation at an independent site, redness, scratching, or swelling was not seen. No remarkable findings were noted macroscopically or microscopically at this dose sites. In conclusion, subcutaneous injection of the Rx100 formulation was not tolerated by beagle dogs because of apparent pain, scratching, or swelling at the dose sites. Macroscopic abnormalities (raised areas and thickened skin) and microscopic abnormalities (chronic-active inflammation with necrosis and vascular thrombus formation) were found only at the dose site administered 10 mg/mL. The L-lysine component was apparently not responsible for these observations because injection of 1 mL/kg of a 6-mg/mL concentration of L-lysine was well tolerated by the same animals that did not tolerate Rx100 injections.

Single-Dose Toxicity in Monkeys.

In the first phase of the range-finding monkey study, one male and one female cynomolgus monkeys received single subcutaneous doses of Rx100.Lysine at 0.3, 1, 3, 10, 25 and 75 mg/kg of free acid. The vehicle for all doses was Sterile water for injection with 10 mM L-histidine. In the 7-day repeat-dose phase, two males and females were dosed subcutaneously at 10 mg/kg/day. Parameters evaluated included clinical signs, body weight, food consumption, and clinical and anatomic pathology. In the initial phase, no meaningful treatment related effects were seen at doses up to and including 25 mg/kg. Following dosing at 75 mg/kg, animals became hunched and were obviously in pain, and there were discolorations at the dosing site. Animals were subsequently sacrificed. In the repeated dose phase, signs were limited to intermittent food consumption and adverse effects at the injection sites near the end of the treatment phase. No effects on body weights were seen.

Repeat-Dose Toxicity in Rats.

Sprague Dawley female rats (n=10/group) were administered Rx100.Lysine via subcutaneous injection at doses of 0 (sterile water for injection with 10 nM, 2, 7 and 20 mg/kg/day (free acid) for 28 days. Based on appropriate correction factors, the actual doses administered were 1.81, 6.33 and 18.1 mg/kg/day. Based on observed toxicity, high dose animals were given a dosing holiday on Days 10-14, and the dosing was reinitiated at 12.7 mg/kg/day. An additional 5/sex/group were included in the control and high dose group and served as recovery animals. Ten animals per group were sacrificed after 28 days of treatment. The remaining 5 rats per group in the control and high dose groups were then allowed a 14-day recovery period following treatment. Parameters evaluated included mortality (twice daily) clinical signs, food consumption (weekly), body weights (weekly), ophthalmoscopy (pre-dosing and prior to necropsy), hematology and clinical chemistry (Week 4), gross pathology, organ weights, and histopathology for all tissues in all dose groups. Blood samples for toxicokinetic analyses were collected from satellite groups of animals (3/sex for controls and 9/sex/group for Rx100.Lysine groups) on Days 1 and 28 (except for the high dose toxicokinetic animals which were sacrificed on Day 11 and for which clinical laboratories were also performed). All animals survived the treatment period except for one high dose female which was sacrificed on Day 10. Premortem signs in this animal included swelling in the dosing site, sensitivity to touch, changes in clinical chemistry indicating inflammation which was confirmed by histopathological examination noting mixed cell inflammation at the injection site. Injection site lesions, consisting of discoloration, scabbing, and swelling was observed in all treatment groups, with a dose relationship to both incidence and severity. Some, but not all, of these lesions resolved during the recovery period. Body weight gains were reduced at the high dose (concurrent with reduced food consumption) which improved somewhat during the dosing holiday and subsequent re-initiation of dosing, but were still significantly lower than controls at the end of the treatment phase. Body weight gains were increased during the recovery period. Ophthalmological examinations were unremarkable. Hematology changes included lower red cell parameters and higher reticulocyte counts at the middle and high dose levels. Changes in white cell parameters consisting of increased leukocyte, neutrophil, eosinophil and basophil counts and increased platelets reflected the inflammation at the injection sites. No hematological changes were seen at the end of the recovery period. Coagulation studies showed lower APPT in the females at the high dose and higher fibrinogen levels at all doses, also likely reflecting the injection site lesions and were not evident at the end of the recovery period. Clinical chemistry changes included mildly lower albumin concentration and A/G ratio, higher globulin concentration and moderately higher triglycerides at >6.33 mg/kg. Some animals also showed elevated liver enzymes at 18.1/12.7 mg/kg. At necropsy, the principal treatment related organ weight changes were dose related increased liver weights in the middle and high dose groups (both genders) and dose related decreased testicular weights in all groups of males. Secondary changes included increased spleen weights and changes in other male reproductive organs. An increase in adrenal weights may have been related to a stress response. Macroscopic changes at necropsy included small testes (middle and high dose) and lesions apparent at the injection sites in some animals at all dose levels.

Histopathological evaluation of tissues revealed principal changes in liver (dose related increased hepatocyte vacuolation at all doses), testes (degeneration and necrosis of the seminiferous tubules in all animals at the middle and high dose and in one animal at the low dose, and injection sites (chronic mixed cell inflammation at all doses). Extramedullary hematopoiesis was seen in the liver and spleen along with increased cellularity in bone marrow, and likely reflected an adaptive response to the hematological findings. Other changes were seen in male reproductive organs (decreased secretion in prostate and seminal vesicles, hypospermia in epididymides. At recovery, only effects in male reproductive organs were evident at the highest dose, with skin lesions still evident in some animals at the highest dose. Toxicokinetic data revealed dose related increases in plasma concentrations. $C_{max}$ and AUC were generally higher at the end of the study compared to day 1. No gender differences were apparent. Based on these data, a NOAEL could not be clearly established in males. However, testicular degeneration was seen in only one animal at the lowest dose of 1.81 mg/kg/day (associated with a day 27 AUC value of 5042 ng·hr/mL).

Repeat-Dose Toxicity in Monkeys.

This study will be initiated in Q1 of 2014. Rx100.Lysine will be administered subcutaneously to Cynologus monkeys (n=3/sex/group) at doses of 0 (sterile water for injection with 10 mM L-histidine), 0.1, 0.5 and 2.0 mg/kg/dose (note: these doses are tentative). An additional 2/sex/group will be added to the control and high dose group and will be subjected to a two week recovery period. Parameters to be evaluated include clinical signs, body weight, food consumption, ophthalmology, electrocardiography, clinical pathology, gross pathology, organ weights, and macroscopic and microscopic pathology. Blood samples will be collected for toxicokinetic analyses of Rx100.

Genotoxicity by Ames Test.

An Ames assay was conducted on Rx100.Lysine using *S. typhimurium* strains TA98, TA100, TA1535 and TA1537 and *E. coli* strain WP2uvrA. Two trials were performed. In the initial trial, eight concentrations were evaluated ranging from 1.6 to 5000 µg/plate (when adjusted for purity, the high concentration was 4520 µg/plate) with and without metabolic activation. See Tables 38A and 38B, respectively. In the second trial, doses ranged from 0.160 to 16 µg/plate with some strains tested with activation and others without activation. No increase in revertant colonies was reported in any strain, at any concentration, with or without metabolic activation. Thus, Rx100.Lysine was considered negative in the Ames assay.

TABLE 38A

Bacterial Reverse Mutation Assay without Metabolic Activation.

Report Title: Bacterial Reverse Mutation Assay  
Test for Induction of: Reverse mutation in bacterial cells  
Strains: *Salmonella typhimurium* and *Escherichia coli*  
Metabolizing System: Aroclor™-induced rat liver S9  
Vehicles: Test Article: Sterile Water for Injection (SWFI)  
Treatment: Plate incorporation for 52 ± 4 hours.  
Cytotoxic Effects: TA1535 and TA1537 were toxic at 4.52 and 14.5 µg/plate in the absence of S9 mix as evidenced by decreased colony counts and reduced bacterial background lawns.  
Genotoxic Effects: None Number of Independent Assays: 1  
Number of Replicate Cultures: 3  
No. of Cells Analyzed/Cultured: ~$10^8$  
Positive Controls: DI Water (sodium azide only); DMSO (all other positive controls)

Test Article: Rx100.Lysine  
Study Number: 8266660  
Location in CTD:  
GLP Compliance: Yes  
Date of Treatment: 13 May 2013 and 14 Jun. 2013

| Treatment | Dose (µg/plate) | TA98 | TA100 | TA1535 | TA1537 | WP2uvrA |
|---|---|---|---|---|---|---|
| | | \multicolumn{5}{c}{Revertant Colony Counts (Mean ± SD) Strain} | | | | |

| Treatment | Dose (µg/plate) | TA98 | TA100 | TA1535 | TA1537 | WP2uvrA |
|---|---|---|---|---|---|---|
| \multicolumn{7}{c}{Without Metabolic Activation} | | | | | | |
| Sterile Water for Injection | 50µl/plate | 13 ± 3$^N$ | 87 ± 15$^N$ | 15 ± 5$^N$ | 7 ± 1$^{MN}$ | 14 ± 4$^N$ |
| Rx100.Lysine | 0.0181 | 15 ± 3$^N$ | 92 ± 8$^N$ | 15 ± 4$^N$ | 6 ± 4$^N$ | — |
| | 0.0452 | 15 ± 5$^{NM}$ | 93 ± 16$^N$ | 16 ± 2$^N$ | 6 ± 3$^{NM}$ | — |
| | 0.145 | 13 ± 2$^{NM}$ | 88 ± 11$^N$ | 12 ± 1$^N$ | 5 ± 0$^{MN}$ | — |
| | 0.452 | 13 ± 5$^N$ | 86 ± 13$^N$ | 11 ± 3$^N$ | 6 ± 3$^{MN}$ | — |
| | 1.45 | 14 ± 2$^N$ | 84 ± 16$^N$ | 11 ± 2$^N$ | 5 ± 2$^N$ | 12 ± 5$^N$ |
| | 4.52 | 12 ± 4$^N$ | 53 ± 7$^R$ | 8 ± 3$^N$ | 3 ± 4$^N$ | 13 ± 3$^{MN}$ |
| | 14.5 | 12 ± 3$^N$ | 51 ± 4$^{MR}$ | 4 ± 1$^{RM}$ | 1 ± 1$^{RM}$ | 17 ± 6$^N$ |
| | 45.2 | — | — | — | — | 14 ± 4$^N$ |
| | 145 | — | — | — | — | 15 ± 3$^N$ |
| | 452 | — | — | — | — | 12 ± 2$^N$ |
| | 1450 | — | — | — | — | 8 ± 3$^E$ |
| | 4520 | — | — | — | — | 0 ± 0$^E$ |
| 2-nitrofluorene | 1.0 | 329 ± 65$^N$ | — | — | — | — |
| sodium azide | 2.0 | — | 969 ± 137$^N$ | 863 ± 45$^N$ | — | — |
| ICR-191 | 2.0 | — | — | — | 562 ± 33$^N$ | — |
| 4-nitroquinoline-N-oxide | 1.0 | — | — | — | — | 601 ± 6.8$^N$ |

TABLE 38B

Bacterial Reverse Mutation Assay with Metabolic

| Treatment | Dose (µg/Plate) | TA98 | TA100 | TA1535 | TA1537 | WP2uvrA |
|---|---|---|---|---|---|---|
| \multicolumn{7}{c}{With Metabolic Activation} | | | | | | |
| Sterile Water for injection | 50µl/plate | 20 ± 3$^N$ | 115 ± 1$^N$ | 13 ± 2$^{NM}$ | 5 ± 1$^N$ | 16 ± 3$^N$ |
| Rx100.Lysine | 0.0181 | — | — | 10 ± 4$^{NM}$ | — | — |
| | 0.0452 | — | — | 11 ± 2$^{CMN}$ | — | — |
| | 0.145 | — | — | 9 ± 3$^N$ | — | — |
| | 0.452 | — | — | 13 ± 1$^N$ | — | — |
| | 1.45 | 17 ± 5$^N$ | 114 ± 12$^N$ | 11 ± 5$^N$ | 9 ± 3$^N$ | 13 ± 4$^N$ |
| | 4.52 | 19 ± 3$^N$ | 117 ± 5$^N$ | 9 ± 1$^N$ | 7 ± 2$^{NM}$ | 17 ± 4$^{MN}$ |
| | 14.5 | 16 ± 5$^N$ | 89 ± 14$^N$ | 11 ± 3$^N$ | 6 ± 5$^{MN}$ | 19 ± 4$^N$ |
| | 45.2 | 20 ± 6$^N$ | 26 ± 3$^E$ | — | 3 ± 2$^E$ | 12 ± 4$^N$ |
| | 145 | 0 ± 0$^E$ | 39 ± 3$^{MR}$ | — | 0 ± 0$^R$ | 15 ± 4$^{NM}$ |
| | 452 | 0 ± 0$^V$ | 0 ± 0$^{AT}$ | — | 0 ± 0$^V$ | 15 ± 5$^N$ |
| | 1450 | 0 ± 0$^A$ | 0 ± 0$^{MAT}$ | — | 0 ± 0$^V$ | 9 ± 3$^N$ |
| | 4520 | 0 ± 0$^A$ | 0 ± 0$^{AT}$ | — | 0 ± 0$^A$ | 0 ± 0$^E$ |

TABLE 38B-continued

Bacterial Reverse Mutation Assay with Metabolic

|  | Dose | Revertant Colony Counts (Mean ± SD) Strain | | | | |
|---|---|---|---|---|---|---|
| Treatment | (µg/Plate) | TA98 | TA100 | TA1535 | TA1537 | WP2uvrA |
| benzo[a]pyrene | 2.5 | 487 ± 62$^N$ | — | — | — | — |
| 2-amnioanthracene | 2.5 | — | 2106 ± 68$^N$ | 205 ± 11$^N$ | 176 ± 19$^{NC}$ | — |
| 2-aminoanatacene | 25.0 | — | — | — | — | 634 ± 14$^N$ |

GLP = Good Laboratory Practice,.
Criteria for a positive response (increase over corresponding control), 2-fold for TA98, TA100, and WP2uvrA;3-fold for TA1535 and T)
$^R$Reduced background bacterial lawn;
$^A$Absence of backmund bacterial lawn:
$^B$Precipitation of test article observed;
$^E$Enhanced background bacterial lawn;
$^T$Toxic, no revertant colonies:
$^M$Plates manually counted;
$^N$Normal background bacterial lawn;
$^C$Contaminated plate:
$^V$Very thin backgound bacterial lawn Genotoxicity by In Vitro Mammalian Cell System.

Cultured human peripheral lymphocytes cells were incubated in vitro with Rx100.Lysine for 3 hours with and without S9 mix and for 24 hours without S9 mix. For Rx100.Lysine, concentrations ranging from 3.39 to 500 µg/mL were examined in both treatment conditions. Adjusting for purity, the concentration ranges were 3.06 to 452 µg/mL. Cytotoxicity was observed at the highest concentration tested for the 3-hour exposure. No increase in structural or numerical aberrations, polyploidy or endoreduplication in the cultures treated for 3 hours with or 24 hours without metabolic activation. A small but statistically significant increase in cells with chromosome aberrations was observed only in the cultures treated at 316 µg/mL for 3 hours without metabolic activation. This increase was at a high dose with no statistically significant increase observed at the next lower dose, but closely spaced concentration. This increase was just above the historical vehicle control range (0 to 2.0%) for 3 hour treatment without metabolic activation. Thus the response observed is a weak positive and of questionable biological significance cytotoxicity was present just below the acceptable limit of 50±5% for this assay. See Table 39A and 39B for details.

TABLE 39A

Chromosomal Aberrations in Cultured Human Peripheral Blood Lymphocytes without Metabolic Activation.

Report Title: Chromosomal Aberrations in Cultured Human Peripheral Blood Lymphocytes
Test for Induction of: Chromosome aberrations   Number of Independent Assays: 1   Test Article: Rx100.Lysine
Strains: Primary human lymphocytes   Number of Replicate Cultures: 2   Study No.: 8266661
Metabolizing System: Aroclor™ -induced rat liver S9   Number of Cells Analyzed/Culture: 100   GLP Compliance: Yes
(or ≥25 if >25% cells with aberrations)   Date of Treatment: 15 May 2913
(Trial B1)/ 06 Jun. 2013 (Trial B2)

Vehicles:   Test Article: Sterile Water for Injection (SWFI)   Positive Controls: Deionized (DI) Water
Treatment: Continuous 24 hour without S9; pulse treatment 3 hour and recovery time 21 hour with and without S9.
Cytotoxic Effects: None
Genotoxic Effects: Negative for inducing chromosome aberrations, polyploidy and endoreduplication following a 3 hour treatment with and a 24 hour treatment without S9. Weakly positive for inducing chromosome aberrations, but not polyploidy or endoreduplication following a 3 hour treatment without S9.

| Test Article | Dose (ug/mL) | Total Cells Analyzed | Cytotoxicity$^a$ (% of control) | Aberrant Cells | | Polyploidy Mean % | Eudore-duplicate Mean % |
|---|---|---|---|---|---|---|---|
| | | | | Mean % −g | Mean % +g | | |
| 24-Hour Treatment Without Metabolic Activation | | | | | | | |
| SWFI | 100 µL/mL | 200 | 100 | 0.5 | 1.5 | 0.0 | 0.0 |
| Rx100.Lysine | 41.2 | 200 | 77 | 0.5 | 3.0 | 0.0 | 0.0 |
| | 84.0 | 200 | 83 | 2.0 | 5.5 | 0.0 | 0.0 |
| | 120 | 200 | 64 | 0.5 | 4.5 | 1.0 | 0.0 |
| Mitomycin C | 0.300 | 100 | 41 | 58.0 | 61.0 | 0.0 | 0.0 |
| 3-Hour Treatment Without Metabolic Activation | | | | | | | |
| SWFI | 100 µL/mL | 200 | 190 | 0.5 | 2.5 | 0.0 | 0.0 |
| Rx100.Lysine | 120 | 200 | 74 | 0.5 | 1.0 | 0.5 | 0.0 |
| | 245 | 200 | 68 | 3.0 | 6.0 | 1.5 | 0.0 |

TABLE 39A-continued

Chromosomal Aberrations in Cultured Human Peripheral
Blood Lymphocytes without Metabolic Activation.

|  | 350 | 200 | 53 | 6.0 | 8.5 | 3.0 | 0.0 |
|---|---|---|---|---|---|---|---|
| Mitomycin C | 1.00 | 100 | 52 | 57.0 | 59.0 | 0.0 | 0.0 |

GLP = Good Laboranny Practice.
−g = % of aberrant cells excluding those with gaps only;
+g = % of aberrant cells phis % of cells with gaps only.
*Signficantly greater in −g than the vehical control, $p \leq 0.01$
**Significantly greater in polyploidy than the vehicle control, $p \leq 0.01$ Thus, Rx100.Lysine was considered negative for inducing chromosome aberrations, polyploidy and endoreduplication, in cultured human peripheral blood lymphocytes following a 3 hour treatment with and a 24 treatment without metabolic activation. Rx100.Lysine was considered weakly positive for inducing chromosome aberrations, but not polyploidy or endoreduplication in cultured human peripheral blood lymphocytes following a 3 hour treatment without metabolic activation.

TABLE 39B

Chromosomal Aberrations in Cultured Human Peripheral Blood Lymphocytes with Metabolic Activation.

| Treatment | Dose (μg/mL) | Total Cells Analyzed | Cytotoxicity$^a$ (% of Control) | Aberrant Cells Mean % −g | Aberrant Cells Mean % +g | Polyploidy Mean % | Endure-duplicate Mean % |
|---|---|---|---|---|---|---|---|
| 3-Hour Treatment With Metabolic Activation ||||||||
| SAVFI | 100 μL/mL | 200 | 100 | 0.5 | 1.5 | 0.0 | 0.0 |
| Rx100.Lysine | 84.0 | 200 | 77 | 0.0 | 1.5 | 0.0 | 0.0 |
|  | 120 | 200 | 65 | 0.5 | 2.5 | 0.0 | 0.0 |
|  | 172 | 200 | 68 | 0.5 | 3.0 | 0.0 | 0.0 |
| Cyclophosphamide | 25.0 | 100 | 12 | 58.0 | 65.0 | 0.0 | 0.0 |

GLP = Good Laboratory Practice:
−g = % of aberrant cells excluding those with gaps only;
+g = % of aberrant cells plus % of cells with gaps only.
*Signficantly greater in −g than the vehicle control, $p \leq 0.01$
**Signficantly greater in polyploidy than the vehicle control, $p \leq 0.01$
$^a$Cytotoxicity = [One minus the quotient (mean test article mitotic index/mean vehicle control mitotic index)] × 100.

Genotoxicity by In Vivo Mammalian System.

A GLP-compliant rat micronucleus study was performed using male Sprague-Dawley rats (n=5/group) administered single subcutaneous doses of Rx100.lysine at 0 (0.5% sterile water for injection with 10 mM L-histidine), 125, 250, and 5000 mg/kg (doses corrected for purity were 113, 225 and 452 mg/kg). One additional group received the positive control material (cyclophosphamide). Five animals per group were sacrificed 24 hours postdose; five animals from the vehicle and high dose group were sacrificed 48 hours postdose. Following sacrifice, bone marrow cells were collected from the femur. 2000 PCEs per animal were analyzed for the frequency of micronuclei. Dose formulation analyses revealed concentrations ranging from 98.2 to 102.1% of target. The materials were also shown to be homogenous (relative standard deviation [RSD] of 0.7 to 0.9%). Clinical signs were limited to hunched posture, hypoactivity and irregular respiration seen in the high dose animals at 48 hours postdose. As shown in Table X, no increase in micronucleated PCEs was noted at any dose at the 24 hour point. A statistically significant increase was noted in the high dose animals at the 48-hour time point, which was not considered to be biologically relevant. Thus, Rx100.Lysine was considered to be negative in the micronucleus assay.

TABLE 40

In vivo Rat Bone Marrow Micronucleus Assay.
Report Title: In Vivo Rat Bone Marrow Micronucleus Assay

| | | |
|---|---|---|
| Test for Induction of: Bone marrow micronuclei | Treatment Schedule: One dose | Test Article: Rx100.Lysine |
| Species/Strain: Rat/ Sprague-Dawley | Sampling Time: 24 and 48 hours after dosing | Study Number: 8266662 |
| Age: 11 weeks | Number of Cells Analyzed/Animal: 2000 | GLP Compliance: Yes |
| | Cells Evaluated: Polychromatic erythrocytes | Date of Treatment; 21 May 2013 |

TABLE 40-continued

In vivo Rat Bone Marrow Micronucleus Assay.
Report Title: In Vivo Rat Bone Marrow Micronucleus Assay Method of Administration: Vehicle/Test Article: Subcutaneous Injection Positive Control: Oral Gavage
Vehicle/Formulation: Test/Article: 10 mM Histidine in Sterile Water for Injection (SWI), USP Positive Control: Deionized (DI) Water
Toxic/Cytotoxic Effects: Rx100.Lysine was cytotoxic to the bone marrow (i.e., statistically significant decreases in the PCE:NCE ratios at all doses of the test article.
Genotoxic Effects: None. The mean percent micronucleated PCEs in the bone marrow of the high dose 48 hour animals were well within the historical vehicle control range for 48 hours.

| Treatment | Dose[a] | Number of Males | Harvest Time (Hour) | Mean Ratio PCE:NCE (±SD) Male | Mean % MNPCE (±SD) Male |
|---|---|---|---|---|---|
| Vehicle Control | 10 mL/kg | 5 | 24 | 0.81 ± 0.11 | 0 05 ± 0.05 |
|  |  | 5 | 48 | 0.80 ± 0.06 | 0.02 ± 0.04 |
| Test Article | 125 mg/kg | 5 | 24 | 0.55 ± 0.08* | 0.04 ± 0.02 |
|  | 250 mg/kg | 5 | 24 | 0.59 ± 0.14* | 0.07 ± 0.03 |
|  | 500 mg/kg | 5 | 24 | 0.52 ± 0.11* | 0.09 ± 0.05 |
|  |  | 5 | 48 | 0.36 ± 0.07* | 0.08 ± 0.03* |
| Cyclophosphamide | 60 mg/kg | 5 | 24 | 0.44 ± 0.14* | 1.09 ± 0.18** |

*Significantly different than the corresponding vehicle control, $p \leq 0.01$.
**Significantly different than the corresponding vehicle control, $p \leq 0.05$.
Vehicle Control = 10 mM Histidine in Sterile Water for Injection, USP (SWFI)
GLP = Good Laboratory Practice:
MNPCE = Micronucleated PCEs
NCE = Normochromatic erythrocyte
PCE = Polychromatic erythrocyte
SD = Standard Deviation
[a]The actual doses after being corrected for a purity of 50.9% were 113, 226, and 452 mg/kg

EXAMPLE 9

Pharmacology and Mechanism of Action of RX100

Rx100 is a pan lysophosphatidic acid receptor (LPAR) agonist. The compound was medicinally designed as an LPA analog with the goal of decreasing the otherwise rapid metabolism of LPA itself. At this point, there are 6 known LPARs (1-6) although there are suggestions that others may exist (e.g., GPR35 and 87, P2Y10). These receptors are ubiquitous by tissue and in those eukaryotes investigated. We have found that the LPAR2 subtype is responsible for protection of the gut stem cell from irradiation based on in vivo studies in knock-out mice and from in vitro data. Thus, the mechanism of drug action for GI-ARS protection is activation of the transmembrane G protein-coupled lysophosphatidic acid receptor (LPAR) and, more specifically, the LPAR2 GPCR subtype. The primary pharmacodynamics is that LPAR2 activation leads to a cascade of intracellular events that switch cells from an apoptotic to a repair/regenerative pathway.

It appears that the primary pharmacodynamic effect is entirely intracellular based on activation of pathways that block apoptosis and stimulate prosurvival pathways. For the former, activation of the transmembrane LPAR may result in intracellular steps that promote the degradation of the pro-apoptotic Siva-1 which can then no longer degrade Bcl-XL. On the latter, LPA binding to LPAR2 may result in activation of ERK1/2 & PI3K-AKT-NFkB prosurvival pathways. The net result is enhanced intracellular repair and regeneration of the gut stem cell after an apoptotic stimulus such as radiation-induced damage or the presence of soluble factors from neighboring dying cells that may stimulate apoptosis.

Radiosensitive proliferating or clonogenic cells (such as GI stems cells at position 3-5 in the crypt above the Paneth cells) that suffer DNA damage enter a resting phase within a few minutes to hours after injury. During this growth arrest, after about 4-24 hours in mice, these cells either initiate an apoptotic cascade or enter into a period of repair leading to regeneration by mitosis. In the latter setting, DNA damage can still result in daughter cell death following ineffective mitosis from genomic instability. A nadir in stem cell numbers was seen at approximately Day 2 with recovery initiating by Day 3 as has been shown in our studies of irradiated C57BL/6 mice. The villi remain relatively intact during this period but then suffer villus collapse at around Day 3 with, most likely, consequential onset of clinical diarrhea and fluid loss and, perhaps, subsequent bacterial translocation and sepsis. A single surviving and successfully dividing stem cell can result in crypt and villus restoration over the ensuing 5 to 30 days. Based on the likelihood of ongoing injury, whether from inflammation or soluble factors, Rx100's mechanism of action suggests maximal pharmacological activity in the immediate period after irradiation through 3 days after irradiation when the majority of stem cells will have either died or survived to mitotic capability. Further, supportive care during the period of villus collapse will be important to permit patients to weather through to crypt and villus recovery.

We investigated structure-activity relationships across species, LPAR subtypes and between Rx100 and two known process impurities encountered in manufacture: Rx103 ('E' isomer) and Rx200 (oleyl phosphate and impurity, which can be an Rx100 degradant along with oleyl alcohol). Rx100, Rx103, Rx200 and native LPA were investigated at different human LPAR subtypes. In addition, the activity of these compounds was evaluated at LPA2 receptors from the rhesus, rat and mouse species. Human LPA1/2/3 subtypes were transfected into mouse embryonic fibroblasts (MEF) or rat hepatoma cells (RH7777)—both of which are normally non-responsive or null to LPA. Human LPA4 was transfected into Chinese hamster ovary (CHO) cells and LPA5 into the B103 neuroblastoma cell line. While the CHO cell line endogenously expresses LPA1 receptors and thus, shows modest response to LPA, the increase after transfection with the LPA4 receptor subtype is measurable. The LPA4 receptor, for reasons not yet understood, does not express well in other endogenously LPA nonresponsive cell hosts such as the MEF, RH7777, or B103. The B103 rat neuroblastoma cell line is endogenously nonresponsive to LPA but expresses heterologous LPA5 receptors well. Identification of maximal ($E_{max}$) and 50% activation ($EC_{50}$) were performed by titration against an LPA standard in a standard calcium-mobilization assay. LPAR activation elicits a G-protein-mediated transient rise in intracellular calcium level that is proportional to the concentration of LPA applied. The intracellular calcium level was quantified by the calcium-selective fluorescent indicator FURA-2 (e.g., increased intracellular calcium surge=increased fluorescence). As shown in Table 41, Rx200 is inactive in all species and LPAR subtypes tested. Rx103 has activity but has a uniformly reduced $EC_{50}$ and $E_{max}$.

TABLE 41

Relative lysophosphatidic acid receptor activation of Rx100, R103, Rx200 and lysophosphatidic acid by species and receptor subtype ($EC_{50}$ and $E_{max}$)

| Receptor host | EC50 [nM] | | | | Emax (% of LPA) | | | | |
|---|---|---|---|---|---|---|---|---|---|
| Species | LPA | Rx100 | Rx103 | Rx200 | LPA | Rx100 | Rx103 | Rx200 | |
| LPA1 DKO MEF - | 354 | 273 | 367 | 1363 | 100 | 70 | 90 | 53 | mean (nM) |
| human | 122 | 87 | 168 | 211 | 0 | 1 | 12 | 9 | SD |
| LPA1 RH7777 | 28 | 1028 | 1707 | 328 | 100 | 69 | 75 | 83 | mean (nM) |
| human | 19 | 485 | 894 | 142 | 0 | 12 | 23 | 24 | SD |
| LP42 DKO MEF - | 1.7 | 124 | 241 | No activity | 100 | 100 | 70 | No activity | mean (nM) |
| human | 0.7 | 15 | 98 | | 0 | 0 | 9 | | SD |
| LPA2 DKO NEF - | 1.3 | 103.8 | 133 | No activity | 100 | 100 | 90 | No activity | mean (nM) |
| rhesus | 0.1 | 40 | 32 | | 0 | 0 | 19 | | SD |
| LPA2 DKO 11E6 - | 1.7 | 76 | 133 | No activity | 100 | 100 | 87.6 | No activity | mean (nM) |
| rat | 0.4 | 35 | 31 | | 0 | 0 | 9 | | SD |
| LPA2 DKO MEF - | 4.4 | 167 | 355 | No activity | 100 | 100 | 100 | No activity | mean (nM) |
| mouse | 1.9 | 79 | 179 | | 0 | 0 | 17 | | SD |
| LPA3 DKO MEF | B34 | 205 | 61 | >5,000 | 100 | 82 | 100 | 34 | mean (nM) |
| human | B1 | 104 | 36 | NA | 0 | 9 | 28 | 13 | SD |
| LPA3 RH7777 | 265 | 113 | 74 | 747 | 100 | 71 | 77 | 61 | mean (nM) |
| human | 66 | 70 | 40 | 350 | 0 | 7 | 21 | 14 | SD |
| LPA4 CHO | 268 | >5,000 | >5,000 | 737 | 100 | 97 | 88 | 70 | mean (nM) |
| human | 87 | NA | NA | 326 | 0 | 3 | 1 | 12 | SD |
| LPA5 B103 | 513 | 100 | 83 | 167 | 100 | 104 | 103 | 100 | mean (nM) |
| human | 177 | 55 | 50 | 129 | 0 | 4 | 8 | 4 | SD |
| Control DKO MEF | | | | | No activity | | | | |
| Control RH7777 | | | | | No activity | | | | |
| Control CHO | 605 | >5,000 | >5,000 | 965 | 12% | 20% | 12% | 12% | |
| Control B103 | | | | | No activity | | | | |

NA - Not applicable
RH - Rat hepatome
B103 - rat neuroblastoma
DKO - double knock-out
CHO - Chinese hamster ovary A further study was performed to evaluate whether Rx100 displaces lysophosphatidic acid bound to its receptor. HEK293 cells were transfected with human LPA2 receptor. Crude membrane fraction was isolated from these cells and 80 μg aliquots of membrane protein were incubated with 20 nM [3H]LPA (1-oleoyl-[9,10-3H]LPA and various concentrations of cold Rx100. Nonspecific binding was determined by adding 10 μM nonradioactive LPA. The result of a representative competition binding assay is shown in FIG. 35. Rx100 displaced 3H-LPA in a concentration-dependent manner from binding to the human ortholog of LPA2. This finding provides further evidence that Rx100 selectively targets the LPAR2.

In sum, among potential impurities and degradants, Rx100 provides substantially more in vitro activity than the corresponding trans-isomer (Rx103) or the phosphate derivative (Rx200) of Rx100. The latter is virtually inactive. Oleyl alcohol is, of course, a common component of many non-toxic ingested or dermally applied substances.

Further, a comprehensive safety pharmacology assessment has been conducted on Rx100.lysine. The studies were compliant with Good Laboratory Practices (GLPs) unless otherwise noted.

Central Nervous System.

Four groups of male Sprague Dawley rats (n=8/group) were administered Rx100.lysine via subcutaneous injection at doses of 0 (10 mM histidine in sterile water for Injection, USP), 1.81, 6.33 and 18.1 mg/kg as the free acid. Animals were assessed pre-dose and through 24 hours post-dose for a variety of behavioral, neurological and autonomic responses using the modified Irwin battery of assessments. Dose formulation analyses were conducted and samples ranged from 99 to 104% of target. The only effect observed was a small (0.8 to 1.5 degrees C.) decrease in body temperature noted at 2-4 hours postdose. No other effects on the parameters evaluated were observed.

Cardiovascular System.

Four male telemetered cynomolgus monkeys were selected, and assigned via a Latin Square design to receive four doses of Rx100.lysine or vehicle via subcutaneous injection at doses of 0 (10 mM histidine in sterile water for injection, USP), 0.1, 0.5 and 2.0 mg/kg as the free acid. Parameters evaluated include clinical observations, body temperature, arterial pressure and ECG evaluations (PR, QT, QRS durations). QTc values were calculated based on data collected for each animal. No qualitative abnormalities were identified that were attributed to Rx100.Lysine and no meaningful changes in PR, QRS, QT and QTc were identified. There was a slight dose-dependent increase in heart rate. In addition, an hERG assay to test effects of Rx100 on cloned hERG Potassium Channels expressed in human embryonic kidney cells demonstrated an $IC_{50}$ at about 600 µM which is 100-fold anticipated therapeutic concentrations.

Respiratory System.

Male Sprague-Dawley rats (n=6/group) were administered Rx100.lysine as a single oral (gavage) doses of 0 (10 mM histidine in sterile water for injection, USP), 1.81, 6.33, and 18.1 mg/kg and monitored for respiratory function. Animals were placed in a plesthymograph and monitored at pre-dose and for consecutive 30 minute averages beginning 30 minutes postdose through 6 hours postdose and again at 24 hours postdose. Parameters evaluated included tidal volume, respiratory rate and minute volume. Dose formulation analyses were performed and indicated that the concentrations ranged from 100 to 105% of target. No statistically significant or biologically meaningful effects were noted on any of the respiratory parameters at the dose of 1.81 mg/kg. At the two higher doses of 6.33 and 18.1 mg/kg, there was a dose-related reduction in tidal volume (29% and 32%, respectively) and an increase in respiratory rates (68% and 65%, respectively). At 6.33 mg/kg, values were essentially normal 24 hours post dose, but values at 18.1 mg/kg still showed effects at 24 hours post dose, although reduced in magnitude. It was concluded that there were no adverse effects on the respiratory system in rats at doses of 1.81 mg/kg.

Gastrointestinal System.

Male Sprague-Dawley rats (n=6/group) were administered Rx100.lysine as a single oral (gavage) doses of 0 (10 mM histidine in sterile water for Injection, USP), 1.81, 6.33, and 18.1 mg/kg and monitored for gastrointestinal parameters of transit time and gastric emptying. A fifth group was treated with the positive control material morphine sulfate. Two hours after treatment, animals received an oral gavage dose of a charcoal suspension. Animals were then sacrificed 20 minutes. Parameters evaluated included gastrointestinal transit time and gastric emptying. Dose formulation analyses were performed and indicated that the concentrations ranged from 99% to 106% of target. No abnormal observations were recorded. However, gastric emptying was inhibited at 6.33 and 18.1 mg/kg but was statistically significant only at 6.33 mg/kg. Intestinal transit time was increased only at 18.1 mg/kg. It was concluded that there were no adverse effects on the gastrointestinal tract in rats at doses of 1.81 mg/kg (gastric emptying) or 6.33 mg/kg (transit time).

Pharmacodynamic Drug Interactions.

There are no data on pharmacodynamic drug interactions in part because there are as yet no known pharmacodynamic markers of Rx activity. See 2.6.2.2. Rx acts through and transmembrane receptor and intracellular pathways. The effect of Rx100 alone, G-CSF alone, and in combination general on inflammatory markers, such as lymphocyte subsets and certain cytokines (IL-15 and GM-CSF), and citrulline (a marker of gut integrity or endothelial mass), which appear to parallel progression of GI-ARS, are being evaluated.

Thus, Rx100 was identified as having no meaningful adverse effect on the central nervous system, cardiovascular system, gastrointestinal system and respiratory system at a dose level of 1.8 mg/kg. At higher doses, reversible effects on heart rate (increase), body temperature (decrease), respiratory rate (increase) and gastrointestinal transit time (decrease) were seen—all apparently related to a period of general arousal after drug dosing.

While the present invention has been disclosed with reference to certain embodiments, numerous modifications, alterations, and changes to the described embodiments are possible without departing from the full scope of the invention, as described in the specification and claims.

What we claim are:

1. A salt of (Z)—O-octadec-9-en-1-yl O,O-dihydrogen phosphorothioate with an L-Lysine addition in a crystalline form, wherein said crystalline form exhibits an X-ray powder diffraction pattern comprising peaks expressed in 2-Theta degrees substantially at 5.29°, 7.07°, 8.83°, 10.62°, 14.19°, 16.00°, 17.79°, 18.52°, 18.99°, 19.40°, 23.27°, 25.05°, and 32.85°.

2. A pharmaceutical composition comprising the salt of claim 1 and a pharmaceutically acceptable carrier.

* * * * *